US010221158B2

(12) United States Patent
Ohlmeyer et al.

(10) Patent No.: US 10,221,158 B2
(45) Date of Patent: Mar. 5, 2019

(54) HETEROCYCLIC CONSTRAINED TRICYCLIC SULFONAMIDES AS ANTI-CANCER AGENTS

(71) Applicant: ICAHN SCHOOL OF MEDICINE AT MOUNT SINAI, New York, NY (US)

(72) Inventors: Michael Ohlmeyer, Plainsboro, NJ (US); Nilesh Zaware, Briarwood, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 15/758,038

(22) PCT Filed: Sep. 8, 2016

(86) PCT No.: PCT/US2016/050685
§ 371 (c)(1),
(2) Date: Mar. 7, 2018

(87) PCT Pub. No.: WO2017/044567
PCT Pub. Date: Mar. 16, 2017

(65) Prior Publication Data
US 2018/0251444 A1 Sep. 6, 2018

Related U.S. Application Data

(60) Provisional application No. 62/216,168, filed on Sep. 9, 2015.

(51) Int. Cl.
C07D 401/04 (2006.01)
C07D 401/14 (2006.01)
C07D 405/04 (2006.01)
C07D 417/04 (2006.01)
C07D 417/14 (2006.01)
A61P 35/00 (2006.01)

(52) U.S. Cl.
CPC .......... C07D 401/04 (2013.01); A61P 35/00 (2018.01); C07D 401/14 (2013.01); C07D 405/04 (2013.01); C07D 417/04 (2013.01); C07D 417/14 (2013.01)

(58) Field of Classification Search
None
See application file for complete search history.

(56) References Cited

U.S. PATENT DOCUMENTS

| 4,634,766 A | 1/1987 | Atkinson et al. |
| 4,668,671 A | 5/1987 | Gribble et al. |
| 4,882,351 A | 11/1989 | Oshima et al. |
| 6,583,138 B1 | 6/2003 | Miyamoto et al. |
| 9,540,358 B2 | 1/2017 | Ohlmeyer et al. |
| 2002/0103189 A1 | 8/2002 | Miyamoto et al. |
| 2008/0275023 A1 | 11/2008 | Guidi et al. |
| 2015/0376191 A1 | 12/2015 | Ohlmeyer et al. |
| 2017/0015625 A1 | 1/2017 | Ohlmeyer et al. |
| 2017/0015630 A1 | 1/2017 | Ohlmeyer et al. |

FOREIGN PATENT DOCUMENTS

| CN | 102942562 A | 2/2013 |
| EA | 15779 B1 | 12/2011 |
| EP | 0679641 A1 | 11/1995 |
| EP | 0881220 A1 | 12/1998 |
| EP | 1481673 A1 | 12/2004 |
| WO | 2002/024657 A2 | 3/2002 |
| WO | 2004052847 A2 | 6/2004 |
| WO | 2006/066879 A2 | 6/2006 |
| WO | 2006116157 A2 | 11/2006 |
| WO | 2006117183 A1 | 11/2006 |
| WO | 2008/121859 A1 | 10/2008 |
| WO | 2013025882 A2 | 2/2013 |
| WO | 2014031986 A1 | 2/2014 |

(Continued)

OTHER PUBLICATIONS

International Search Report & Written Opinion issued in PCT/US2016/050685, dated Oct. 26, 2016.
International Search Report & Written Opinion issued in PCT/US2015/019770, dated May 8, 2015.
RN 1350122-38-1 CAS Registry, entered STN: Dec. 7, 2011.
Extended EP Search Report for EP 12823881.3 dated Mar. 3, 2015.
International Search Report for PCT/US2012/051097 dated Feb. 20, 2013.
International Search Report for PCT/US2014/017127 dated May 20, 2014.
Alfredsson et al., "Mass Fragmentographic Analysis of Clomipramine and Its Mono-Demethylated Metabolite in Human Plasma" Psychopharmacology, 52, 25-30 (1977).

(Continued)

Primary Examiner — Alicia L Otton
(74) Attorney, Agent, or Firm — Heslin Rothenberg Farley & Mesiti P.C.

(57) ABSTRACT

A genus of arylsulfonamide derivatives of heterocyclic constrained tricyclic compounds is disclosed. The compounds are of the following genus:

The compounds induce FOXO1 transcription factor translocation to the nucleus by modulating PP2A and, as a consequence, exhibit anti-proliferative effects. They are useful in the treatment of a variety of disorders, including as a therapy in cancer treatment, or used in combination with other drugs to restore sensitivity to chemotherapy where resistance has developed.

20 Claims, No Drawings

(56) References Cited

FOREIGN PATENT DOCUMENTS

| WO | 2014130534 A1 | 8/2014 |
|---|---|---|
| WO | 2015/138500 A1 | 9/2015 |
| WO | 2015138496 A1 | 9/2015 |
| WO | 2017/024229 A1 | 2/2017 |
| WO | 2017/044569 A1 | 3/2017 |
| WO | 2017/044571 A1 | 3/2017 |
| WO | 2017/044572 A1 | 3/2017 |
| WO | 2017/044575 A1 | 3/2017 |

OTHER PUBLICATIONS

Midgley et al., "Synthesis of [13C$_2$]-Amitriptyline, Nortriptyline and Desmethynortriptyline" Journal of Labelled Compounds and Radiopharmaceuticals, vol. XV, pp. 511-521 (1978).

Hadrich et al., "Synthesis and Characterization of Fluorescent Ligands for the Norepinephrine Transporter: Potential Neuroblastoma Imaging Agents", Journal of Medicinal Chemistry, American Chemical Society, US, vol. 42, No. 16, Jul. 16, 1999 (Jul. 16, 1999), pp. 3101-3108, XP003003932, ISSN: 0022-2623, DOI: 10.1021/JM9811155.

Runyon et al., "Influence of Chain Length and N-Alkylation on the Selective Serotonin Receptor Ligand 9-(Aminomethyl)-9,10-dihydroanthracene", Bioorganic & Medicinal Chemistry Letters 11 (2001), 655-658.

Van Dort et al., Synthesis of $^{11}$C-Labeled Desipramine and its Metabolite 2-Hydroxydesipramine: Potential Radiotracers for PET Studies of the Norepinephrine Transporter, Nuclear Medicine & Biology, vol. 24, pp. 707-711, 1997.

Ilies et al., "Protease Inhibitors: Synthesis of Bacterial Collagenase and Matrix Metalloproteinase Inhibitors Incorporating Arylsulfonylureido and 5-Dibenzo-suberenyl/suberyl Moieties", Bioorganic & Medicinal Chemistry, 11 (2003) 2227-2239.

Yang et al., "Catalytic decarboxylative alkylation of B-keto acids with sulfonamides via the cleavage of carbon-nitrogen and carbon-carbon bonds," Chemical Communications, 2011 (published on Web: Jun. 22, 2011), vol. 47, No. 29, pp. 8343-8345.

Azuine et al., "Cancer chemopreventive effect of phenothiazines and related tri-heterocyclic analogues in the 12-0-tetradecanoylphorbol-13-acetate promoted Epstein-Barr virus early antigen activation and the mouse skin two-stage carcinogenes is models," Pharmacological Research, 2004, vol. 49, No. 2, pp. 161-169.

Ohshima, et al., "Non-Prostanoid Thromboxane A$_2$ Receptor Antagonists with a Dibenzoxepin Ring System. 2" J. Med. Chem, 1992, 35, 3402-3413.

Morak-Mlodawska et al., "Acyl and Sulfonyl Derivatives of 10-Aminoalkyl-2,7-Diazaphenothiazines#, Heterocycles", vol. 78, No. 5, 2009 pp. 1289-1298.

Alfonso et al., "Synthesis of a C$_{11}$ Spiropiperidino derivative of 8-Chloro-6,11-dihydro 5H-Benzo [5,6] cyclohepta[1,2-b]pyridine", Tetrahedron Letters 39, 1998, 7661-7664.

Kau et al., A chemical genetic screen identifies inhibitors of regulated nuclear export of a Forkhead transcription factor in PTEN-deficient tumor cells, Cancer Cell, XP008037524, Dec. 2003, pp. 463-476.

Jelen et al., "Synthesis of 6-Aminoalkyldiquino-1,4-Thiazines and Their Acyl and Sulfonyl Derivatives, Heterocycles", vol. 4, No. 4, XP055279565, 2008, pp. 859-870.

Pluta et al., "Anticancer activity of newly synthesized azaphenothiazines from NCI's anticancer screening bank#", Pharmaceutical Reports, 2010, 62, 319-332.

Motohashi et al., "Synthesis and Biological Activity of N-acylphenothiazines" International Journal of Antimicrobial Agents, 2000, pp. 203-207, vol. 14.

Database PubChemCompound, "N-[4-methoxy-3-(3-phenothiazin-10-yl)propylsulfamoyl)phenyl]acetamide," URL: http://pubchem.ncbi.nlm.nih.gov/search/search.cgi, 2005-2009.

International Search Report for PCT/US2015/019764 dated May 8, 2015.

International Search Report for PCT/US2016/050685 dated Oct. 18, 2016.

International Search Report for PCT/US2016/050688 dated Oct. 18, 2016.

International Search Report for PCT/US2016/045779 dated Sep. 30, 2016.

International Search Report for PCT/US2016/050690 dated Oct. 18, 2016.

International Search Report for PCT/US2016/050696 dated Oct. 18, 2016.

International Search Report for PCT/US2016/050692 dated Oct. 18, 2016.

O'Brien et al., "cis- and trans-Stereoselective Epoxidation of N-protected 2-Cyclohexen-l-ylamines," Organic Letters, 2003, 14(23), 6012-6015.

Zhang et al., "Akt, FoxO and regulation of apoptosis" Biochimica et Biophysica Acta, 2011, vol. 1813, pp. 1978-1986.

Seidlova et al. "Neurotropic and psychotropic substances. XIII. Contributions to the synthesis of amitriptyline, nortriptyline and related substances," Protein Enginee, Oxford University Press, Surrey, GB, vol. 32, No. 8, Jan. 1, 1967, pp. 2826-2839. (In German).

HETEROCYCLIC CONSTRAINED TRICYCLIC SULFONAMIDES AS ANTI-CANCER AGENTS

CROSS REFERENCE TO RELATED APPLICATIONS

This application is a U.S. National Phase filing under 35 U.S.C. § 371 of International Application PCT/US2016/050685, filed Sep. 8, 2016, and published as WO 2017/044567 on Mar. 16, 2017. PCT/US2016/050685 claims priority of U.S. provisional application 62/216,168, filed Sep. 9, 2015. The entire contents of each of the prior applications are incorporated herein by reference.

FIELD OF THE INVENTION

The invention relates to the use of tricyclic chemical modulators of PP2A, comprising heterocyclic constrained tricyclic sulfonamides to treat diseases such as cancer, neurodegenerative disease and other disorders.

BACKGROUND

The FOXO (Forkhead transcription factors, Class O) proteins are a group of transcription factors involved in control of a variety of physiological, metabolic and developmental pathways. They are downstream effectors in a number of signaling pathways including insulin and growth factor signaling; they are also regulated by oxidative stress and nutrient deprivation. Cellular processes affected by FOXO activity include cell cycle control, differentiation, proliferation and apoptosis. Disregulation of FOXO mediated processes has been implicated in a number of pathologies including tumorigenesis, inflammation, diabetes and neurodegenerative conditions amongst others. Activity of FOXO transcription factors are controlled in part by their sub-cellular localization, in particular their localization to the nucleus from the cytosol, and their subsequent transcriptional activation.

Four FOXO proteins designated FOXO1, FOXO3a, FOXO4 and FOXO6 are present in human cells and their activity is controlled by a variety of mechanisms including stability (proteolytic cleavage), sub-cellular localization and transcriptional activation. Activity of the first three members of the family is controlled by cytosolic-nuclear translocation.

FOXO1 regulates expression of a number of genes that play critical roles in cell cycle and apoptosis. A pivotal regulatory mechanism of FOXO is reversible phosphorylation, catalyzed by kinases and phosphatases. Phosphorylation of FOXO1 is associated with 14-3-3 binding and cytosolic localization, whereas dephosphorylated FOXO1 translocates to the nucleus and is transcriptionally active.

Protein phosphatase 2A is one of the four major serine threonine phosphatases and is implicated in the negative control of cell growth and division. Protein phosphatase 2A holoenzymes are heterotrimeric proteins composed of a structural subunit A, a catalytic subunit C, and a regulatory subunit B. The PP2A heterotrimeric protein phosphatase is a ubiquitous and conserved phosphatase with broad substrate specificity and diverse cellular functions. Among the targets of PP2A are proteins of oncogenic signaling cascades, such as Raf, MEK, and AKT.

PP2A interacts directly with FOXO1 and dephosphorylates FOXO1. Inhibition of PP2A phosphatases rescues FOXO-mediated cell death by regulating the level of the pro-apoptotic protein BIM. In addition, PP2A directly regulates FOXO3a subcellular localization and transcriptional activation. Without wishing to be held to any particular theory, it may be that the compounds described herein promote apoptosis by acting on FOXO transcription factors via activation of PP2A.

Myc proteins (c-myc, Mycn and Mycl) target proliferative and apoptotic pathways vital for progression in cancer and it is overexpressed and deregulated in many human cancers. The control of Myc abundance through protein degradation has attracted considerable interest and Ser-62 phosphorylation by a number of kinases has been shown to stabilize the protein. PP2A is responsible for Ser-62 dephophorylation which primes the protein for ubiquitylation and degradation, thus PP2A functions as a negative regulator of Myc.

Prostate cancer is the second leading cause of cancer death in men in America, behind lung cancer. According to the American Cancer Society, approximately 1 man in 36 will die of prostate cancer. Male hormones, specifically testosterone, fuel the growth of prostate cancer. By reducing the amount and activity of testosterone, the growth of advanced prostate cancer is slowed. Endocrine therapy, known as androgen ablation, is the first line of treatment for metastatic prostate cancer. Androgen deprivation therapy for metastatic prostate cancer results in tumor regression and symptomatic improvement in the majority of patients. However, metastatic prostate cancer inevitably progresses despite castrate levels of serum testosterone. Several new therapies have been approved for patients with castration-resistant prostate cancer (CRPC); however, none are curative and tumors ultimately develop resistance. To combat CRPC new approaches and novel therapies are required.

Breast cancer can affect both men and women. Breast cancer is the most prevalent cancer in women, after skin cancers, with about 1 in every 8 women expected to develop invasive breast cancer at some point. One subset of breast cancer expresses the androgen receptor (AR), which has been implicated as a therapeutic target in that subset. About 10-20% of breast cancers—more than one out of every 10—are found to be triple-negative. "Triple negative breast cancer" refers to a breast cancer that does not contain estrogen receptors, progesterone receptors, or human epidermal growth factor receptor 2 (HER2). This means that the growth of the cancer is not supported by the hormones estrogen and progesterone, nor by the presence of too many HER2 receptors. Therefore, triple-negative breast cancer does not respond to hormonal therapy (such as tamoxifen or aromatase inhibitors) or therapies that target HER2 receptors, such as Herceptin (chemical name: trastuzumab). While these tumors are often treatable, the chemotherapy is not targeted, and response durations are short. For doctors and researchers, there is intense interest in finding new medications that can treat breast cancer.

The compounds described herein exhibit anti-proliferative effects and are useful as monotherapy in cancer treatment. Additionally, they can be used in combination with other drugs to restore sensitivity to chemotherapy where resistance has developed.

SUMMARY OF THE INVENTION

A genus of heterocyclic constrained tricyclic arylsulfonamide derivatives has now been found that induce FOXO1 transcription factor translocation to the nucleus by modulating PP2A. The compounds described herein exhibit anti-proliferative effects, and are useful in the treatment of a variety of disorders, including as a monotherapy in cancer treatment, or used in combination with other drugs to restore sensitivity to chemotherapy where resistance has developed.

In a first aspect the invention relates to compounds of formula (1):

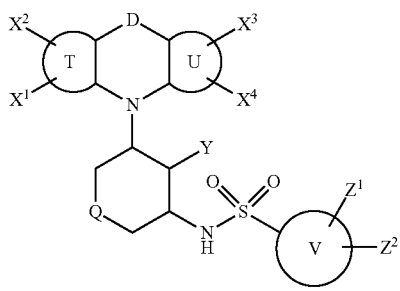

wherein:

D is selected from —S—, —(CH$_2$CH$_2$)—, and —CH═CH—;

T is a benzene ring or a five- or six-membered heteroaromatic ring;

U is a benzene ring or a five- or six-membered heteroaromatic ring;

$X^1$, $X^2$, $X^3$, and $X^4$ are independently selected in each instance from hydrogen, halogen, nitro, cyano, (C$_1$-C$_6$)alkyl, (C$_1$-C$_6$)haloalkyl, (C$_1$-C$_6$)haloalkoxy, (C$_1$-C$_6$)haloalkylthio, —NR$^1$R$^2$, —OR$^1$, —C(O)R$^1$, —OC(O)R$^1$, —C(O)NR$^1$R$^2$, —C(O)OR$^1$, —SR$^1$, —SO$_2$R$^1$, and —SO$_2$NR$^1$R$^2$;

$R^1$ and $R^2$ are independently selected in each instance from the group consisting of hydrogen and (C$_1$-C$_6$)alkyl;

Q is selected from —O—, S(O)$_n$—, and —NR—;

n is zero, 1 or 2;

R is selected from hydrogen; optionally substituted (C$_1$-C$_6$)alkyl, (C$_3$-C$_7$)cycloalkyl, aryl, or heteroaryl; —SO$_2$R$^3$; —SO$_2$NR$^3$R$^4$; —C(═O)R$^5$; —C(═O)OR$^5$; or —C(═O)NR$^3$R$^4$; wherein said substituents on the (C$_1$-C$_6$)alkyl, (C$_3$-C$_7$)cycloalkyl, aryl, or heteroaryl are selected from the group consisting of hydroxy, halogen, cyano, nitro, amino, (C$_1$-C$_4$)alkylamino, (C$_1$-C$_4$)dialkylamino, (C$_1$-C$_4$)acylamino, (C$_1$-C$_4$)alkylsulfonyl, (C$_1$-C$_4$)alkylthio, (C$_1$-C$_4$)alkyl, (C$_3$-C$_7$)cycloalkyl, (C$_1$-C$_4$)haloalkyl, (C$_1$-C$_4$)haloalkoxy, and (C$_1$-C$_4$)alkoxy;

$R^3$ and $R^4$ are independently selected in each instance from hydrogen, (C$_1$-C$_6$)alkyl, aryl, and arylalkyl, wherein said aryl or the aryl of the arylalkyl is optionally substituted with hydroxy, halogen, cyano, nitro, amino, (C$_1$-C$_4$)alkylamino, (C$_1$-C$_4$)dialkylamino, (C$_1$-C$_4$)acylamino, (C$_1$-C$_4$)alkylsulfonyl, (C$_1$-C$_4$)alkylthio, (C$_1$-C$_4$)alkyl, (C$_1$-C$_4$)haloalkyl, (C$_1$-C$_4$)haloalkoxy, or (C$_1$-C$_4$)alkoxy;

$R^5$ is selected from hydrogen, optionally substituted (C$_1$-C$_4$)alkyl, or optionally substituted aryl, wherein said optional substituents are selected from the group consisting of (C$_1$-C$_3$)alkyl, OR$^1$, NH$_2$, NHMe, N(Me)$_2$, and heterocycle;

Y is selected from hydrogen or hydroxyl;

V is selected from phenyl, a six-membered heteroaromatic ring, furan, and thiophene;

$Z^1$ and $Z^2$ are independently selected in each instance from hydrogen, halogen, nitro, cyano, azide, (C$_1$-C$_6$)alkyl, (C$_1$-C$_6$)haloalkyl, (C$_1$-C$_6$)haloalkoxy, —NR$^1$R$^2$, —NR$^1$C(O)R$^2$, —NR$^1$C(O)OR$^6$, —OR$^1$, —C(O)R$^1$, —OC(O)R$^1$, —C(O)NR$^1$R$^2$, —C(O)OR$^1$, —SR$^1$, —SO$_2$R$^1$, and —SO$_2$NR$^1$R$^2$; and $R^6$ is (C$_1$-C$_8$)hydrocarbon.

In a second aspect, the invention relates to methods and uses of the above-described compounds in medicine, particularly for the treatment of a disease chosen from (a) cancer; (b) diabetes; (c) autoimmune disease; (d) age onset proteotoxic disease; (e) mood disorder; (f) acne vulgaris; (g) solid organ transplant rejection; (h) graft vs. host disease; i) cardiac hypertrophy; j) viral infection; and (k) parasitic infection. These methods include administering to a patient a therapeutically effective amount of a compound described herein.

In a third aspect, the invention relates to a method for restoring sensitivity to one or more chemotherapeutic agents in the treatment of cancer. The method includes administering an effective amount of a compound described herein.

In a fourth aspect, the invention relates to a method for treating a disease or disorder in a patient where the disease or disorder involves the dysregulation of PP2A influenced signaling cascades such as the PI3K-AKT, MAP kinase and mTOR pathways. These methods include administering to a patient a therapeutically effective amount of a compound described herein.

In a fifth aspect, the invention relates to a method for treating a disease or disorder in a patient where the disease or disorder involves the dysregulation of a Myc dependent signaling pathway. These methods include administering to a patient a therapeutically effective amount of a compound described herein.

In a sixth aspect, the invention relates to pharmaceutical compositions comprising the compounds described herein.

DETAILED DESCRIPTION OF THE INVENTION

Substituents are generally defined when introduced and retain that definition throughout the specification and in all independent claims.

In a composition aspect, the invention relates to compounds of formula I:

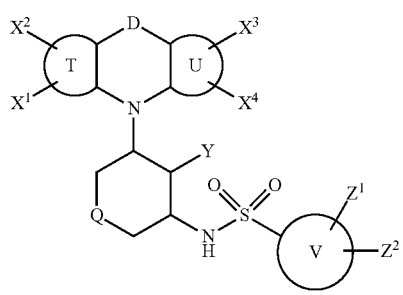

as described above.

In some embodiments, the invention relates to compounds of formula IIa or IIb:

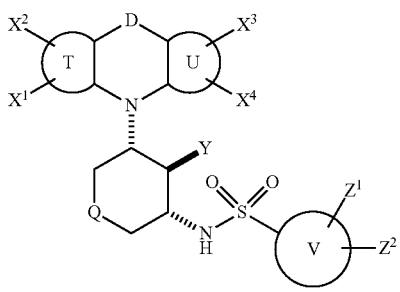

IIa

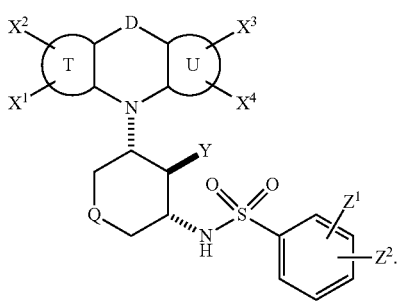

IIb

In some embodiments, the invention relates to compounds of formula IIIa, IIIb, IIIc or IIId:

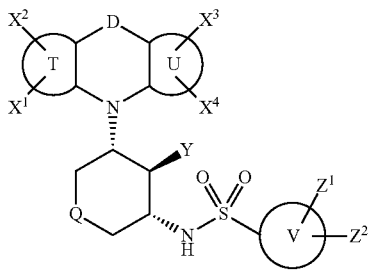

IIIa

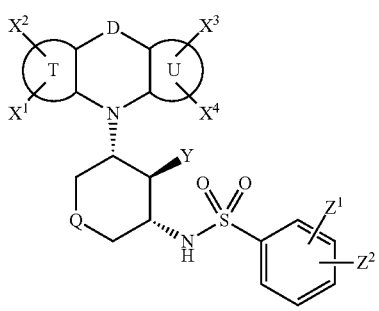

IIIb

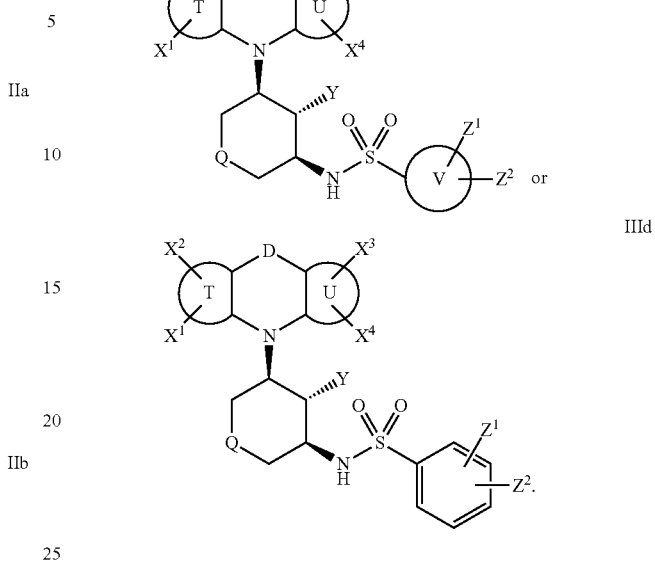

In the embodiments described below, the compound may be of formula I, IIa, IIb, IIIa, IIIb, IIIc, or IId, unless otherwise indicated.

In some embodiments, D is —S—. In other embodiments, D is —(CH$_2$CH$_2$)—. In still other embodiments, D is —CH=CH—.

In some embodiments, T is a benzene ring. In other embodiments, T is a five-membered heteroaromatic ring. In still other embodiments, T is a six-membered heteroaromatic ring.

In some embodiments, U is a benzene ring. In other embodiments, U is a five-membered heteroaromatic ring. In still other embodiments, U is a six-membered heteroaromatic ring.

In some embodiments, T and U are each independently selected from the group consisting of a benzene ring, furan, imidazole, isothiazole, isoxazole, oxadiazole, oxazole, pyran, pyrazine, pyrazole, pyridazine, pyridine, pyrimidine, pyrrole, thiadiazole, thiazine, thiazole, thiophene, triazine, and triazole. In some embodiments, T and U are each independently selected from a benzene ring, pyridine, pyrimidine, pyridazine, thiophene, thiazole, oxazole, imidazole, pyrrole, and furan. In some embodiments, one of T and U is a benzene ring, and the other of T and U is selected from pyridine, pyrimidine, and thiophene. In still other embodiments, T and U are each independently selected from a benzene ring and pyridine. In some embodiments, at least one of T and U is a benzene rings. In other embodiments, T and U are both benzene rings.

In some embodiments, Y is hydroxyl. In other embodiments, Y is hydrogen.

In some embodiments, V is phenyl. In other embodiments, V is thiophene. In still other embodiments, V is furan. In yet other embodiments, V is a six-membered heteroaromatic ring. For instance, V may be pyridine, pyrimidine, or pyridazine.

In some embodiments, Q is —O—. In other embodiments, Q is —S—. In other embodiments, Q is —S(O)—. In other embodiments, Q is —S(O)$_2$—. In still other embodiments, Q is —NR—.

In some embodiments, R is hydrogen. In other embodiments, R is optionally substituted $(C_1-C_6)$alkyl. In still other embodiments, R is optionally substituted $(C_3-C_7)$cycloalkyl. In yet other embodiments, R is optionally substituted aryl. In further embodiments, R is optionally substituted heteroaryl. In these instances, the optional substituents available for the $(C_1-C_6)$alkyl, $(C_3-C_7)$cycloalkyl, aryl or heteroaryl may be one or more of hydroxy, halogen, cyano, nitro, amino, $(C_1-C_4)$alkylamino, $(C_1-C_4)$dialkylamino, $(C_1-C_4)$acylamino, $(C_1-C_4)$alkylsulfonyl, $(C_1-C_4)$alkylthio, $(C_1-C_4)$alkyl, $(C_3-C_7)$cycloalkyl, $(C_1-C_4)$haloalkyl, $(C_1-C_4)$haloalkoxy, and $(C_1-C_4)$alkoxy. In some embodiments, R is $(C_1-C_6)$alkyl optionally substituted with one or more of hydroxy, fluoro, or $(C_3-C_7)$cycloalkyl. In other embodiments, R is $(C_1-C_3)$alkyl optionally substituted with one or more of hydroxy or fluoro. In yet other embodiments, R is $(C_3-C_7)$cycloalkyl optionally substituted with one or more of hydroxy, methyl, or fluoro. In still other embodiments, R is aryl optionally substituted with one or more of hydroxy, methoxy, halogen, $(C_1-C_3)$haloalkyl, nitro, amino, or methyl. In further embodiments, R is phenyl optionally substituted with one or more of hydroxy, chloro, fluoro, methoxy, nitro, amino, trifluoromethyl, or methyl. In yet other embodiments, R is heteroaryl optionally substituted with one or more of hydroxy, methoxy, halogen, $(C_1-C_3)$haloalkyl, nitro, amino, or methyl. In some embodiments, R is a nitrogen-containing heteroaryl optionally substituted with one or two methyl groups. In some embodiments, R is $-SO_2R^3$. In other embodiments, R is $-SO_2NR^3R^4$. In still other embodiments, R is $-C(=O)R^5$. In some embodiments, R is $-C(=O)OR^5$. In yet other embodiments, R is $-C(=O)NR^3R^4$.

In some embodiments, $R^3$ and $R^4$ are independently selected in each instance from hydrogen, $(C_1-C_6)$alkyl, aryl, and arylalkyl. In some embodiments, the aryl or the aryl of the arylalkyl may be optionally substituted with hydroxy, halogen, cyano, nitro, amino, $(C_1-C_4)$alkylamino, $(C_1-C_4)$dialkylamino, $(C_1-C_4)$acylamino, $(C_1-C_4)$alkylsulfonyl, $(C_1-C_4)$alkylthio, $(C_1-C_4)$alkyl, $(C_1-C_4)$haloalkyl, $(C_1-C_4)$haloalkoxy, or $(C_1-C_4)$alkoxy. In some embodiments, $R^4$ is selected from hydrogen and methyl. In other embodiments, $R^3$ is selected from hydrogen, $(C_1-C_6)$alkyl, $(C_1-C_6)$haloalkyl, aryl, and arylalkyl. In some of these embodiments, the aryl or the aryl of the arylalkyl is optionally substituted with one or more of hydroxy, halogen, cyano, nitro, amino, $(C_1-C_4)$alkylamino, $(C_1-C_4)$dialkylamino, $(C_1-C_4)$acylamino, $(C_1-C_4)$alkylsulfonyl, $(C_1-C_4)$alkylthio, $(C_1-C_4)$alkyl, $(C_1-C_4)$haloalkyl, $(C_1-C_4)$haloalkoxy, and $(C_1-C_4)$alkoxy.

In some embodiments, $R^5$ is selected from hydrogen, optionally substituted $(C_1-C_4)$alkyl, or optionally substituted aryl. In some embodiments, the optional substituents are selected from $(C_1-C_3)$alkyl, $OR^1$, $NH_2$, $NHMe$, $N(Me)_2$, and heterocycle. In other embodiments, $R^5$ is selected from optionally substituted $(C_1-C_4)$alkyl or optionally substituted aryl, and the optional substituents are selected from one or more of OH, OMe, $NH_2$, NHMe, $N(Me)_2$, or heterocycle.

In some embodiments, R is $-C(=O)R^5$ and $R^5$ is selected from methyl, optionally substituted with $OR^1$, $NH_2$, NHMe, $N(Me)_2$, and heterocycle. In other embodiments, R is $-C(=O)OR^5$ and $R^5$ is selected from the group consisting of phenyl and $(C_1-C_4)$alkyl, each of which may be substituted with $OR^1$; in some of these embodiments, $R^1$ is hydrogen, while in other of these embodiments, $R^1$ is $(C_1-C_6)$alkyl. In still other embodiments, R is $-SO_2R^3$ and $R^3$ is selected from hydrogen, $(C_1-C_6)$alkyl, and aryl. In some of these embodiments, the aryl may be substituted with hydroxy, halogen, cyano, amino, or $(C_1-C_4)$alkoxy. In yet other embodiments, R is $SO_2NR^3R^4$; $R^3$ is selected from hydrogen, $(C_1-C_3)$alkyl, and optionally substituted aryl; and $R^4$ is hydrogen or methyl. In further embodiments, R is $-C(=O)NR^3R^4$; $R^3$ is selected from hydrogen, $(C_1-C_3)$alkyl, and aryl optionally substituted with hydroxy, halogen, cyano, amino, or methoxy; and $R^4$ is hydrogen or methyl.

In some embodiments, $X^1$, $X^2$, $X^3$, and $X^4$ are independently selected in each instance from hydrogen, halogen, nitro, cyano, $(C_1-C_6)$alkyl, $(C_1-C_6)$haloalkyl, $(C_1-C_6)$haloalkoxy, $(C_1-C_6)$haloalkylthio, $-NR^1R^2$, $-OR^1$, $-C(O)R^1$, $-OC(O)R^1$, $-C(O)NR^1R^2$, $-C(O)OR^1$, $-SR^1$, $-SO_2R^1$, and $-SO_2NR^1R^2$. In some embodiments, zero, one or two of $X^1$, $X^2$, $X^3$, and $X^4$ are independently selected in each instance from halogen and $(C_1-C_6)$haloalkyl, and the remainder are hydrogen. In other embodiments, one or two of $X^1$, $X^2$, $X^3$, and $X^4$ are independently selected in each instance from chloro, fluoro, and $(C_1-C_3)$fluoroalkyl, and the remainder are hydrogen.

In some embodiments, $R^1$ is hydrogen. In other embodiments, $R^1$ is $(C_1-C_6)$alkyl. In some embodiments, $R^2$ is hydrogen. In other embodiments, $R^2$ is $(C_1-C_6)$alkyl.

In some embodiments, $Z^1$ is selected from hydrogen, halogen, nitro, cyano, azide, $(C_1-C_6)$alkyl, $(C_1-C_6)$haloalkyl, $(C_1-C_6)$haloalkoxy, $-NR^1R^2$, $-NR^1C(O)R^2$, $-NR^1C(O)OR^6$, $-OR^1$, $-C(O)R^1$, $-OC(O)R^1$, $-C(O)NR^1R^2$, $-C(O)OR^1$, $-SR^1$, $-SO_2R^1$, and $-SO_2NR^1R^2$. In some embodiments, $Z^2$ is selected from hydrogen, halogen, nitro, cyano, azide, $(C_1-C_6)$alkyl, $(C_1-C_6)$haloalkyl, $(C_1-C_6)$haloalkoxy, $-NR^1R^2$, $-NR^1C(O)R^2$, $-NR^1C(O)OR^6$, $-OR^1$, $-C(O)R^1$, $-OC(O)R^1$, $-C(O)NR^1R^2$, $-C(O)OR^1$, $-SR^1$, $-SO_2R^1$, and $-SO_2NR^1R^2$. In other embodiments, $Z^1$ and $Z^2$ are independently selected in each instance from hydrogen, halogen, $(C_1-C_6)$haloalkyl, $(C_1-C_6)$alkoxy, and $(C_1-C_6)$haloalkoxy. In some embodiments, $Z^1$ is hydrogen and $Z^2$ is selected from hydrogen, halogen, $(C_1-C_6)$haloalkyl, $(C_1-C_6)$alkoxy, $(C_1-C_6)$haloalkoxy, and NHBoc. In some embodiments, $Z^1$ is hydrogen and $Z^2$ is hydrogen, fluoro, chloro, trifluoromethyl, methoxy, trifluoromethoxy, or NHBoc. In other embodiments, $Z^2$ is para to the attachment of the phenyl ring to the sulfonyl.

In some embodiments, $R^6$ is $(C_1-C_8)$hydrocarbon. In other embodiments, $R^6$ is $(C_1-C_6)$alkyl. In some embodiments, $R^6$ is t-butyl. In still other embodiments, $R^6$ is allyl. In yet other embodiments, $R^6$ is benzyl.

The person of skill will understand that, in some instances, $R^1$, $R^2$, $R^3$, $R^4$, and $R^5$ may not be hydrogen. For instance, when Q is NR, R is $-SO_2R^3$, and $R^3$ is hydrogen, the resulting moiety will be unstable. The circumstances under which a hydrogen atom would be inappropriate will be clear to the person of skill in the art.

In some embodiments, B is $-CH_2CH_2-$, T and U are each phenyl, Y is hydroxyl, Q is NR, and the compound is of one of the formulae below

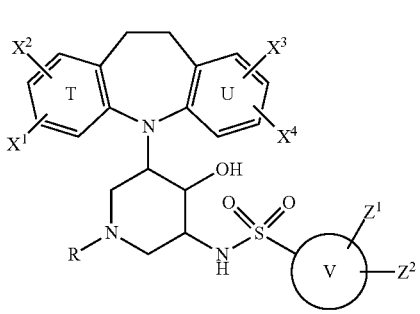

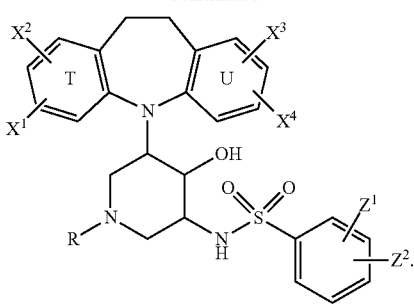

In some embodiments, B is —CH$_2$CH$_2$—, T and U are each phenyl, Y is hydroxyl, Q is —O—, and the compound is of one of the formulae below

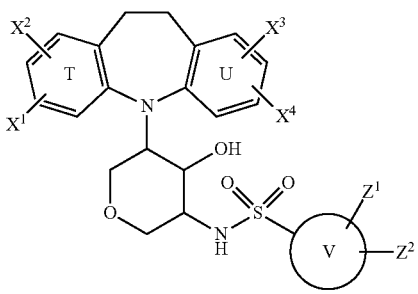

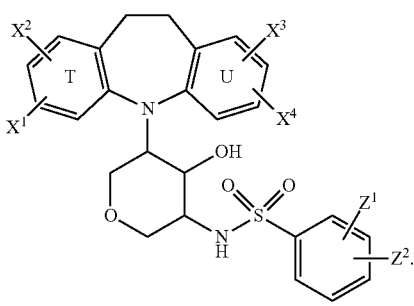

In some embodiments, B is —S—, T and U are each phenyl, Y is hydroxyl, Q is —O—, and the compound is of one of the formulae below

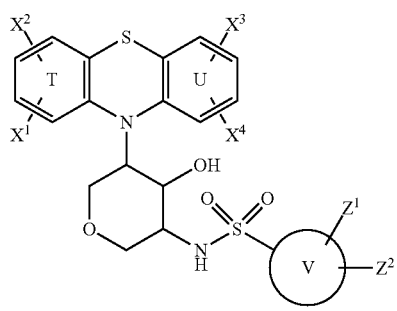

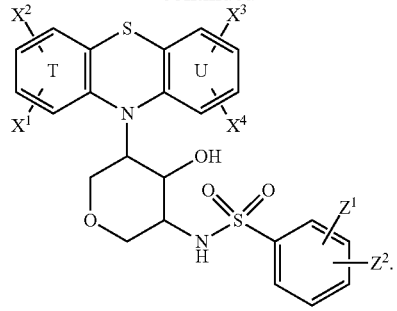

In some embodiments, B is —S—, T and U are each phenyl, Y is hydroxyl, Q is NR, and the compound is of one of the formulae below

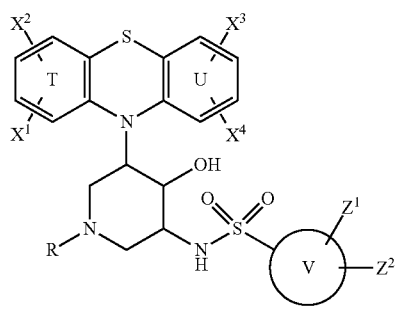

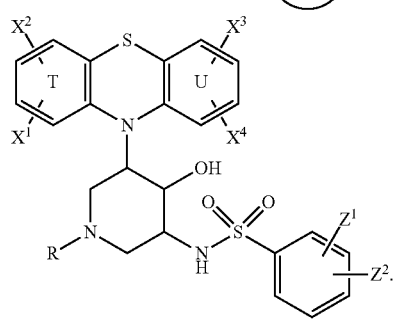

In some embodiments, $Z^1$ is hydrogen and $Z^2$ is selected from hydrogen, halogen, (C$_1$-C$_6$)haloalkyl, —NR$^1$C(O)OR$^6$, (C$_1$-C$_6$)alkoxy, or (C$_1$-C$_6$)haloalkoxy. In other embodiments, $Z^1$ is hydrogen and $Z^2$ is hydrogen, fluoro, chloro, trifluoromethyl, NHBoc, methoxy, or trifluoromethoxy. In still other embodiments, $Z^1$ is hydrogen and $Z^2$ is trifluoromethoxy.

In some embodiments of the foregoing subgenera, the relative configurations are such that the amine and the tricycle are both trans to the alcohol (Y), as shown above in, for instance, formula IIa. In this trans:trans subgroup, compounds can be either single enantiomers, like in formulae IIIa and IIIc, or a mixture of the two. If a mixture, the mixture will most commonly be racemic, but it need not be. Substantially pure single enantiomers of biologically active compounds such as those described herein often exhibit advantages over their racemic mixture.

In summary, the invention relates to:

[1]. A compound of formula I, IIa, IIb, IIIa, IIIb, IIIc, or IIId.

[2]. A compound according to [1] above wherein D is —S—.

[3]. A compound according to [1] above wherein D is —(CH$_2$CH$_2$)—.

[4]. A compound according to [1] above wherein D is —CH═CH—.

[5]. A compound according to any of [1] through [4] above wherein T and U are each independently selected from the group consisting of a benzene ring and pyridine.

[6]. A compound according to any of [1] through [4] above wherein at least one of T and U is a benzene ring.

[7]. A compound according to any of [1] through [4] above wherein both T and U are benzene rings.

[8]. A compound according to any of [1] through [7] above wherein Y is hydroxyl.

[9]. A compound according to any of [1] through [7] above wherein Y is hydrogen.

[10]. A compound according to any of [1] through [9] above wherein Q is —NR—.

[11]. A compound according to any of [1] through [9] above wherein Q is —O—.

[12]. A compound according to any of [1] through [9] above wherein Q is —S(O)$_n$—.

[13]. A compound according to any of [1] through [12] above, wherein zero, one or two of $X^1$, $X^2$, $X^3$, and $X^4$ are independently selected in each instance from halogen and $(C_1-C_6)$haloalkyl, and the remainder are hydrogen.

[14]. A compound according to any of [1] through [13] above, wherein zero, one or two of $X^1$, $X^2$, $X^3$, and $X^4$ are independently selected in each instance from chloro, fluoro, and $(C_1-C_3)$fluoroalkyl, and the remainder are hydrogen.

[15]. A compound according to any of [1] through [14] above, wherein $Z^1$ and $Z^2$ are independently selected in each instance from hydrogen, halogen, $(C_1-C_6)$haloalkyl, —$NR^1C(O)OR^6$, $(C_1-C_6)$alkoxy, and $(C_1-C_6)$haloalkoxy.

[16]. A compound according to any of [1] through [15] above, wherein $Z^1$ is hydrogen and $Z^2$ is selected from hydrogen, halogen, $(C_1-C_6)$haloalkyl, —$NR^1C(O)OR^6$, $(C_1-C_6)$alkoxy, and $(C_1-C_6)$haloalkoxy.

[17]. A compound according to any of [1] through [16] above, wherein $Z^1$ is hydrogen and $Z^2$ is hydrogen, fluoro, chloro, trifluoromethyl, —NHBoc, methoxy, or trifluoromethoxy.

[18]. A compound according to any of [1] through [17] above, wherein V is phenyl.

[19]. A compound according to any of [1] through [18] above, wherein $Z^2$ is para to the attachment of the phenyl ring to the sulfonyl.

The compounds described herein contain three or more asymmetric centers and may thus give rise to enantiomers, diastereomers, and other stereoisomeric forms which may be defined in terms of absolute stereochemistry as (R)- or (S)-. The present invention is meant to include all such possible diastereomers as well as their racemic and optically pure forms. Optically active (R)- and (S)-isomers may be prepared using homo-chiral synthons or homo-chiral reagents, or optically resolved using conventional techniques. When the compounds described herein contain olefinic double bonds or other centers of geometric asymmetry, and unless specified otherwise, it is intended to include both (E)- and (Z)-geometric isomers. Likewise, all tautomeric forms are intended to be included.

The graphic representations of racemic, ambiscalemic and scalemic or enantiomerically pure compounds used herein are a modified version of the denotations taken from Maehr J. Chem. Ed. 62, 114-120 (1985): simple lines provide no information about stereochemistry and convey only connectivity; solid and broken wedges are used to denote the absolute configuration of a chiral element; solid and broken bold lines are geometric descriptors indicating the relative configuration shown but not necessarily denoting racemic character; and wedge outlines and dotted or broken lines denote enantiomerically pure compounds of indeterminate absolute configuration. For example, the graphic representation

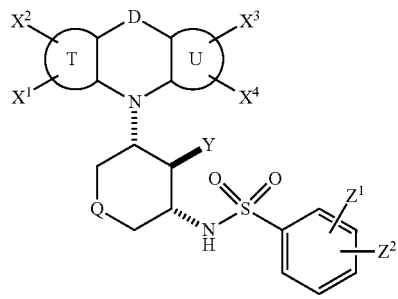

indicates either, or both, of the two trans:trans enantiomers:

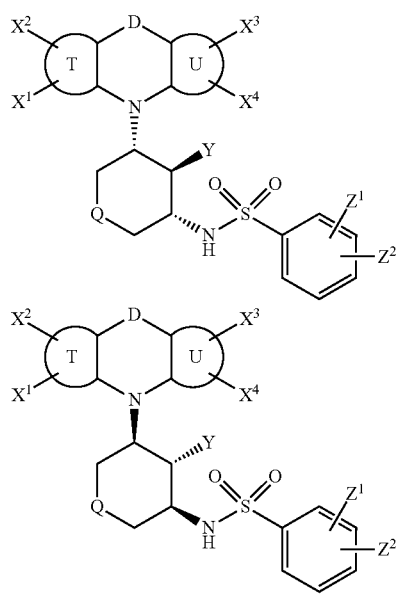

in any ratio, from pure enantiomers to racemates. The graphic representation:

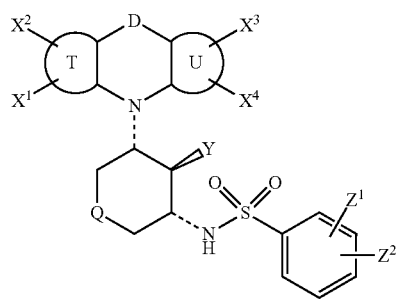

indicates a single enantiomer of unknown absolute stereochemistry, i.e. it could be either of the two preceding structures, as a substantially pure single enantiomer. And, finally, the representation:

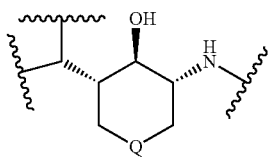

indicates a pure (1R,2R,6S)-2-amino-6-(C-attached tricycle) heterocyclyl-4-ol. For the purpose of the present disclosure, a "pure" or "substantially pure" enantiomer is intended to mean that the enantiomer is at least 95% of the configuration shown and 5% or less of other enantiomers. Similarly, a "pure" or "substantially pure" diastereomer is intended to mean that the diastereomer is at least 95% of the relative configuration shown and 5% or less of other diastereomers. In the text describing the stereochemistry of the examples, the convention of Chemical Abstracts is used. Thus "(1R, 2R,6S)-rel-" indicates that the three chiral centers are in that relative relationship, which would be depicted in a structural diagram by solid bold and dashed lines, whereas "(1R,2R, 6S)" without the "rel" indicates a single enantiomer of that absolute configuration, which would be depicted in a structural diagram by solid and broken wedges.

It may be found upon examination that certain species and genera are not patentable to the inventors in this application. In this case, the exclusion of species and genera in applicants' claims are to be considered artifacts of patent prosecution and not reflective of the inventors' concept or description of their invention, which encompasses all members of the genus I that are not in the public's possession.

As used herein, and as would be understood by the person of skill in the art, the recitation of "a compound"—unless expressly further limited—is intended to include salts of that compound. In a particular embodiment, the term "compound of formula" refers to the compound or a pharmaceutically acceptable salt thereof.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

Also provided herein is a pharmaceutical composition comprising a compound disclosed above, or a pharmaceutically acceptable salt form thereof, and a pharmaceutically acceptable carrier or diluent.

While it may be possible for the compounds of the formulae disclosed herein to be administered as the raw chemical, it is preferable to present them as a pharmaceutical composition. According to a further aspect, the present invention provides a pharmaceutical composition comprising a compound of formula I or a pharmaceutically acceptable salt thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula I or a pharmaceutically acceptable salt thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^{2}H$, $^{3}H$, $^{13}C$, $^{14}C$, $^{15}N$, $^{35}S$, $^{18}F$, and $^{36}Cl$, respectively. Compounds that contain those radioisotopes and/or other radioisotopes of other atoms are within the scope of this invention. Tritiated, i.e. $^{3}H$, and carbon-14, i.e., $^{14}C$, radioisotopes are particularly preferred for their ease in preparation and detectability. Compounds that contain isotopes $^{11}C$, $^{13}N$, $^{15}O$ and $^{18}F$ are well suited for positron emission tomography. Radiolabeled compounds of formula I of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

The compounds provided herein can be used for treating cancer in a patient, the method comprising administering to the patient a therapeutically effective amount of a compound of formula I. In some embodiments, the cancer is characterized by dysregulation of the PI3K-AKT-FOXO signaling pathway. For example, the cancer can be selected from the group consisting of: ovarian, pancreatic, renal cell, breast, prostate, lung, hepatocellular carcinoma, glioma, leukemia, lymphoma, colorectal cancers, and sarcomas.

In some embodiments, the method further comprises administering one or more additional cancer chemotherapeutic agents. In some embodiments, the one or more additional cancer chemotherapeutic agents are EGFR inhibitors.

In some embodiments, the cancer is chemotherapy resistant cancer. In some embodiments, the method further comprises administering one or more cancer chemotherapeutic agents. In some embodiments, the one or more cancer chemotherapeutic agents are EGFR inhibitors.

In some embodiments, administration of a compound of formula I can restore sensitivity to one or more chemotherapeutic agents in a patient wherein the patient has developed a resistance to the one or more chemotherapeutic agents. More particularly, cancers that may be treated by the compounds, compositions and methods described herein include, but are not limited to, the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g., hepatocellular carcinoma; cholangiocarcinoma; hepatoblastoma; angiosarcoma; hepatocellular adenoma; and hemangioma;

bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non Hodgkin's lymphoma (malignant lymphoma) and Waldenström's macroglobulinemia;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

Cancers may be solid tumors that may or may not be metastatic. Cancers may also occur, as in leukemia, as a diffuse tissue.

The compounds described herein can also be administered in combination with existing methods of treating cancers, for example by chemotherapy, irradiation, or surgery. Thus, there is further provided a method of treating cancer comprising administering an effective amount of a compound according to formula I to a patient, wherein a therapeutically effective amount of one or more additional cancer chemotherapeutic agents are administered to the patient.

Also provided herein is a method for treating diabetes in a patient, the method comprising administering to the patient a therapeutically effective amount of a compound of formula I.

Further provided herein is a method for treating an autoimmune disease in a patient, the method comprising administering to the patient a therapeutically effective amount of a compound of formula I. The autoimmune disease can be, for example, inflammatory bowel disease (IBD). Immune responses are constantly and tightly regulated and one important cellular component in maintaining self tolerance (i.e., prevention of autoimmunity) and tolerance of benign commensal gut flora are regulatory T cells (Treg). Treg can be subdivided into multiple phenotypes, but the most common are CD4+CD25+ T cells that express the transcription factor Foxp3. Foxp3 is a direct transcriptional target of FOXO proteins, particularly FOXO1 and FOXO3. Thus activation of FOXO proteins in naïve T-cells promotes and directs differentiation to maintain a population of Treg cells.

Acute immune mediated rejection and chronic immune mediated rejection are key obstacles to successful solid organ transplantation. It is believed that these forms of rejection can be prevented/overcome by amplifying Treg number and or function. Similarly, a common and morbid complication of allogeneic hematopoietic cell transplants (Allo-HCT) used to treat various malignant and non-malignant conditions, is graft versus host disease, in which the transplanted immune cells from the donor damage multiple organs in the recipient (most notably skin, gut, and liver). Increasing experimental and clinical data indicate that Tregs can be harnessed to prevent and/or treat this disease process.

Thus compounds of the present invention are useful in treatment of autoimmune and related diseases, by activating FOXO proteins and inducing T cell differentiation to Tregs. Compounds may be administered therapeutically to subjects directly, or alternatively, T cells may be collected from a subject and differentiated ex vivo to Tregs as described by Taylor et al. [*Blood* 99, 3493-3499 (2002)].

Aspects of the invention include methods for treatment of autoimmune disease characterized by deficiency in Treg function comprising administering a therapeutically useful amount of compound of Formula I. The method can also include extraction of naïve T-cells from a patient, differentiation of T-cells to Tregs ex vivo by treatment with a compound of Formula I, optionally supplemented with an HDACi, followed by administration of Tregs to patient with optional separation of compound of Formula I from Tregs prior to their administration. As stated above, autoimmune diseases that can be so treated include IBD, solid organ transplant rejection, and GvHD in allo-HCT In some embodiments, the compounds can be administered to a patient to treat an autoimmune disorder, for example, Addison's disease, Amyotrophic Lateral Sclerosis, celiac disease, Crohn's disease, diabetes, eosinophilic fasciitis, Guillain-Barré syndrome (GBS), Graves' disease, Lupus erythematosus, Miller-Fisher syndrome, psoriasis, rheumatoid arthritis, ulcerative colitis, and vasculitis. In some embodiments, the compound provided herein can be used for treating a disease or disorder in a patient wherein the disease or disorder involves excessive or unregulated cellular proliferation, the method comprising administering to the patient a therapeutically effective amount of a compound of formula (I). Also provided herein is a method for treating a disease or disorder in a patient where the disease or disorder involves the dysregulation of the pi3K-AKT-FOXO signaling pathway, the method comprising administering to the patient a therapeutically effective amount of a compound of formula I.

Further provided herein is a method for treating a disease in a patient wherein the disease is characterized by proteotoxicity, including age onset proteotoxicity leading to neurodegeneration, the method comprising administering to the patient a therapeutically effective amount of a compound of formula I. Hyperphosphorylated Tau has been implicated as the pathogenic protein in several neurodegenerative diseases and furthermore PP2A has been shown to be an important phosphatase in reversing aberrant phosphorylation of Tau; see for example Ludovic Martin et al., Tau protein phosphatases in Alzheimer's disease: The leading role of PP2A in Ageing Research Reviews 12 (2013) 39-49; Miguel Medina and Jesus Avila, Further understanding of tau phosphorylation: implications for therapy in Expert Rev. Neurotherapy, 15(1), 115-112 (2015) and Michael Voronkov et al., Phosphoprotein phosphatase 2A: a novel druggable target for Alzheimer's disease in Future Med Chem. 2011 May, 3(7) 821-833. Hyperphosphorylated alpha-Synuclein is a second exemplar of a toxic protein, and again PP2A has been shown to reverse its aberrantly phosphorylated state; see for example Kang-Woo Lee et al., Enhanced Phosphatase Activity Attenuates alpha-Synucleinopathy in a Mouse Model in Neurobiology of Disease, May 11, 2011, 31(19) 6963-6971. In some embodiments, the disease is selected from the group consisting of: Alzheimer's disease, Parkinson's disease, Huntington's disease, amyotrophic lateral sclerosis, frontotemporal dementia, progressive supranuclear palsy, corticobasal degeneration and Pick's disease.

The compounds provided herein may further be used in a method for treating a mood disorder in a patient by administering to the patient a therapeutically effective amount of a compound of formula I. In some embodiments, the mood disorder is stress-induced depression.

Also provided herein is a method for treating acne vulgaris in a patient by administering to the patient a therapeutically effective amount of a compound of formula I.

Further provided herein is a method for treating cardiac hypertrophy in a patient by administering to the patient a therapeutically effective amount of a compound of formula I. In some embodiments, the cardiac hypertrophy is associated with a disease selected from hypertension, myocardial infarction, and valvular heart disease.

The compounds provided herein may further be used in a method for treating a viral infection in a patient by administering to the patient a therapeutically effective amount of a compound of formula I. Examples of viruses that may cause viral infections to be treated include, but are not limited to: a polyomavirus, such as John Cunningham Virus (JCV), Simian virus 40 (SV40), or BK Virus (BKV); influenza, Human Immunodeficiency Virus type 1 (HIV-1), Human Papilloma Virus (HPV), adenovirus, Epstein-Barr Virus (EBV), Hepatitis C Virus (HCV), Molluscum contagiosum virus (MCV); Human T-lymphotropic virus type 1 HTLV-1), Herpes Simplex Virus type 1 (HSV-1), cytomegalovirus (CMV), hepatitis B virus, Bovine papillomavirus (BPV-1), human T-cell lymphotropic virus type 1, Japanese encephalitis virus, respiratory syncytial virus (RSV), and West Nile virus.

Further provided herein is a method for treating a parasitic infection in a patient by administering to the patient a therapeutically effective amount of a compound of formula I. Examples of parasites that may cause parasitic infections to be treated include, but are not limited to, *Plasmodium* and *Theileria*.

PP2A enzymes are involved in the regulation of cell transcription, cell cycle, and viral transformation. Many viruses, including cytomegalovirus, parainfluenza, DNA tumor viruses, and HIV-1, utilize different approaches to exploit PPA2 in order to modify, control, or inactivate cellular activities of the host [Garcia et al., Microbes and Infection, 2, 2000, 401-407]. Therefore, the compounds provided herein may further be used in a method for treating a viral infection in a patient by administering to the patient a therapeutically effective amount of a compound of formula (I). Examples of viruses that may cause viral infections to be treated include, but are not limited to: a polyomavirus, such as John Cunningham Virus (JCV), Simian virus 40 (SV40), or BK Virus (BKV); influenza, Human Immunodeficiency Virus type 1 (HIV-1), Human Papilloma Virus (HPV), adenovirus, Epstein-Barr Virus (EBV), Hepatitis C Virus (HCV), Molluscum contagiosum virus (MCV); Human T-lymphotropic virus type 1 HTLV-1), Herpes Simplex Virus type 1 (HSV-1), cytomegalovirus (CMV), hepatitis B virus, Bovine papillomavirus (BPV-1), human T-cell lymphotropic virus type 1, Japanese encephalitis virus, respiratory syncytial virus (RSV), and West Nile virus.

Serine/Threonine phosphatases, including PP2A are involved in modulation of synaptic plasticity (D. G. Winder and J. D. Sweatt, Nature Reviews Neuroscience, vol 2, July 2001, pages 461-474). Persistently decreased PP2A activity is associated with maintenance of Long Term Potentiation (LTP) of synapses, thus treatment PP2A activators such as those described here may reverse synaptic LTP. Psychostimulant drugs of abuse such as cocaine and methamphetamine are associated with deleterious synaptic LTP (L. Mao et al, Neuron 67, Sep. 9, 2010 and A. Stipanovich et al, Nature vol 453, 2008, pages 879-884), which may underlie the pathology of addiction and relapse therefore PP2A activators described here may be useful as treatments for psychostimulant abuse.

Abnormalities in synaptic structure and signaling are linked to autistic spectrum disorder, see for example, Y Chen et al., CTTNBP2, but not CTTNBP2NL, regulates dendritic spinogenesis and synaptic distribution of the striatin-PP2A complex, Molecular Biology of the Cell, 23, Nov. 15, 2012, 4383-4392. PP2A has been shown to be important in normal development of dendritic spines, and treatment with compounds of the present invention may ameliorate or reverse autistic spectrum disorder.

Abbreviations and Definitions

Unless defined otherwise, all technical and scientific terms used herein have the same meaning as is commonly understood by one of ordinary skill in the art to which this disclosure belongs. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference. In the event that there is a plurality of definitions for terms cited herein, those in this section prevail unless otherwise stated.

The following abbreviations and terms have the indicated meanings throughout:

Ac=acetyl
Aq=aqueous
Boc=t-butyloxy carbonyl
Bu=butyl
c-=cyclo
DBA=dibenzylideneacetone
DCM=dichloromethane=methylene chloride=$CH_2Cl_2$
DMF=N,N-dimethylformamide
eq. or equiv.=equivalent(s)
Et=ethyl
GC=gas chromatography
h=hour(s)
KHMDS=Potassium bis(trimethylsilyl)amide
mCPBA=meta-Chloroperoxybenzoic acid
Me=methyl
mesyl=methanesulfonyl
min.=minute(s)
NMO or NMMO=N-methylmorpholine oxide
Pg=protecting group
Ph=phenyl
RT=room temperature
sat'd or sat.=saturated
t- or tert=tertiary
TFA=trifluoroacetic acid
THF=tetrahydrofuran
tosyl=p-toluenesulfonyl As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof, but only if the additional features, integers, steps, components or groups thereof do not materially alter the basic and novel characteristics of the claimed composition or method.

A "patient," as used herein, includes both humans and other animals, particularly mammals. Thus the methods are applicable to both human therapy and veterinary applications. In some embodiments, the patient is a mammal, for example, a primate. In some embodiments, the patient is a human.

Treatment can involve administering a compound described herein to a patient diagnosed with a disease, and may involve administering the compound to a patient who does not have active symptoms. Conversely, treatment may involve administering the compositions to a patient at risk of developing a particular disease, or to a patient reporting one or more of the physiological symptoms of a disease, even though a diagnosis of this disease may not have been made.

The terms "administer", "administering" or "administration" in reference to a dosage form of the invention refers to the act of introducing the dosage form into the system of subject in need of treatment. When a dosage form of the invention is given in combination with one or more other active agents (in their respective dosage forms), "administration" and its variants are each understood to include concurrent and/or sequential introduction of the dosage form and the other active agents. Administration of any of the described dosage forms includes parallel administration, co-administration or sequential administration. In some situations, the therapies are administered at approximately the same time, e.g., within about a few seconds to a few hours of one another.

A "therapeutically effective" amount of the compounds described herein is typically one which is sufficient to achieve the desired effect and may vary according to the nature and severity of the disease condition, and the potency of the compound. It will be appreciated that different concentrations may be employed for prophylaxis than for treatment of an active disease. A therapeutic benefit is achieved with the amelioration of one or more of the physiological symptoms associated with the underlying disorder such that an improvement is observed in the patient, notwithstanding that the patient may still be afflicted with the underlying disorder.

The term "modulate" with respect to a FOXO transcription factor protein refers to activation of the FOXO transcription factor protein and its biological activities associated with the FOXO pathway. Modulation of FOXO transcription factor proteins includes up-regulation (i.e., agonizing, activation or stimulation). The mode of action of a FOXO modulator can be direct, e.g., through binding to the FOXO transcription factor protein as a ligand. The modulation can also be indirect, e.g., through binding to and/or modifying another molecule which otherwise binds to and activates the FOXO transcription factor protein.

Throughout this specification the terms and substituents retain their definitions.

$C_1$ to $C_{20}$ hydrocarbon includes alkyl, cycloalkyl, polycycloalkyl, alkenyl, alkynyl, aryl and combinations thereof. Examples include benzyl, phenethyl, cyclohexylmethyl, adamantyl, camphoryl and naphthylethyl. Hydrocarbyl refers to any substituent comprised of hydrogen and carbon as the only elemental constituents. Aliphatic hydrocarbons are hydrocarbons that are not aromatic; they may be saturated or unsaturated, cyclic, linear or branched. Examples of aliphatic hydrocarbons include isopropyl, 2-butenyl, 2-butynyl, cyclopentyl, norbornyl, etc. Aromatic hydrocarbons include benzene (phenyl), naphthalene (naphthyl), anthracene, etc.

Unless otherwise specified, alkyl (or alkylene) is intended to include linear or branched saturated hydrocarbon structures and combinations thereof. Alkyl refers to alkyl groups from 1 to 20 carbon atoms, preferably 1 to 10 carbon atoms, more preferably 1 to 6 carbon atoms. Examples of alkyl groups include methyl, ethyl, propyl, isopropyl, n-butyl, s-butyl, t-butyl and the like.

Cycloalkyl is a subset of hydrocarbon and includes cyclic hydrocarbon groups of from 3 to 8 carbon atoms. Examples of cycloalkyl groups include cy-propyl, cy-butyl, cy-pentyl, norbornyl and the like.

Unless otherwise specified, the term "carbocycle" is intended to include ring systems in which the ring atoms are all carbon but of any oxidation state. Thus ($C_3$-$C_{10}$) carbocycle refers to both non-aromatic and aromatic systems, including such systems as cyclopropane, benzene and cyclohexene; ($C_8$-$C_{12}$) carbopolycycle refers to such systems as norbornane, decalin, indane and naphthalene. Carbocycle, if not otherwise limited, refers to monocycles, bicycles and polycycles.

Heterocycle means an aliphatic or aromatic carbocycle residue in which from one to four carbons is replaced by a heteroatom selected from the group consisting of N, O, and S. The nitrogen and sulfur heteroatoms may optionally be oxidized, and the nitrogen heteroatom may optionally be quaternized. Unless otherwise specified, a heterocycle may be non-aromatic (heteroaliphatic) or aromatic (heteroaryl). Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. Examples of heterocyclyl residues include piperazinyl, piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl (also historically called thiophenyl), benzothienyl, thiamorpholinyl, oxadiazolyl, triazolyl and tetrahydroquinolinyl.

Alkoxy or alkoxyl refers to groups of from 1 to 20 carbon atoms, preferably 1 to 10 carbon atoms, more preferably 1 to 6 carbon atoms of a straight or branched configuration attached to the parent structure through an oxygen. Examples include methoxy, ethoxy, propoxy, isopropoxy and the like. Lower-alkoxy refers to groups containing one to four carbons. For the purpose of this application, alkoxy and lower alkoxy include methylenedioxy and ethylenedioxy.

The term "halogen" means fluorine, chlorine, bromine or iodine atoms. In one embodiment, halogen may be a fluorine or chlorine atom.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. Examples include acetyl, benzoyl, propionyl, isobutyryl and the like. Lower-acyl refers to groups containing one to four carbons. The double bonded oxygen, when referred to as a substituent itself is called "oxo".

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, alkyl, acyl, alkoxyalkyl, hydroxy lower alkyl, carbonyl, phenyl, heteroaryl, benzenesulfonyl, hydroxy, lower alkoxy, haloalkoxy, oxaalkyl, carboxy, alkoxycarbonyl [—C(═O)O-alkyl], alkoxycarbonylamino [HNC(═O)O-alkyl], aminocarbonyl (also known as carboxamido) [—C(═O)NH$_2$], alkylaminocarbonyl [—C(═O)NH-alkyl], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2, or 3 hydrogen atoms are replaced with a specified radical. In the case of alkyl and cycloalkyl, more than three hydrogen atoms can be replaced by fluorine; indeed, all available hydrogen atoms could be replaced by fluorine. In preferred embodiments, substituents are halogen, haloalkyl, alkyl, acyl, hydroxyalkyl, hydroxy, alkoxy, haloalkoxy, aminocarbonyl oxaalkyl, carboxy, cyano, acetoxy, nitro, amino, alkylamino, dialkylamino, alkylthio, alkylsulfinyl, alkylsulfonyl, alkylsulfonylamino arylsulfonyl, arylsulfonylamino, and benzyloxy.

Substituents R″ are generally defined when introduced and retain that definition throughout the specification and in all independent claims.

EXAMPLES

| Compound ID | Structure |
|---|---|
| 1 | 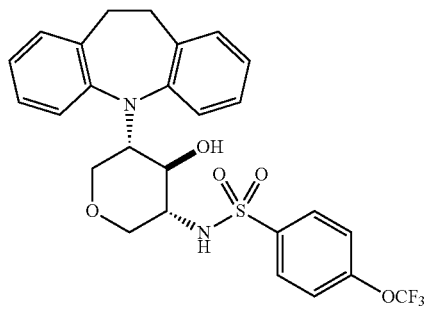 [SMILES: O=S(=O)(N[C@@H]1COC[C@H](N2c3ccccc3CCc3ccccc32)[C@H]1O)c1ccc(OC(F)(F)F)cc1] |
| 1a | 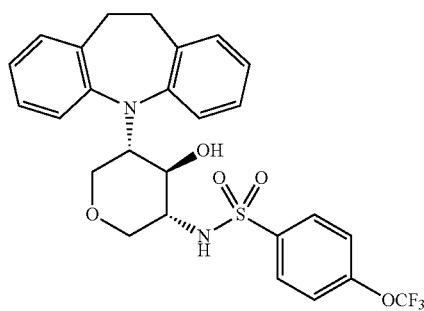 [SMILES: O=S(=O)(N[C@@H]1COC[C@H](N2c3ccccc3CCc3ccccc32)[C@H]1O)c1ccc(OC(F)(F)F)cc1] |
| 1b | 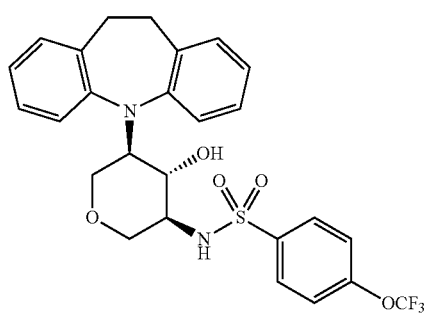 [SMILES: O=S(=O)(N[C@H]1COC[C@@H](N2c3ccccc3CCc3ccccc32)[C@@H]1O)c1ccc(OC(F)(F)F)cc1] |
| 2 | 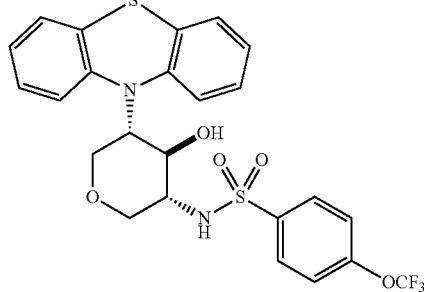 |
| 2a | 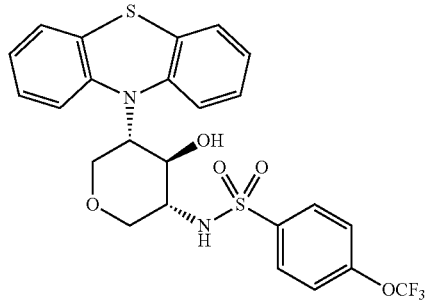 |
| 2b | 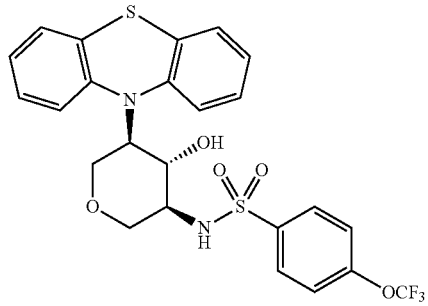 [SMILES: O=S(=O)(N[C@H]1COC[C@@H](N2c3ccccc3Sc3ccccc32)[C@@H]1O)c1ccc(OC(F)(F)F)cc1] |
| 3 | 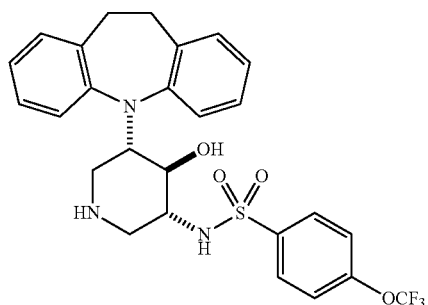 |
| 3a | 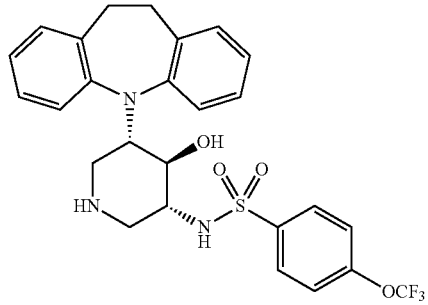 [SMILES: O=S(=O)(N[C@@H]1CNC[C@H](N2c3ccccc3CCc3ccccc32)[C@H]1O)c1ccc(OC(F)(F)F)cc1] |

25
-continued
| Compound ID | Structure |
|---|---|
| 3b | 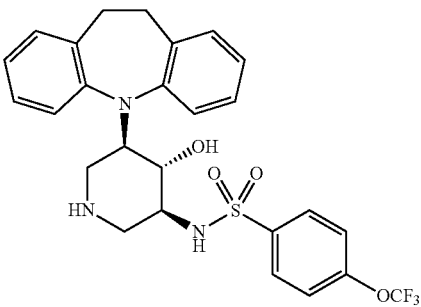 |
| 4 | 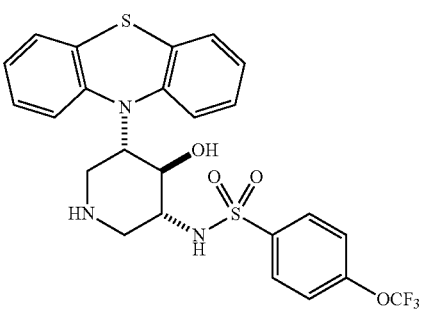 |
| 4a | 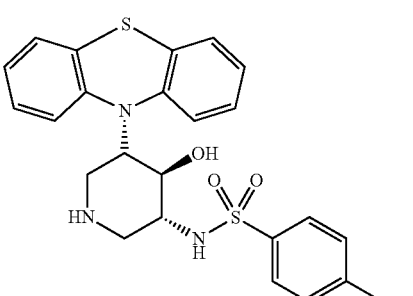 |
| 4b | 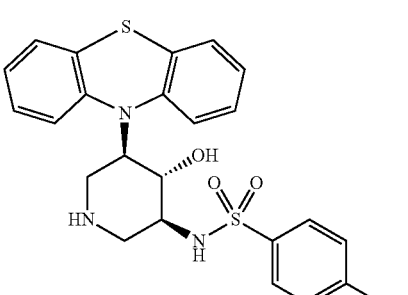 |
26
-continued
| Compound ID | Structure |
|---|---|
| 5 | 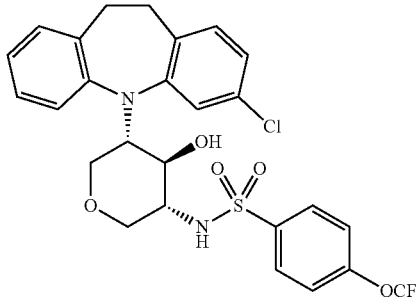 |
| 6 | 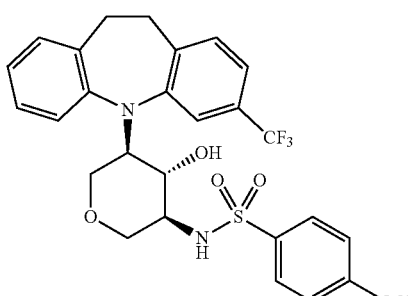 |
| 7 | 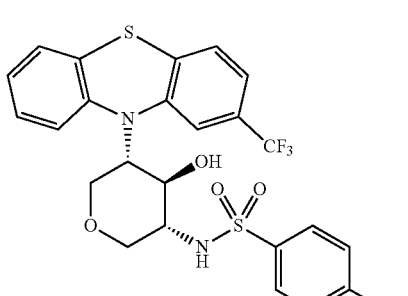 |
| 8 | 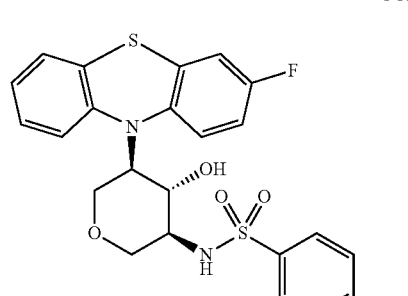 |
| 9 | 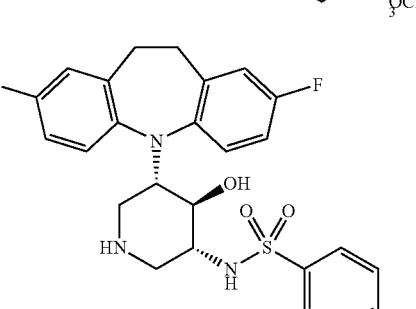 |

-continued

| Compound ID | Structure |
|---|---|
| 10 | 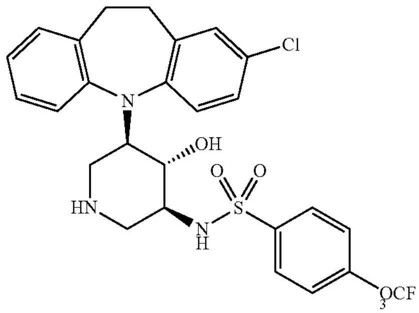 [SMILES: O=S(=O)(N[C@H]1CNC[C@@H](N2c3ccccc3CCc3cc(Cl)ccc32)[C@@H]1O)c1ccc(OC(F)(F)F)cc1] |
| 11 | 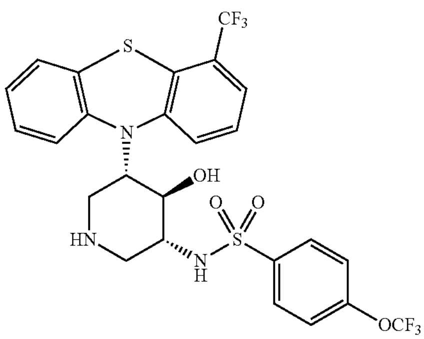 [SMILES: O=S(=O)(N[C@@H]1CNC[C@H](N2c3ccccc3Sc3c2cccc3C(F)(F)F)[C@H]1O)c1ccc(OC(F)(F)F)cc1] |
| 12 | 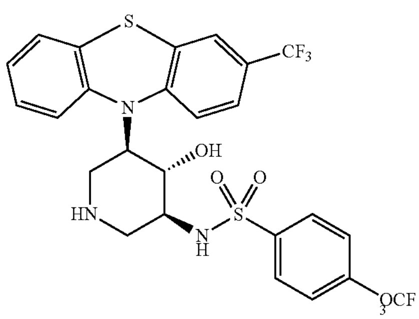 [SMILES: O=S(=O)(N[C@H]1CNC[C@@H](N2c3ccccc3Sc3cc(C(F)(F)F)ccc32)[C@@H]1O)c1ccc(OC(F)(F)F)cc1] |
| 13 | 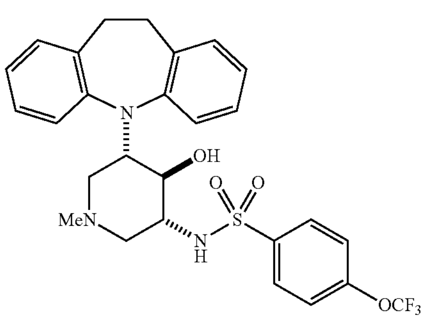 |

-continued

| Compound ID | Structure |
|---|---|
| 13a | 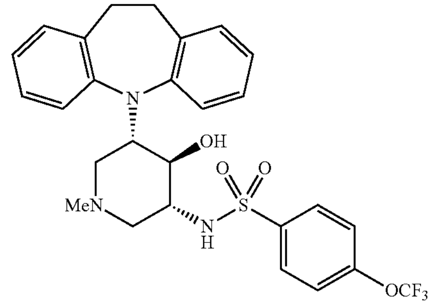 [SMILES: CN1C[C@@H](NS(=O)(=O)c2ccc(OC(F)(F)F)cc2)[C@H](O)[C@@H](N2c3ccccc3CCc3ccccc32)C1] |
| 13b | 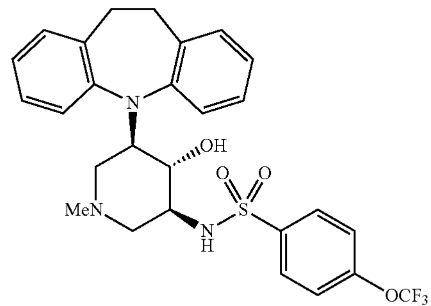 [SMILES: CN1C[C@H](NS(=O)(=O)c2ccc(OC(F)(F)F)cc2)[C@@H](O)[C@H](N2c3ccccc3CCc3ccccc32)C1] |
| 14 | 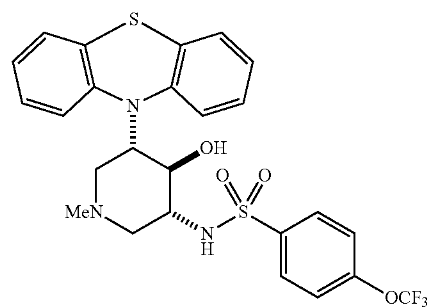 |
| 14a | 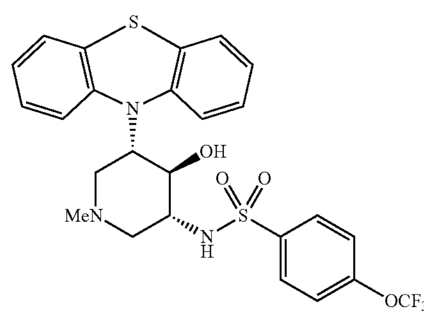 [SMILES: CN1C[C@@H](NS(=O)(=O)c2ccc(OC(F)(F)F)cc2)[C@H](O)[C@@H](N2c3ccccc3Sc3ccccc32)C1] |
| 14b | 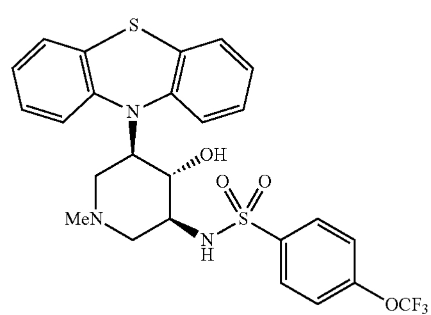 [SMILES: CN1C[C@H](NS(=O)(=O)c2ccc(OC(F)(F)F)cc2)[C@@H](O)[C@H](N2c3ccccc3Sc3ccccc32)C1] |

29
-continued
| Compound ID | Structure |
|---|---|
| 15 | 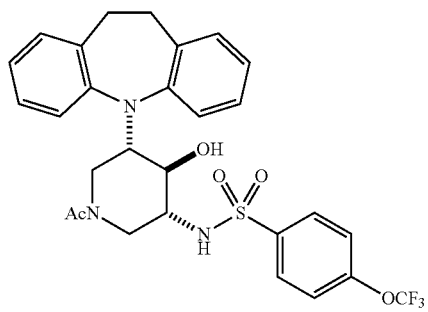 |
| 15a | 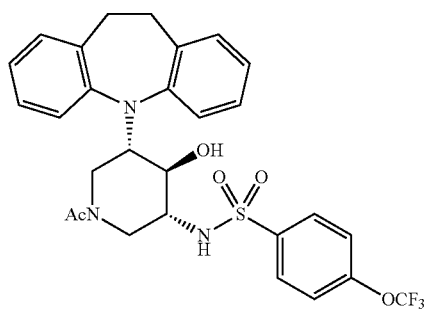 |
| 15b | 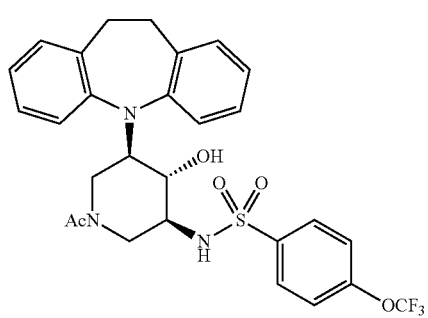 |
| 16 | 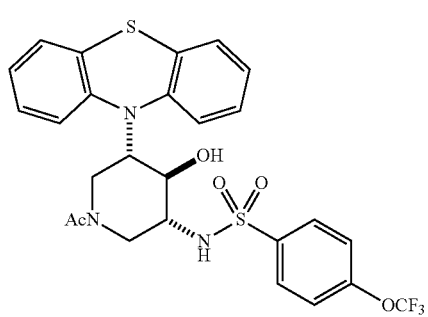 |
30
-continued
| Compound ID | Structure |
|---|---|
| 16a | 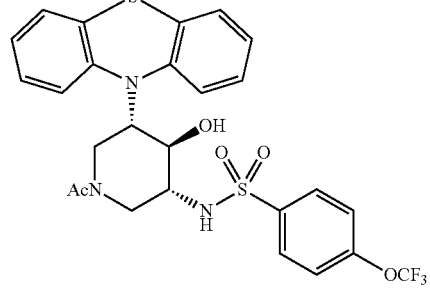 |
| 16b | 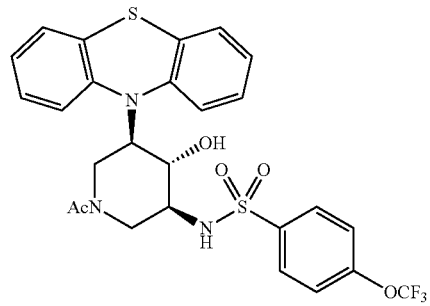 |
| 17 | 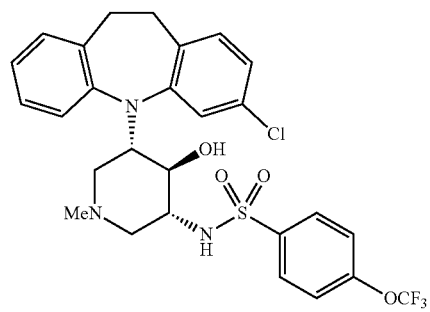 [SMILES: CN1C[C@@H](NS(=O)(=O)c2ccc(OC(F)(F)F)cc2)[C@H](O)[C@@H](N2c3ccccc3CCc3ccc(Cl)cc32)C1] |
| 18 | 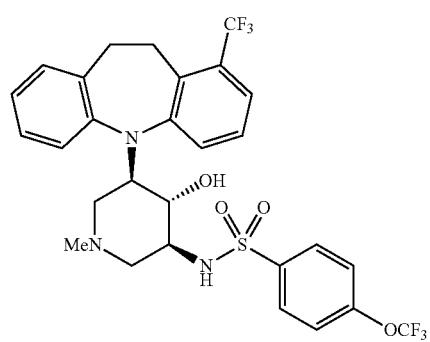 [SMILES: CN1C[C@H](NS(=O)(=O)c2ccc(OC(F)(F)F)cc2)[C@@H](O)[C@H](N2c3ccccc3CCc3c2cccc3C(F)(F)F)C1] |

-continued

| Compound ID | Structure |
|---|---|
| 19 | (phenothiazine with F)-piperidine(N-Me, OH)-NHSO₂-C₆H₄-OCF₃ |
| 20 | (phenothiazine with Cl)-piperidine(N-Me, OH)-NHSO₂-C₆H₄-OCF₃ |
| 21 | (dibenzazepine)-piperidine(N-CH₂CH₂OH, OH)-NHSO₂-C₆H₄-OCF₃ |
| 22 | (dibenzazepine)-piperidine(N-COCH₂OH, OH)-NHSO₂-C₆H₄-OCF₃ |
| 23 | (phenothiazine with CF₃)-piperidine(N-cyclopropyl, OH)-NHSO₂-C₆H₄-OCF₃ |

-continued

| Compound ID | Structure |
|---|---|
| 24 | (phenothiazine)-piperidine(N-(4-Cl-C₆H₄), OH)-NHSO₂-C₆H₄-OCF₃ |
| 25 | (dibenzazepine, saturated)-piperidine(N-Boc, OH)-NHSO₂-C₆H₄-OCF₃ |
| 25a | (dibenzazepine)-piperidine(N-Boc, OH)-NHSO₂-C₆H₄-OCF₃ |
| 25b | (dibenzazepine)-piperidine(N-Boc, OH)-NHSO₂-C₆H₄-OCF₃ |
| 26 | (dibenzazepine, saturated)-piperidine(N-CO₂Me, OH)-NHSO₂-C₆H₄-OCF₃ |

| Compound ID | Structure |
|---|---|
| 27 | 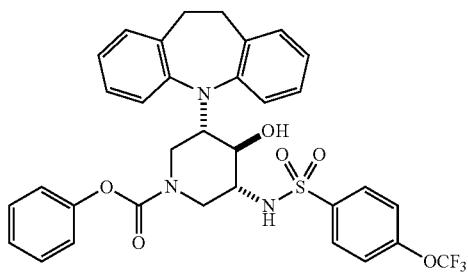 |
| 28 | 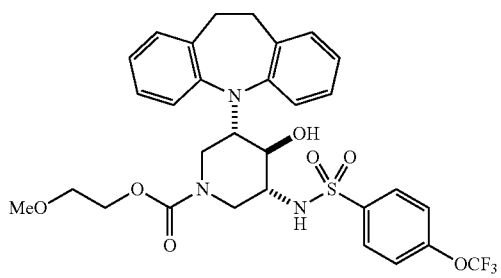 |
| 29 | 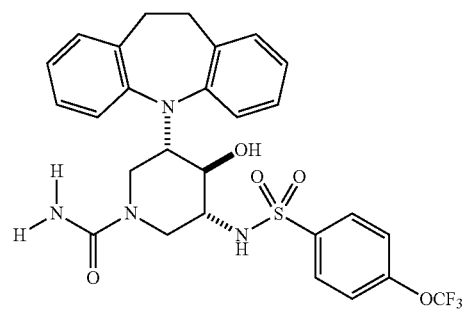 |
| 30 | 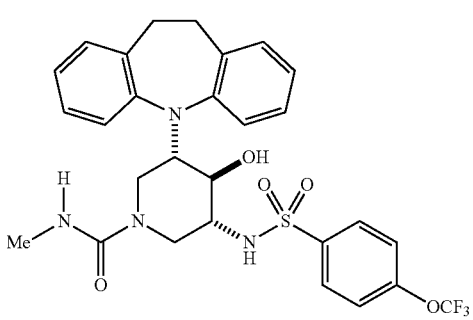 |
| 31 | 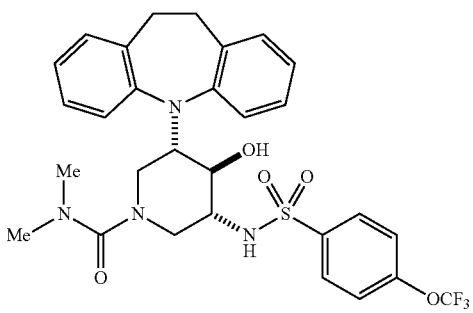 |
| Compound ID | Structure |
|---|---|
| 32 | 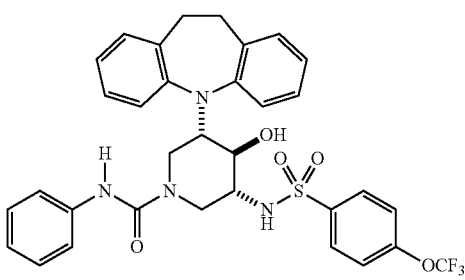 |
| 33 | 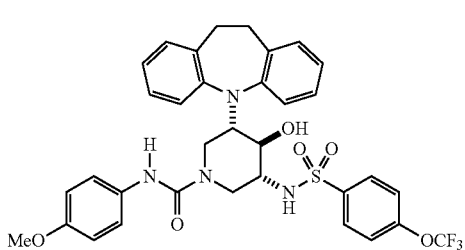 |
| 34 | 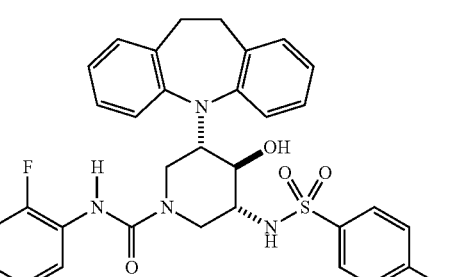 |
| 35 | 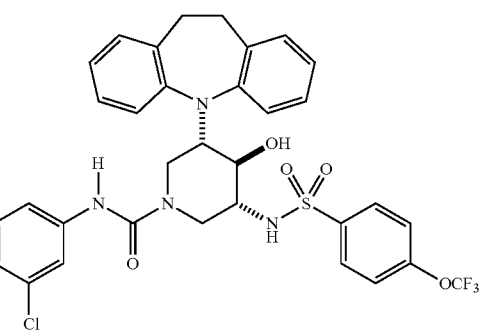 |
| 36 | 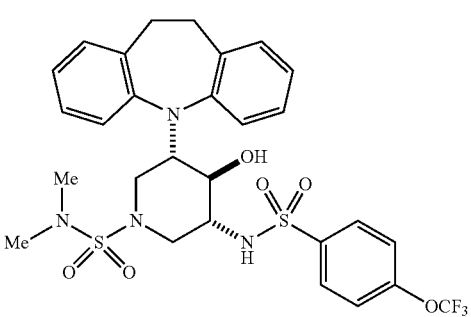 |

| Compound ID | Structure |
|---|---|
| 37 | 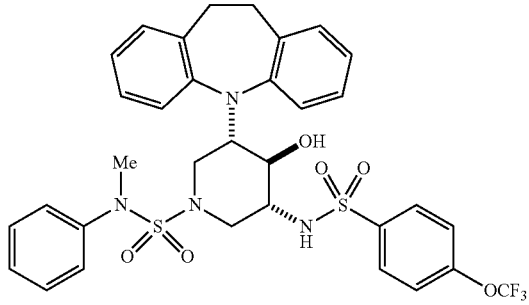 |
| 38 | 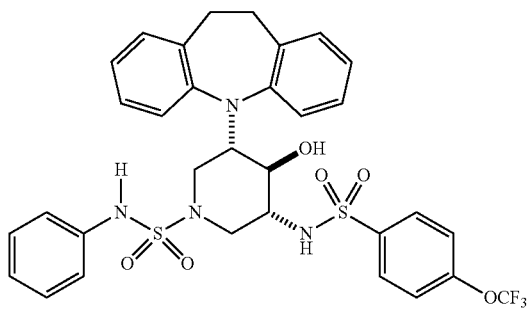 |
| 39 | 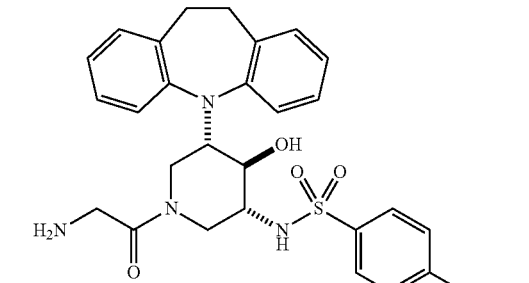 |
| 40 | 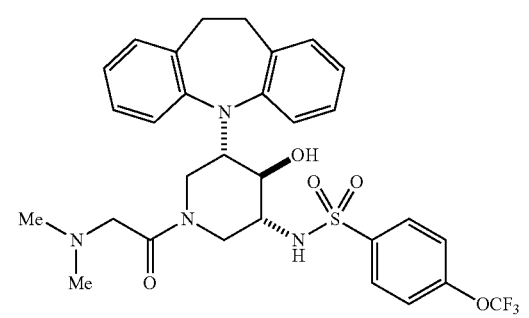 |
| 41 | 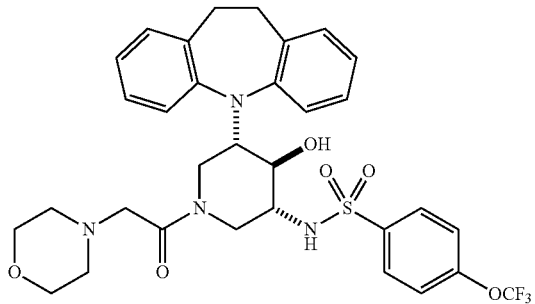 |
| Compound ID | Structure |
|---|---|
| 42 | 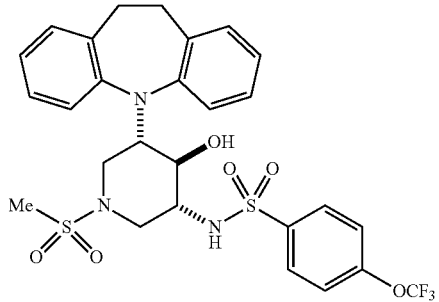 |
| 43 | 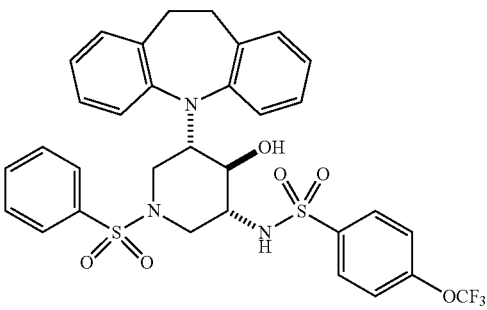 |
| 44 | 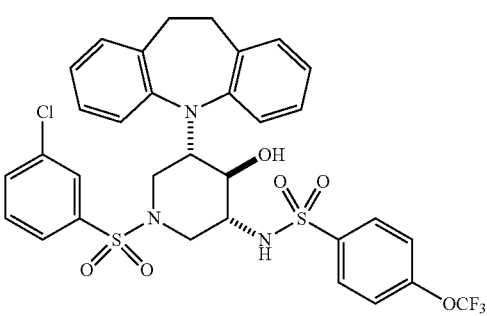 |
| 45 | 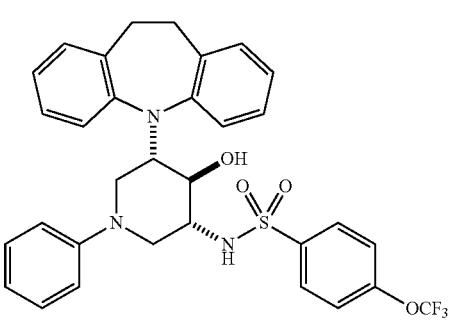 |

TABLE-continued
| Compound ID | Structure |
|---|---|
| 46 | 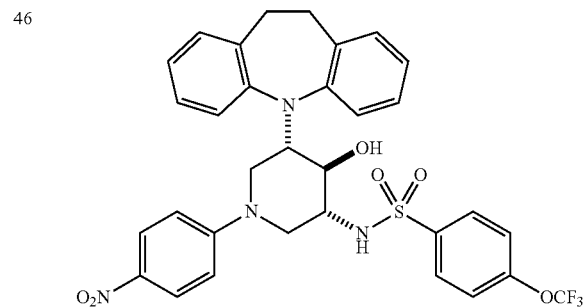 |
| 47 | 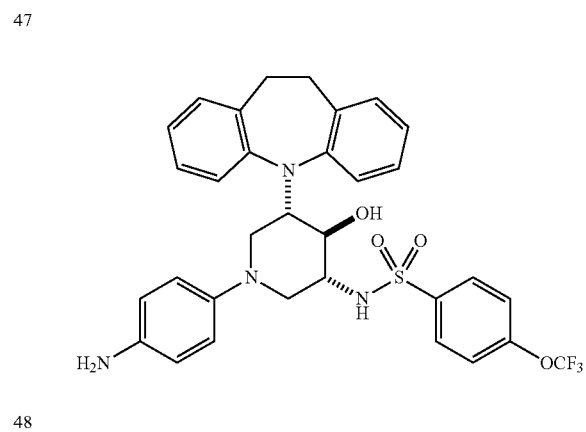 |
| 48 | 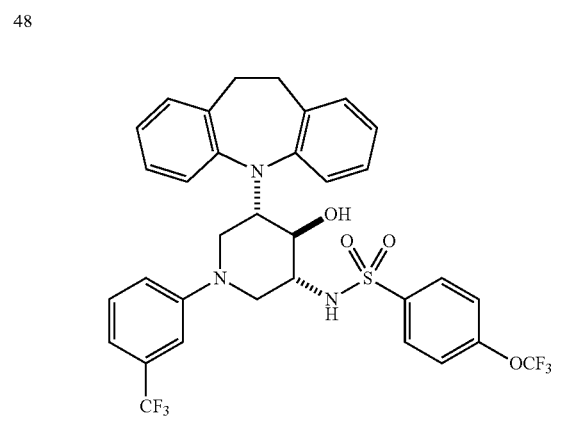 |
| 49 | 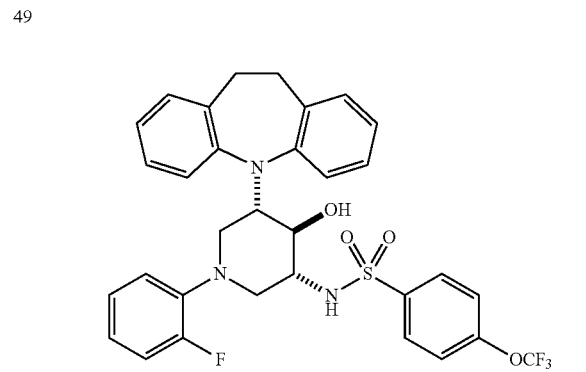 |
| 50 | 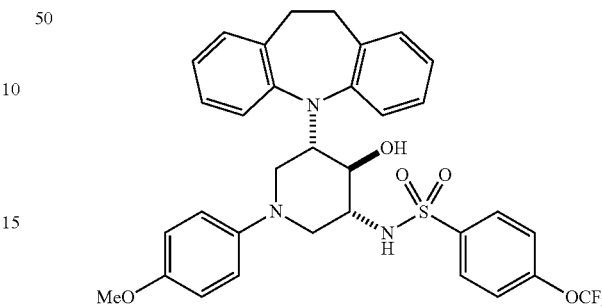 |
| 51 | 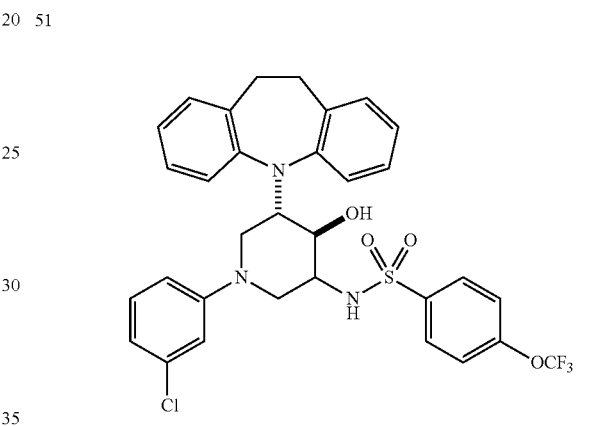 |
| 52 | 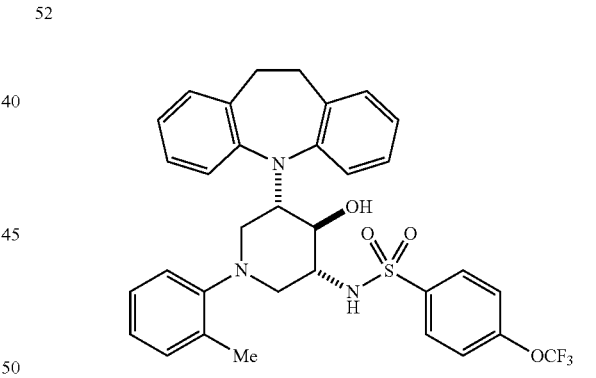 |
| 53 | 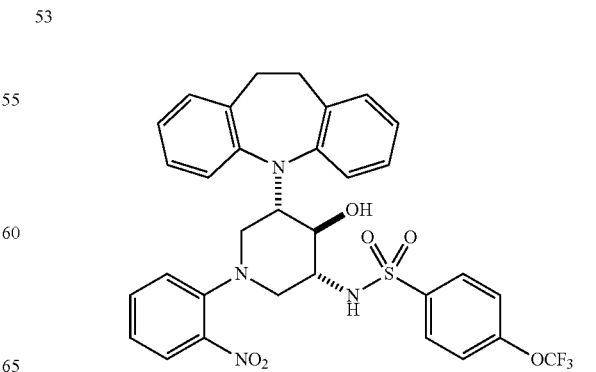 |

| Compound ID | Structure |
|---|---|
| 54 | 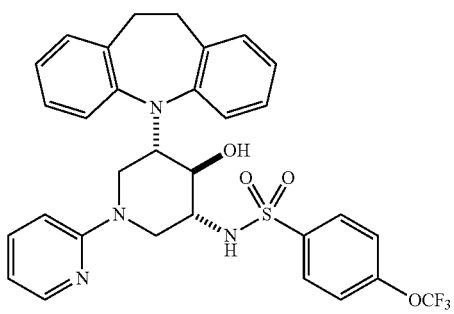 |
| 55 | 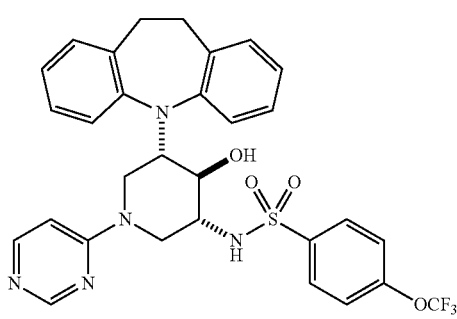 |
| 56 | 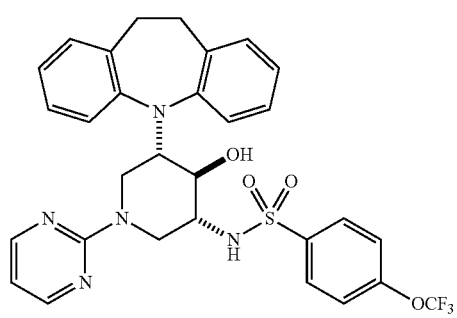 |
| 57 | 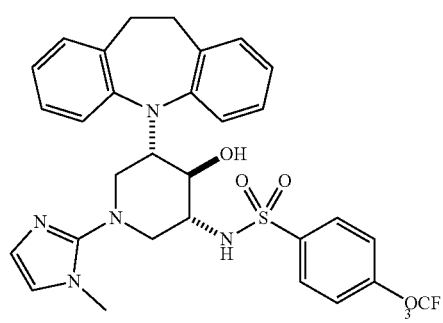 |

| Compound ID | Structure |
|---|---|
| 58 | 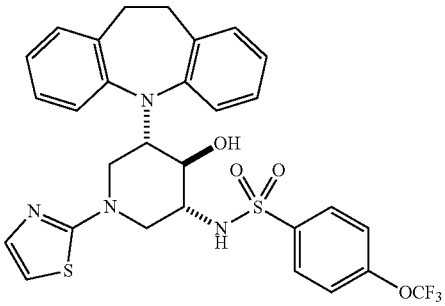 |

Preparation of compounds can involve the protection and deprotection of various chemical groups. The need for protection and deprotection, and the selection of appropriate protecting groups, can be readily determined by one skilled in the art. Suitable groups for that purpose are discussed in standard textbooks in the field of chemistry, such as Protective Groups in Organic Synthesis by T. W. Greene and P. G. M. Wuts [John Wiley & Sons, New York, 1999], in *Protecting Group Chemistry*, 1st Ed., Oxford University Press, 2000; and in *March's Advanced Organic chemistry: Reactions, Mechanisms, and Structure*, 5th Ed., Wiley-Interscience Publication, 2001.

Many compounds described herein may be prepared by the schemes shown in U.S. Provisional Application U.S. 62/201,819, which is incorporated herein by reference. In general, compounds can be prepared by:

(a) Reacting a Compound of Formula XII

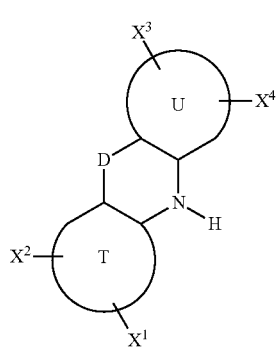

XII with a compound of formula XIII

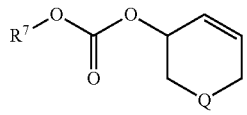

XIII wherein $R^7$ is $(C_1-C_4)$alkyl, in the presence of a palladium catalyst to provide a product of formula XIV

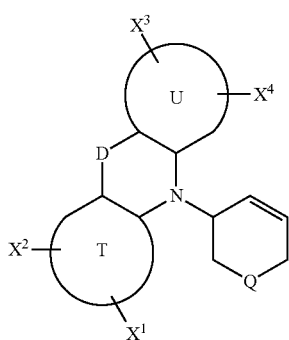

XIV and
oxidizing the product of formula XIV with osmium tetroxide to provide the cis diol XV or with meta chloroperbenzoic acid followed by hydrolysis of the resulting epoxide to provide the trans diol XVI:

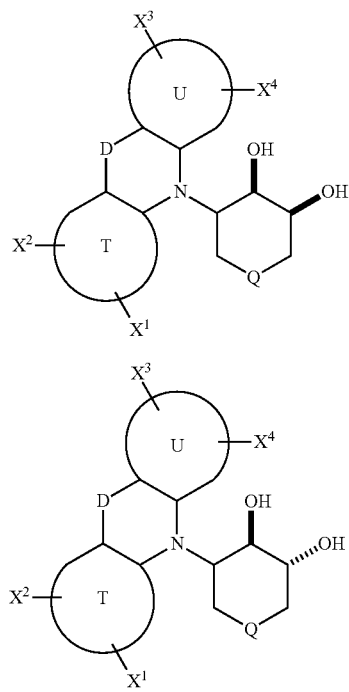

XV

XVI

If a chiral palladium catalyst is used in the initial step to make XIV, the stereochemistry can thus be controlled for all products downstream.

The diol of formula XV/XVI

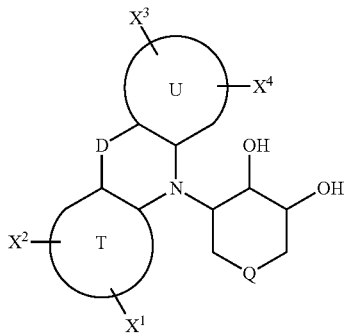

XV/XVI may be reacted with thionyl chloride or a sulfonyl chloride, such as methanesulfonyl chloride, to provide a sulfonylated product; and the sulfonylated product may be reacted with an alkali metal azide to provide a 3-azido-4-hydroxy-5-(heteroaryl)heterocycle of formula VI:

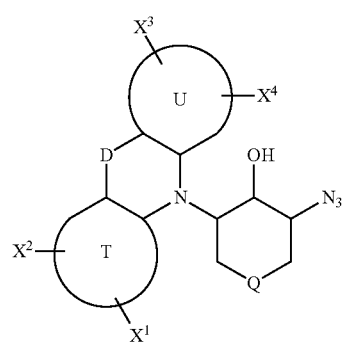

XVII

The azide may be reduced to provide the corresponding amine XVIII:

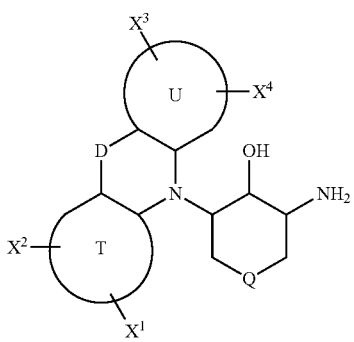

XVIII

A convenient reducing agent is triphenyl phosphine, but there are many procedures known to persons of skill that may be employed for reducing an azide to an amine. The amine XVIII may be reacted with the appropriate sulfonyl chloride to provide the products described herein in which Y is OH and Q is oxygen. When Q is NR, the compounds may be made in the same fashion as above but with R initially being a protecting group, such as t-Boc or Cbz. The protecting group is then cleaved after synthesis is complete, and the resulting NH condensed with any acylating or alkylating agent needed by procedures well-known in the art. Introduction of aryl or heteroaryl moieties onto the ring nitrogen may be achieved by $SN_{Ar}$ substitution reactions for electron deficient aromatic systems such 4-nitrophenyl or electrophilic heteroaromatic systems such as 4-pyrimidinyl systems.

More generally, arylation or heteroarylation of the ring nitrogen may be achieved by palladium mediated N-aryl amination: the Buchwald-Hartwig reaction, see for example N. Marion et al, in "Modified (NHC)Pd(allyl)Cl (NHC)N-Heterocyclic Carbene) Complexes for Room-Temperature Suzuki-Miyaura and Buchwald-Hartwig Reactions" J. Am. Chem. Soc. 2006, 128, 4101 or J. P. Wolfe et al in "Rational Development of Practical Catalysts for Aromatic Carbon-Nitrogen Bond Formation. Examples as applied to compounds of the present disclosure are shown in the scheme below:

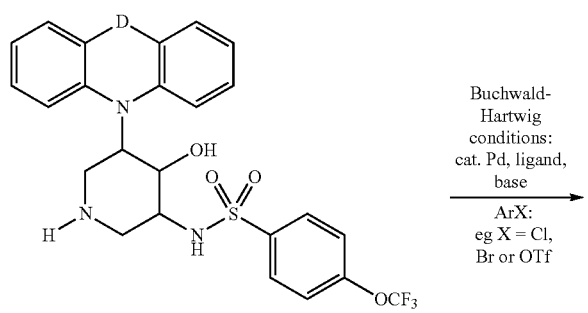
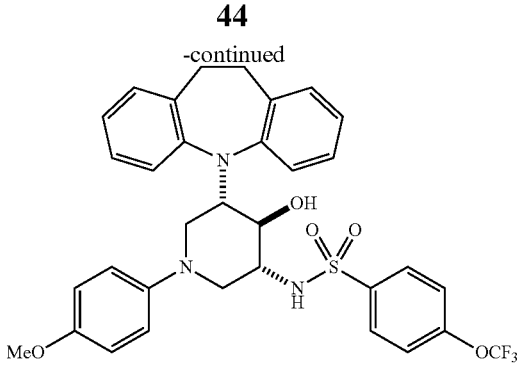
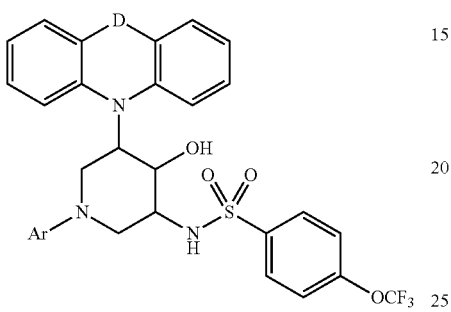
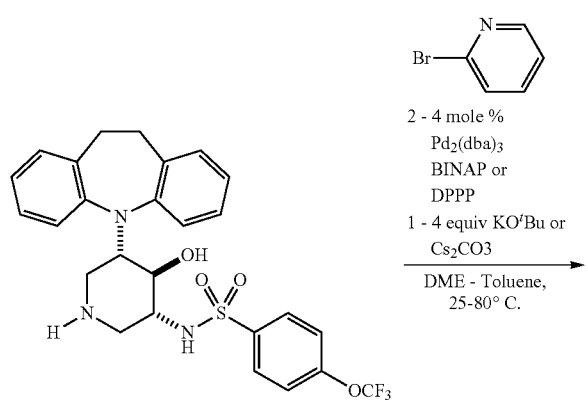
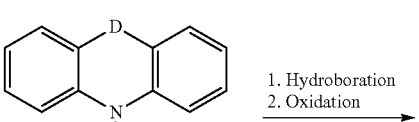

When Q is sulfur, the ring will either start out in the sulfone oxidation state or it will be oxidized to the sulfone when dihydroxylating the allylic olefin.

When compounds in which Y is hydrogen are desired, the olefin XIV may be treated with a sterically hindered hydroborating agent such as 9-BBN or the like, followed by oxidation of the alkyboron to the alcohol with an oxidant such as N-methylmorpholine-N-oxide or aqueous hydrogen peroxide. The alchol intermediate is converted to leaving group such as the mesylate and displaced with azide. This is carried forward to the target compound by reduction and reaction with the appropriate aryl sulfonyl chloride. This process is illustrated in the scheme below:

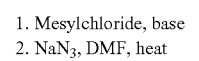
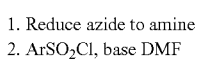
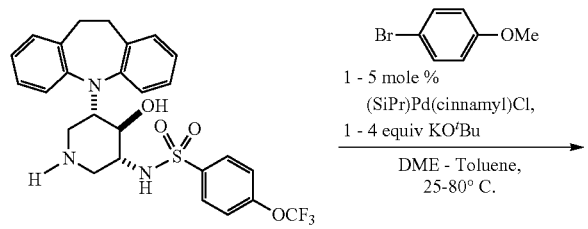
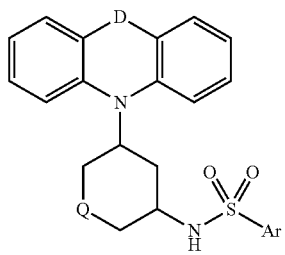

For example:

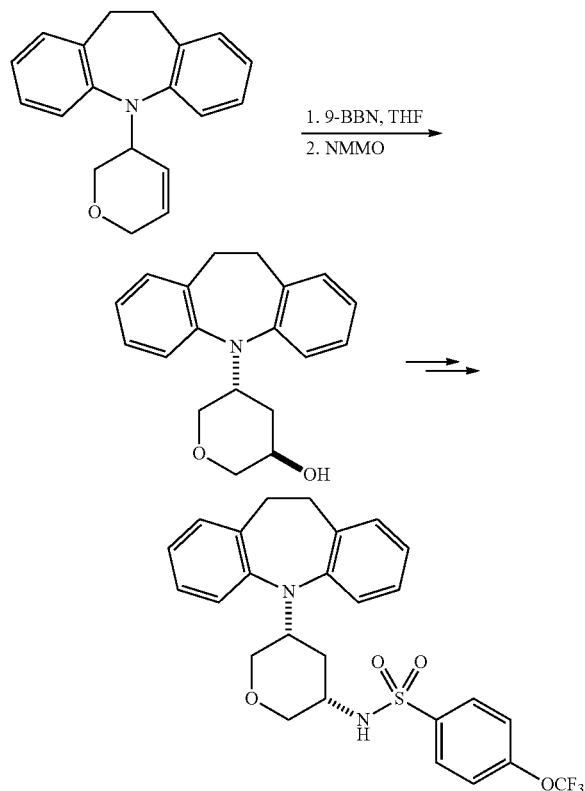

Alternatively, compounds in which Y=H maybe accessed via radical mediated deoxgenation processes as described in, for example, W. Hartwig in "Modern Methods For The Radical Deoxgenation of Alcohols", Tetrahedron Vol. 39, No. 16, page 2609 (1983). One example of this type of transformation as applied to compounds of the present invention (Barton-McCombie conditions) is shown below:

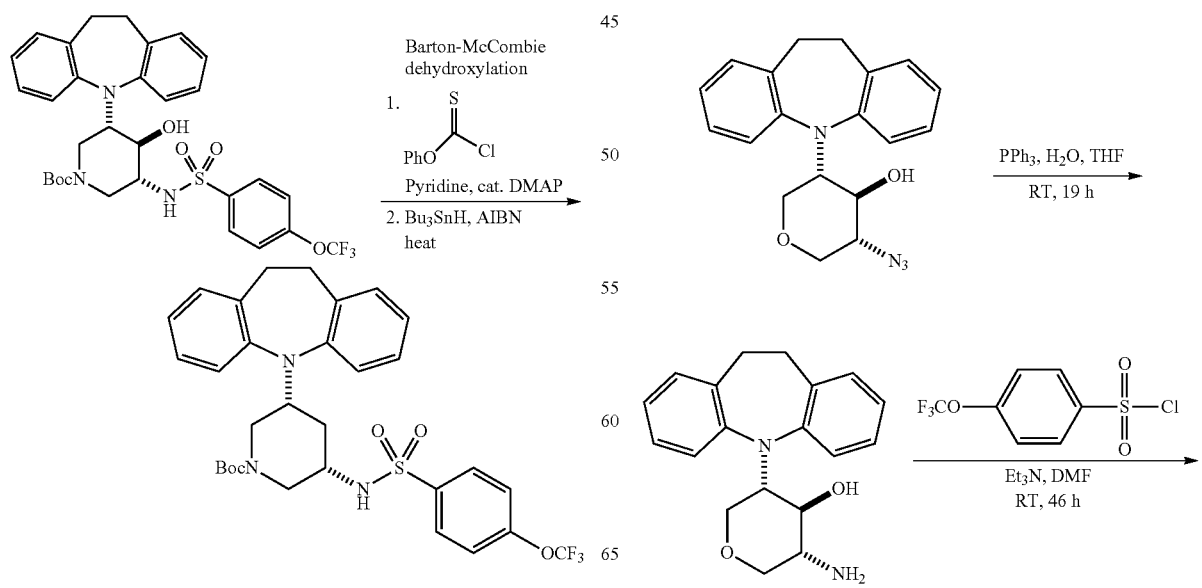

Exemplary Syntheses are Presented Below:

Scheme for Synthesis of Example 1:

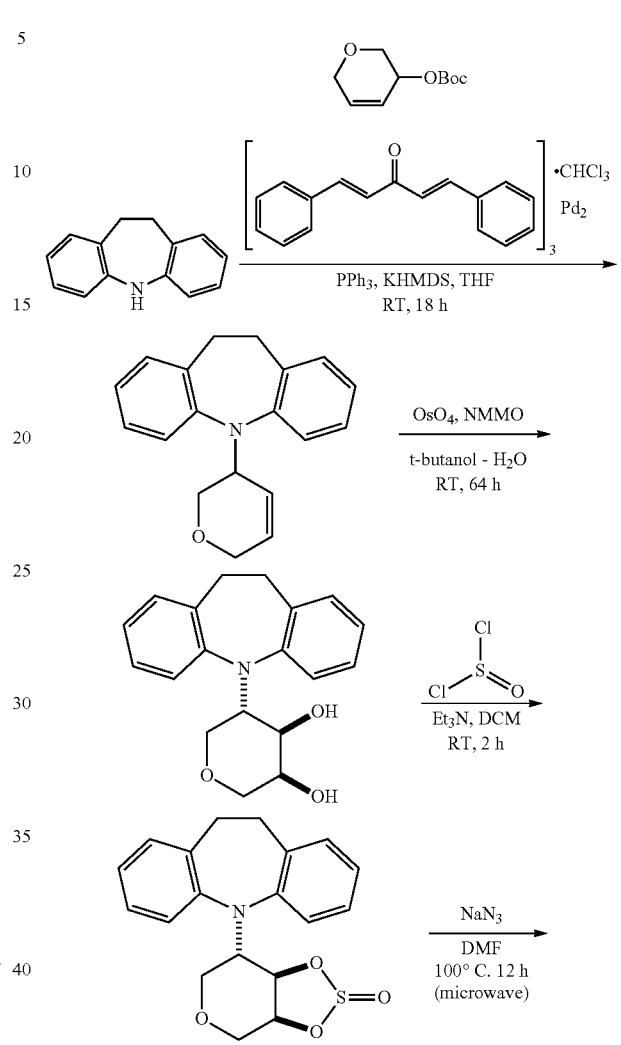

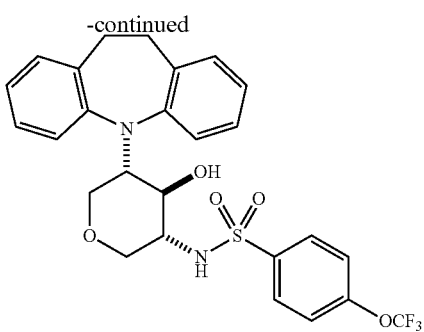

EXPERIMENTAL

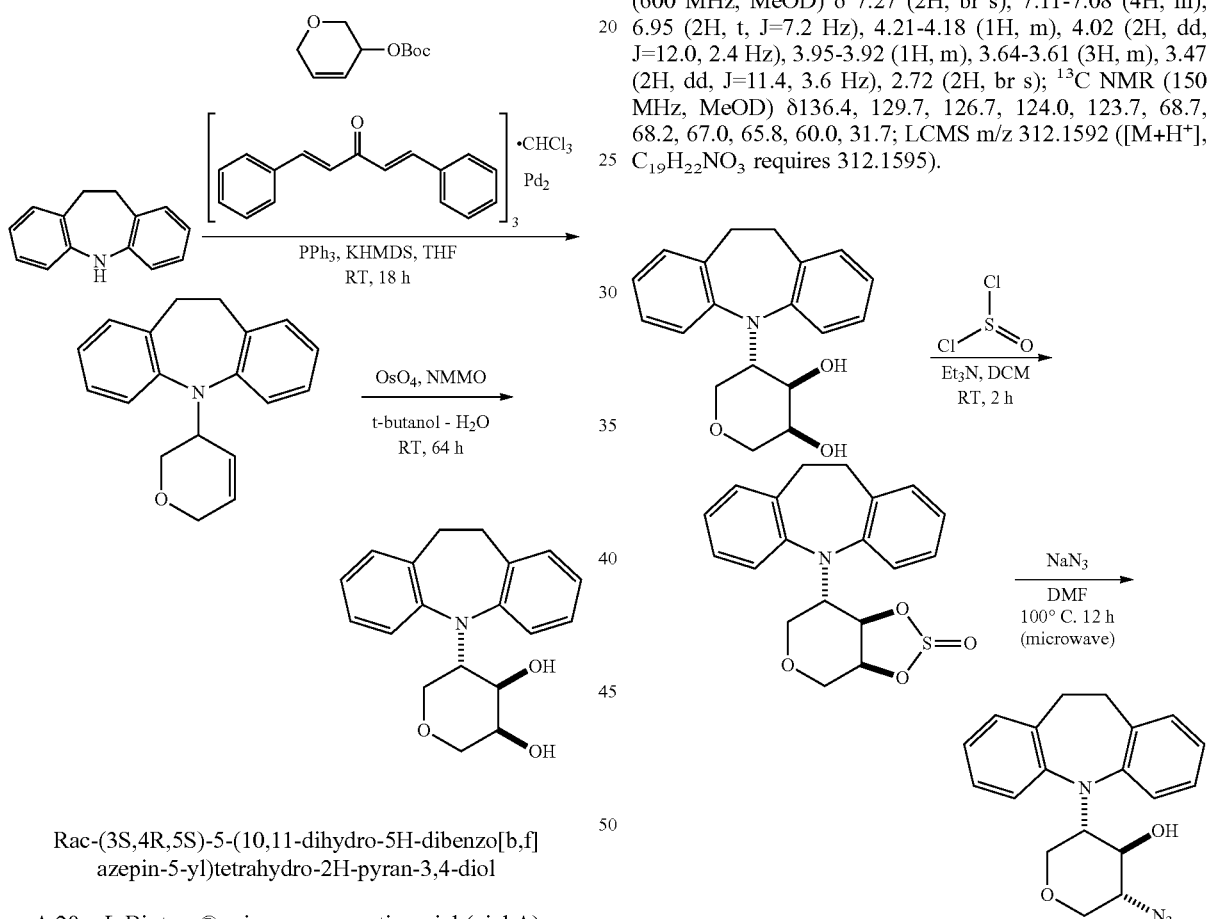

Rac-(3S,4R,5S)-5-(10,11-dihydro-5H-dibenzo[b,f]azepin-5-yl)tetrahydro-2H-pyran-3,4-diol A 20 mL Biotage® microwave reaction vial (vial A) was charged with Pd$_2$.dba$_3$. CHCl$_3$ (0.207 g, 0.200 mmol), and triphenyl phosphine (0.157 g, 0.600 mmol). The vial was sealed, evacuated and backfilled with argon three times. Dry degassed dichloromethane (7.50 mL) was added to this vial, and the mixture was stirred at RT for 60 min. A separate 20 mL Biotage® microwave reaction vial (vial B) was charged with 10,11-dihydro-5H-dibenzo[b,f]azepine (0.781 g, 4.00 mmol) and dry degassed dichloromethane (7.50 mL), followed by potassium bis(trimethylsilyl)amide (3.60 mL, 3.60 mmol, 1 M solution in THF), and the mixture was stirred at RT for 60 min. After stirring for 60 min, Rac-tert-butyl (3,6-dihydro-2H-pyran-3-yl) carbonate (0.961 g, 4.80 mmol) was added to vial A, all its contents were transferred to vial B, and the reaction mixture was stirred at RT for 18 h. At this point, the reaction mixture was evaporated onto silica gel and subjected to column chromatography (SiO$_2$; 1% ethyl-lacetate in hexanes) to afford slightly crude 5-(3,6-dihydro-2H-pyran-3-yl)-10,11-dihydro-5H-dibenzo[b,f]azepine (0.431 g) which was taken to the next step.

A solution of 5-(3,6-dihydro-2H-pyran-3-yl)-10,11-dihydro-5H-dibenzo[b,f]azepine (0.431 g, 1.55 mmol), 4-methylmorpholine N-oxide monohydrate (0.400 g, 3.42 mmol), and osmium tetroxide (0.32 mL, 0.032 mmol, 2.5% in tert-butanol) in tert-butanol (2.20 mL) and water (0.43 mL), was stirred at RT for 64 h. Reaction mixture from both batches were treated with solid sodium bisulfite, stirred for 1 h, evaporated on to silica, and purified by flash chromatography (SiO$_2$, 0%-66% ethyl acetate-hexanes) to afford title compound (0.242 g, 20% over two steps). $^1$H NMR (600 MHz, MeOD) δ 7.27 (2H, br s), 7.11-7.08 (4H, m), 6.95 (2H, t, J=7.2 Hz), 4.21-4.18 (1H, m), 4.02 (2H, dd, J=12.0, 2.4 Hz), 3.95-3.92 (1H, m), 3.64-3.61 (3H, m), 3.47 (2H, dd, J=11.4, 3.6 Hz), 2.72 (2H, br s); $^{13}$C NMR (150 MHz, MeOD) δ136.4, 129.7, 126.7, 124.0, 123.7, 68.7, 68.2, 67.0, 65.8, 60.0, 31.7; LCMS m/z 312.1592 ([M+H$^+$], C$_{19}$H$_{22}$NO$_3$ requires 312.1595).

Rac-(3R,4R,5S)-3-azido-5-(10,11-dihydro-5H-dibenzo[b,f]azepin-5-yl)tetrahydro-2H-pyran-4-ol A solution of Rac-(3S,4R,5S)-5-(10,11-dihydro-5H-dibenzo[b,f]azepin-5-yl)tetrahydro-2H-pyran-3,4-diol (0.188 g, 0.603 mmol) in dichloromethane (1.50 mL) was cooled to 0° C., treated with triethylamine (0.669 mL, 4.82 mmol), then thionyl chloride (0.131 mL, 1.81 mmol) was added drop-wise. The reaction mixture was warmed to room temperature, stirred for 2 h, partitioned between dichloromethane and water. The organic layer was concentrated to give a residue, which was subjected to column chromatography (SiO$_2$, 17% ethylacetate in hexanes) to afford slightly crude Rac-(3aS,7S,7aR)-7-(10,11-dihydro-5H-dibenzo[b,f]azepin-5-yl)tetrahydro-3aH-[1,3,2]dioxathiolo[4,5-c]pyran 2-oxide (0.088 g) which was taken to the next step.

A solution of Rac-(3aS,7S,7aR)-7-(10,11-dihydro-5H-dibenzo[b,f]azepin-5-yl)tetrahydro-3aH-[1,3,2]dioxathiolo[4,5-c]pyran 2-oxide (0.088 g, 0.246 mmol) in DMF (1.50 mL) was treated with sodium azide (0.019 g, 2.95 mmol), and heated to 100° C. in a microwave for 12 h. The reaction mixture was treated with sat. aq. NH$_4$Cl, extracted with ethylacetate, washed with brine, concentrated, purified by column chromatography (SiO$_2$, 6%-13% ethylacetate-hexanes) to afford the title compound (0.039 g, 19% over two steps). $^1$H NMR (600 MHz, MeOD) δ 7.35 (2H, br s), 7.11-7.07 (4H, m), 6.97 (2H, br s), 4.28-4.27 (1H, m), 3.85-3.79 (2H, m), 3.51-3.46 (3H, m), 3.30 (1H, br s), 3.25-3.20 (1H, m), 2.92-2.87 (1H, m), 2.71 (2H, br s); $^{13}$C NMR (150 MHz, MeOD) δ 146.2, 138.4, 135.6, 129.7, 126.4, 124.2, 74.4, 69.8, 68.3, 66.8, 64.5, 32.5; LCMS m/z 337.1652 ([M+H$^+$], C$_{19}$H$_{21}$N$_4$O$_2$ requires 337.1660).

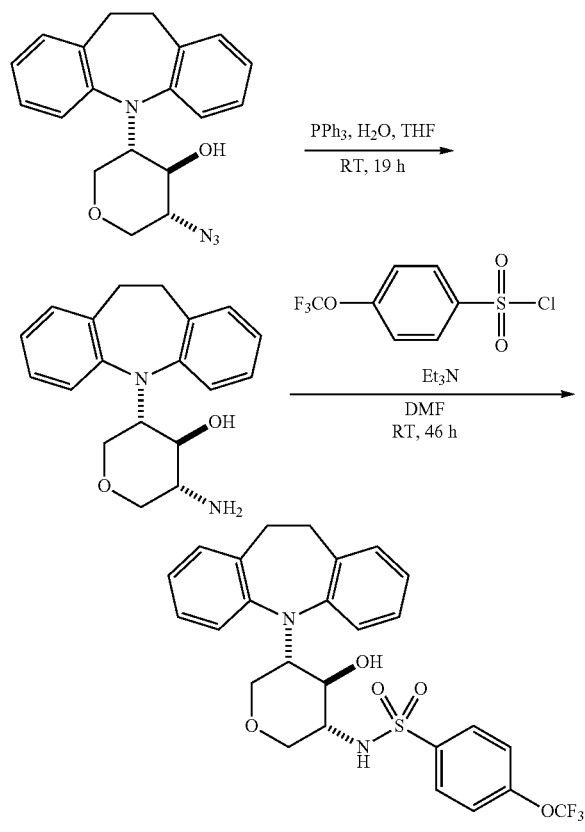

Rac-N-((3R,4R,5S)-5-(10,11-dihydro-5H-dibenzo[b,f]azepin-5-yl)-4-hydroxytetrahydro-2H-pyran-3-yl)-4-(trifluoromethoxy)benzenesulfonamide A solution of Rac-(3R,4R,5S)-3-azido-5-(10,11-dihydro-5H-dibenzo[b,f]azepin-5-yl)tetrahydro-2H-pyran-4-ol (0.039 g, 0.116 mmol) in THF (1.00 mL) was cooled to 0° C., treated with PPh$_3$ (0.033 g, 0.128 mmol), H$_2$O (0.001 mL, 0.055 mmol), and stirred for 19 h at room temperature. The solution was concentrated to dryness, dissolved in a minimal amount of dichloromethane and purified by flash chromatography (SiO$_2$, 100% hexanes, 50% ethyl acetate-hexanes, 5%, methanol-dichloromethane, 17:2:1 dichloromethane:methanol:35% ammonium hydroxide) to afford slightly crude Rac-(3R,4S,5S)-3-amino-5-(10,11-dihydro-5H-dibenzo[b,f]azepin-5-yl)tetrahydro-2H-pyran-4-ol (0.027 g) which was taken to the next step.

A solution of Rac-(3R,4S,5S)-3-amino-5-(10,11-dihydro-5H-dibenzo[b,f]azepin-5-yl)tetrahydro-2H-pyran-4-ol (0.027 g, 0.095 mmol) in DMF (1.00 mL) was cooled to 0° C., treated with triethylamine (0.053 mL, 0.382 mmol), and 4-(trifluoromethoxy)benzene-1-sulfonyl chloride (0.018 mL, 0.105 mmol). The mixture was warmed to room temperature, and stirred for 46 h. The mixture was partitioned between water and ethylacetate. The organic layer was washed with brine, and concentrated in vacuo. The residue was dissolved in a minimal amount of dichloromethane and purified by flash chromatography (SiO$_2$, 9%-20% ethylacetate-hexanes) to afford the title compound (0.031 g, 51% over two steps). $^1$H NMR (600 MHz, MeOD) δ 7.86 (2H, d, J=8.4 Hz), 7.38 (2H, d, J=8.4 Hz), 7.24 (2H, d, J=7.8 Hz), 7.08-7.07 (4H, m), 6.97 (2H, br s), 4.18 (1H, dd, J=11.4, 3.6 Hz), 3.77 (1H, td, J=8.4, 4.2 Hz), 3.71 (1H, dd, J=11.4, 4.2 Hz), 3.60 (1H, br s), 3.48 (1H, t, J=8.4 Hz), 3.37 (2H, t, J=10.2 Hz), 3.18 (1H, td, J=8.4, 4.8 Hz), 3.05 (1H, t, J=10.8 Hz), 2.72 (2H, br s); $^{13}$C NMR (150 MHz, MeOD) δ 151.8, 146.5, 140.2, 136.8, 129.9, 129.2, 126.3, 125.2, 124.0, 120.9, 70.4, 69.5, 68.7, 64.9, 56.5, 32.1; LCMS m/z 535.1501 ([M+H$^+$], C$_{26}$H$_{26}$F$_3$N$_2$O$_5$S requires 535.1510).

Piperidine Example. tert-butyl 3,4-dihydroxy-5-(10,11-dihydro-5H-dibenzo[b,f]azepin-5-yl))piperidine-1-carboxylate

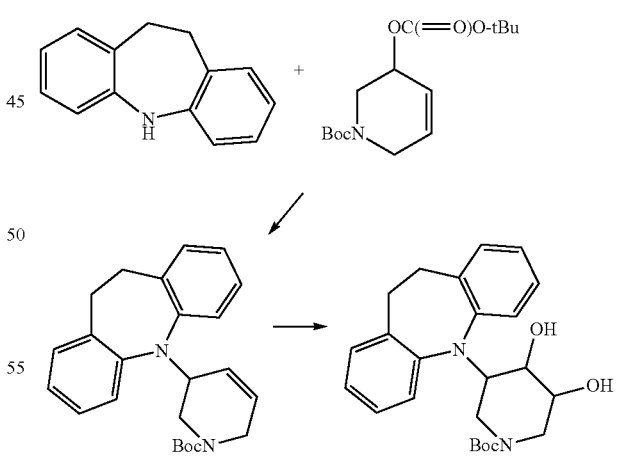

To a solution of tert-butyl 5-hydroxy-5,6-dihydropyridine-1 (2H)-carboxylate (0.500 g, 2.50 mmol) in THF (8.0 mL) is added n-butyllithium (2.5 M in hexanes, 0.99 mL, 2.50 mmol) at −78° C. The resulting solution is warmed to 0° C. and stirred for 5 min prior to addition of di-tert-butyl dicarbonate (0.600 g, 2.76 mmol) in THF (4.0 mL). The reaction is warmed to RT, stirred for 17 h. The reaction is then quenched with water, extracted with ethyl acetate, washed with brine, concentrated, and the residue purified by flash chromatography (SiO$_2$, 0%-3% ethyl acetate-hexanes) to afford crude tert-butyl 5-((tert-butoxycarbonyl)oxy)-5,6-dihydropyridine-1(2H)-carboxylate (0.825 g) as a colorless oil which is taken to the next step without further purification.

A 5 mL Biotage® microwave reaction vial is charged with Pd$_2$.dba$_3$. CHCl$_3$ (0.025 g, 0.024 mmol), and (R,R)-DACH-phenyl Trost ligand (0.052 g, 0.075 mmol). The vial is sealed, evacuated and backfilled with argon three times. Dry degassed dichloromethane (1.25 mL) is added to this vial, and the mixture is stirred at room temperature for 30 min. Racemic tert-butyl cyclohex-2-en-1-yl carbonate (0.359 g, 1.20 mmol) is added to the vial and the contents were transferred to a separate 5 mL Biotage® microwave reaction vial containing 10,11-dihydro-5H-dibenzo[b,f]azepine (0.50 mmol) in dry degassed dichloromethane (1.50 mL). The reaction mixture is stirred at room temperature for 10 days. At this point, the reaction mixture is evaporated onto silica gel and subjected to column chromatography (SiO$_2$; 0%-5% ethylacetate in hexanes) to afford crude (R)-tert-butyl 5-(10,11-dihydro-5H-dibenzo[b,f]azepin-5-yl)-5,6-dihydropyridine-1(2H)-carboxylate, which is taken to the next step without purification.

A solution of (R)-tert-butyl 5-(10,11-dihydro-5H-dibenzo[b,f]azepin-5-yl)-5,6-dihydropyridine-1(2H)-carboxylate (0.346 mmol), 4-methylmorpholine N-oxide monohydrate (0.089 g, 0.761 mmol), and osmium tetroxide (0.080 mL, 0.007 mmol, 2.5% in tert-butanol) in tert-butanol (2.0 mL) and water (0.40 mL), is stirred at RT for 42 h. The reaction mixture is treated with solid sodium bisulfite solution, stirred for 1 h, evaporated on to silica and purified by flash chromatography (SiO$_2$, 0%-70% ethyl acetate-hexanes) to afford (R)-tert-butyl 5-(10,11-dihydro-5H-dibenzo[b,f]azepin-5-yl)-5,6-dihydropyridine-1(2H)-carboxylate.

Alternate Epoxidation Route

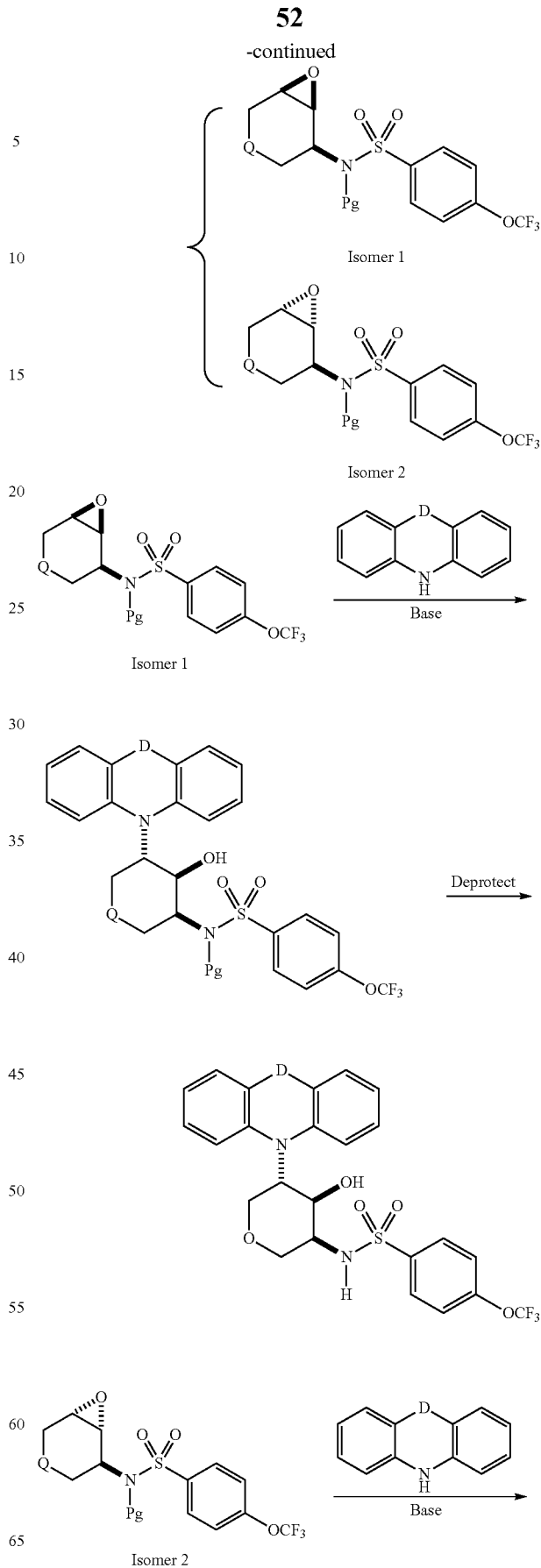

-continued

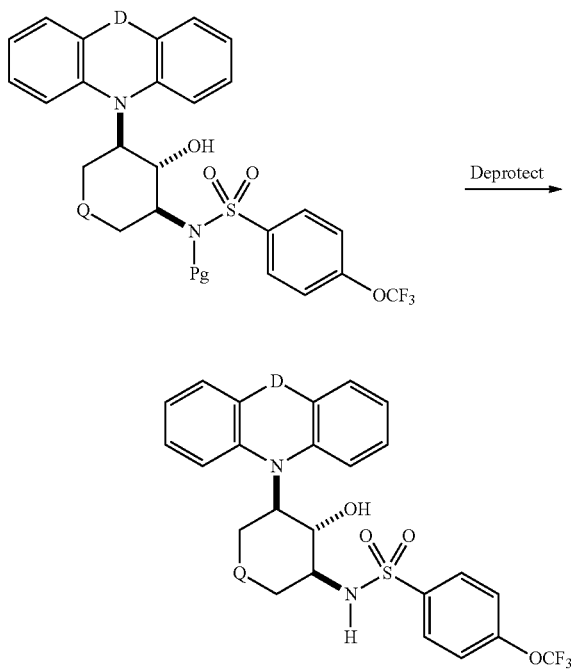

An alternative route to PP2A modulators described in the present application is outlined in Scheme (1) in which a heterocyclic allylic carbonate is first reacted with a protected aryl sulfonamide in the presence of a palladium catalyst. This may be carried out with control of the newly formed chiral center by using a chiral ligand such as the Trost-DACH bisphosphine. Thus reagents of type (i) are reacted with an optionally protected arylsulfonamide (ii), for example 4-trifluoromethoxybenzene sulfonamide in the presence of a chiral palladium catalyst to give enantiomerically enriched allylarylsulfonamides of type (iii). Protecting groups, Pg, include but are not limited to, benzyl and substituted benzyl groups or alkoxycarbonyl groups such as Boc or Cbz. The protected allylic sulfonamides (iii) may be epoxidized in a non-diastereoselective fashion to give a diasteromeric mixture of epoxides, (iv), which are separated by chromatographic techniques; or alternatively steroselective expoxidation will give access to one diastereoisomer preferentially. Epoxidation reagents include peroxoic acids such as mCPBA, dioxiranes such as dimethyldioxirane, oxaziridines such as 3-phenyl-2-tosyl-1,2-oxaziridine or hydroperoxides such as t-butylhydroperoxide with transition metal ion catalysis. Either isomer of compound (iv) is converted to a PP2A activator by treatment with a tricyclic moiety such as an optionally substituted dibenzoazepine or phenothiazine in the presence of a base such as sodium amide, sodium hydride or potassium t-butoxide in an aprotic solvent, followed by deprotection under conditions appropriate for the original choice of Pg. Alternatively the diastereomeric mixture of (iv) may be carried forward and isomers separated at the penultimate benzyl protected stage or the final deprotected products.

A specific example of this process is shown in Scheme 2

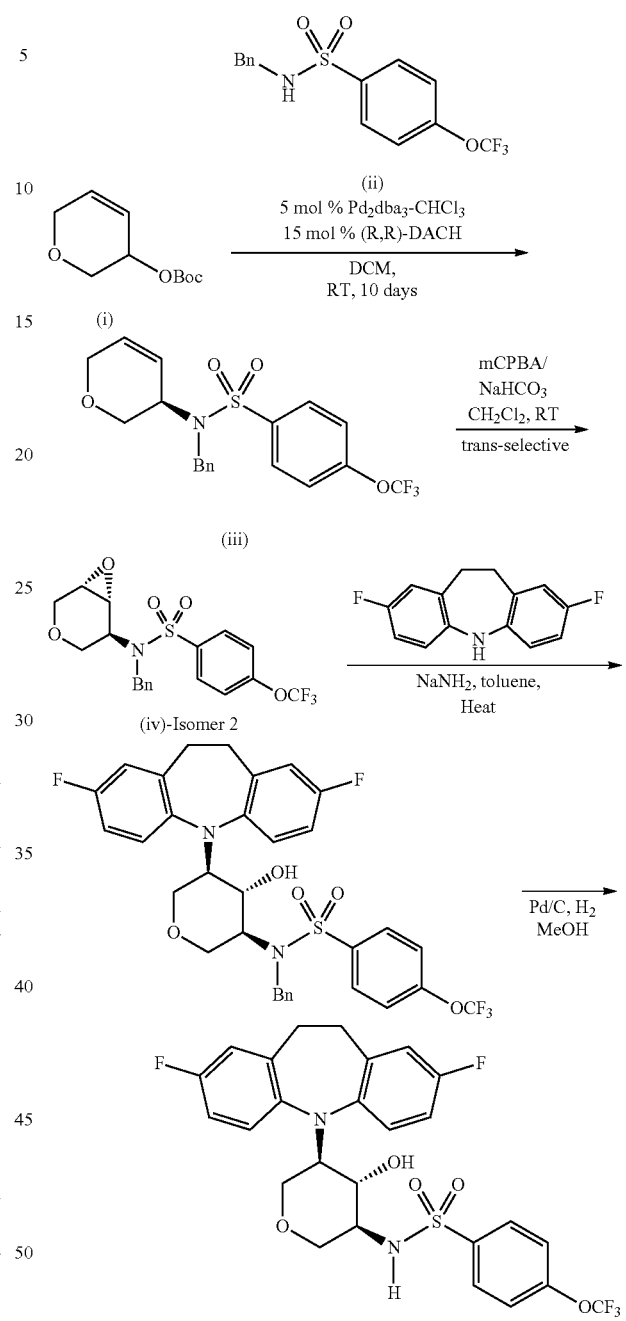

Synthesis of (R)—N-benzyl-N-(3,6-dihydro-2H-pyran-3-yl)-4-(trifluoromethoxy)benzenesulfonamide (iii)

Using the typical procedure N-benzyl-4-(trifluoromethoxy)benzenesulfonamide (0.200 g, 0.603 mmol) was reacted with tert-butyl (3,6-dihydro-2H-pyran-3-yl) carbonate (0.289 g, 1.45 mmol) in presence of (R,R)-L1 for 10 days to afford (R)—N-benzyl-N-(3,6-dihydro-2H-pyran-3-yl)-4-(trifluoromethoxy)benzenesulfonamide (0.228 g, 92%). $^1$H NMR (600 MHz, MeOD) δ 7.89 (2H, d, J=8.4 Hz), 7.43 (2H, d, J=8.4 Hz), 7.32 (2H, d, J=7.2 Hz), 7.26-7.20 (3H, m), 5.93 (1H, d, J=10.2 Hz), 5.41 (1H, d, J=10.2 Hz), 4.66-4.63 (1H, m), 4.48-4.44 (2H, m), 3.98-3.91 (2H, m), 3.70 (1H, dd, J=12.0, 4.2 Hz), 3.55 (1H, dd, J=12.0 3.6 Hz); $^{13}$C NMR (150 MHz, MeOD) δ 152.0, 140.0, 138.6, 132.0, 129.3, 127.9, 127.0, 123.0, 121.2, 119.6, 68.1, 64.5, 51.6, 48.3; HPLC analysis: (CHIRALPAK IA-3, 70:30 hexanes-EtOH-diethylamine, 1.0 mL/min, UV: 254 nm), tR=2.72 min (minor), 5.10 min (major); HPLC analysis: >94% ee Material produced in this fashion exhibited $[\alpha]^{25}$D=−93.0° (c=1.0, CH$_3$OH); HRMS m/z 414.0989 ([M+H$^+$], C$_{19}$H$_{19}$F$_3$NO$_4$S requires 414.0988).

Trans-stereoselective epoxidation of intermediate (iii) is carried out using conditions reported in O'Brien et al, Organic Letters, vol. 5, Pages 4955-4957, 2003, to give epoxide intermediate, (iv)-isomer 2. Epoxide opening is carried out with 2,8-difluoro-10,11-dihydro-5H-dibenzo[b,f]azepine in the presence of a base such as NaNH$_2$ in toluene with heating for 50-100° C. for between 1 and 24 hours. Deprotection of the benzyl group is carried out by hydrogenolysis with a catalyst such as palladium on carbon or palladium hydroxide, to give the PP2A modulator, N-((3S,4S,5R)-5-(2,8-difluoro-10,11-dihydro-5H-dibenzo[b,f]azepin-5-yl)-4-hydroxytetrahydro-2H-pyran-3-yl)-4-(trifluoromethoxy)benzenesulfonamide.

This synthetic approach may also be used for the synthesis other systems including those containing heteroaromatic tricyclic moieties as shown in Scheme 3.

Scheme 3

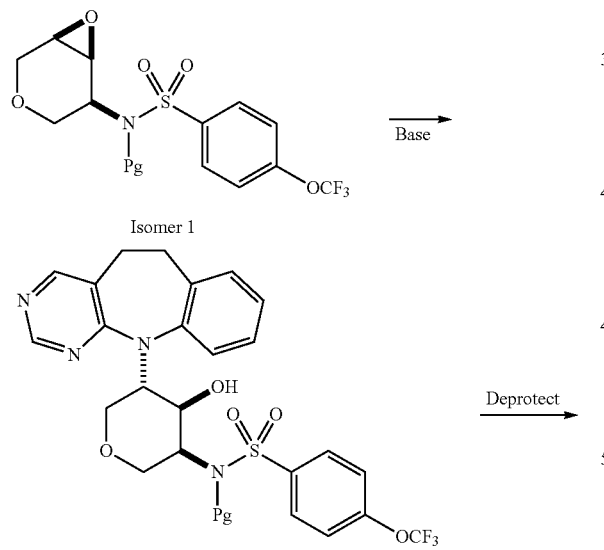

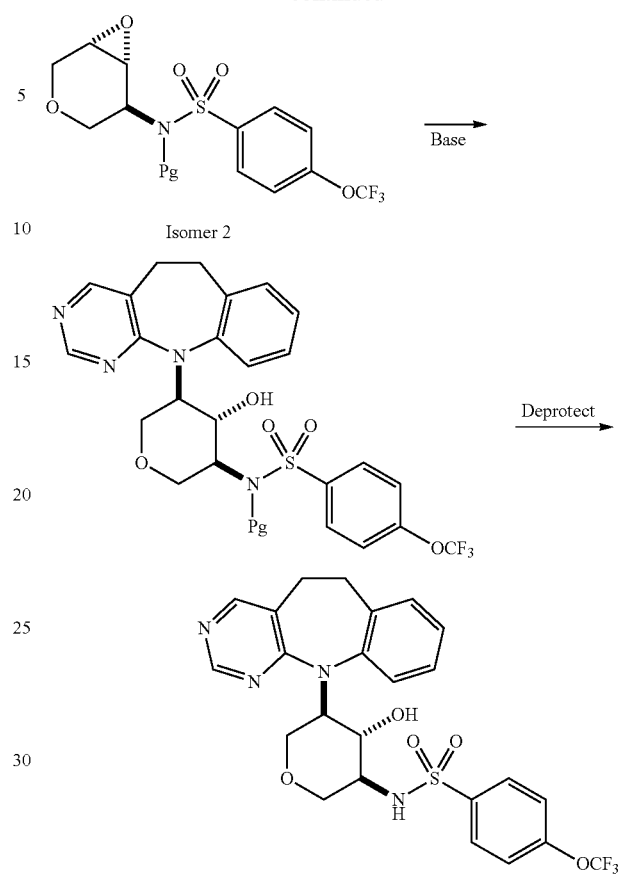

Cyclic Sulfone, Q=SO$_2$

Synthesis of 3,6-dihydro-2H-thiopyran-3-ol is described in Evans et al, J. Am. Chem. Soc. 2000, Vol. 122, Pages 7095-7920. This may be converted to tert-butyl (3,6-dihydro-2H-thiopyran-3-yl) carbonate as already described and used in the synthesis of PP2A modulators in two ways. First as shown in by the example in Scheme 4, where conditions are analogous to those described for the pyran, except that additional oxidant may be employed the dihydroxylation step to effect oxidation of the ring sulfur. Extended reaction times or heating may also be used in the dihydroxylation step.

Scheme 4

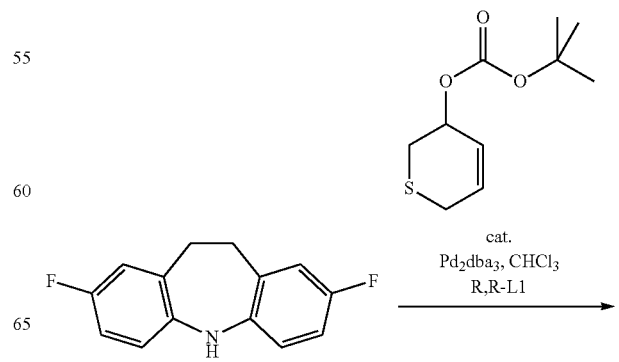

57
-continued
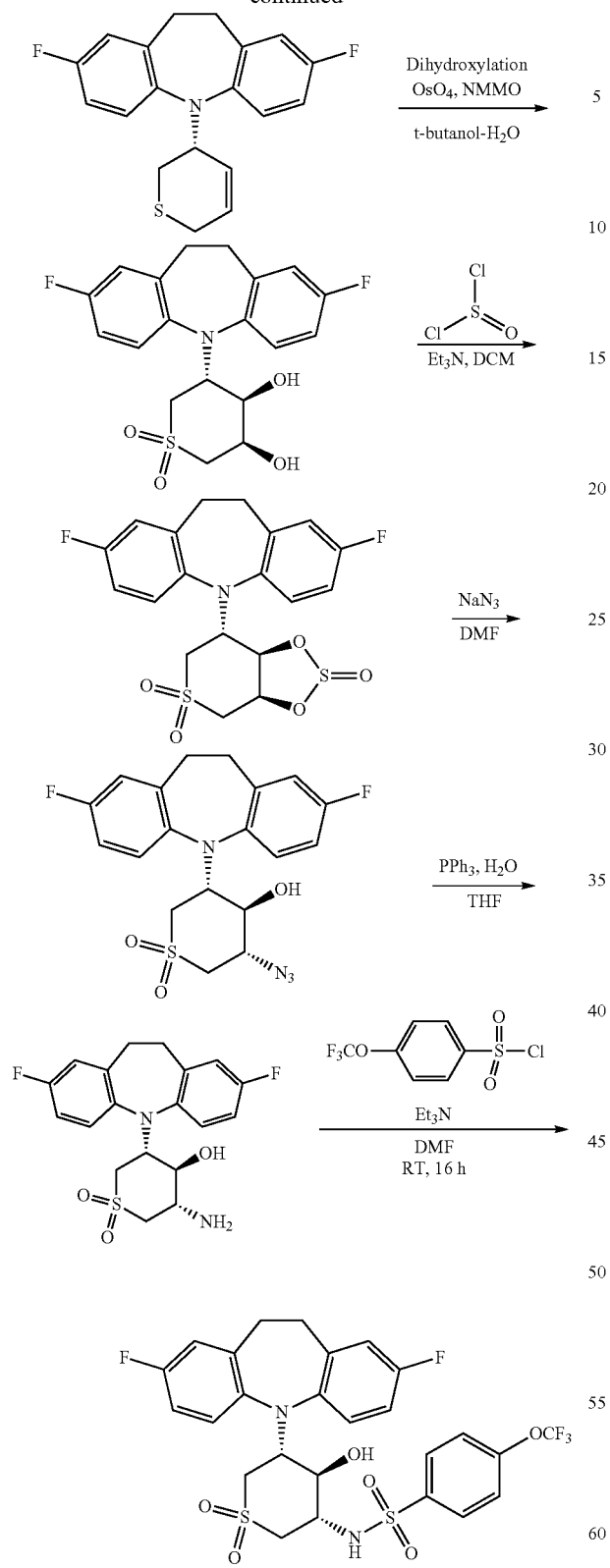
58
Scheme 5
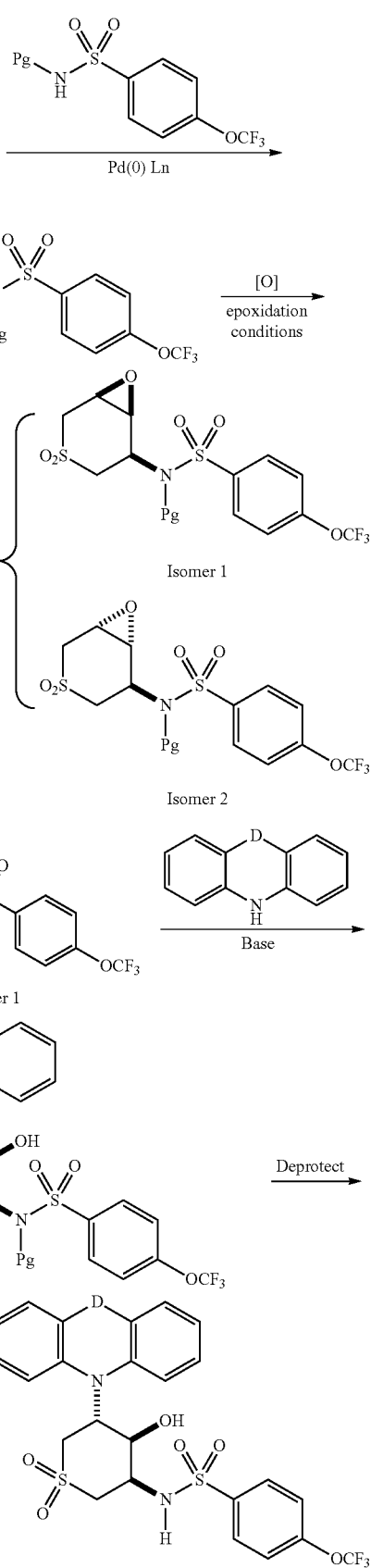
A second route to the cyclic sulfone is shown in Scheme 5; again additional oxidant or extended reaction times may be used in the epoxidation step to effect oxidation of the ring sulfur.

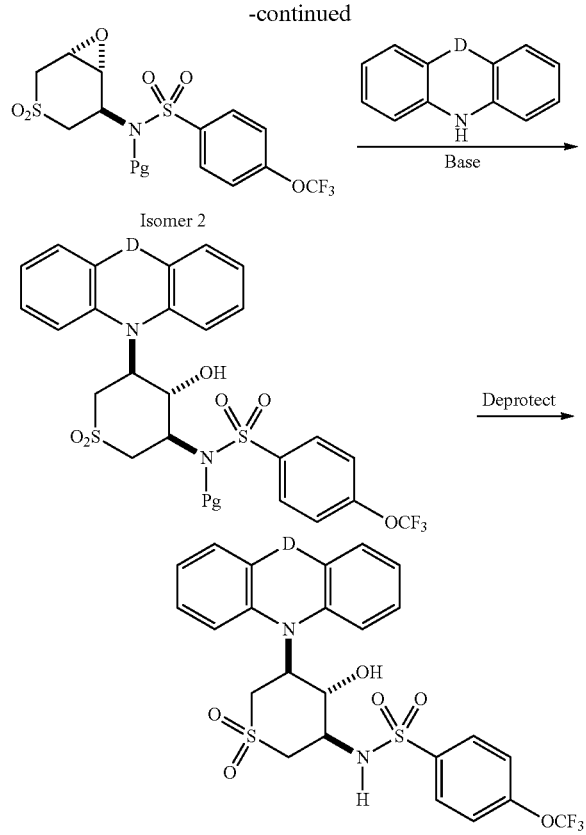

When a single enantiomer is desired, one may employ chromatographic separation of racemic materials by chiral HPLC or one may employ stereoselective synthesis from optically enriched hydroxy heterocycles of known configuration. In addition intermediates in the synthesis may be resolved, then optically enriched material carried forward. For example, racemic diols (XV/XVI) may be resolved by chiral HPLC using CHIRALPAK® IF-3 column, 70:30 hexanes-EtOH, 1 mL/min.

Cell Viability Assays ($IC_{50}$ Determination)

Cell viability assays were performed according to Denizot, F. and R. Lang, Journal of Immunological Methods, 1986. 89(22): p. 271-277. H1650 lung cancer cells were plated at 150,000 cells per well in a 12 well plate. Twenty-four hours after plating, cells were treated as described with increasing concentrations of drug and control. Forty-eight hours after drug treatment, cells were treated with 100 μL of 3-(4,5-Dimethylthiazol-2-yl)-2,5-diphenyltetrazolium bromide (MTT) and incubated for 2 hours at 37 C. The MTT solution was subsequently replaced with 300 μL of n-propyl alcohol and re-aliquoted to a 96 well plate. Spectrophotometric analysis of each solution was performed using a 96 well plate reader at 600 nm in triplicate. Results are shown in Table 1:

TABLE 1

| Cell Viability Data | |
|---|---|
| Example # | $IC_{50}$ (μM) |
| 1 | 15 |

Colony Formation Assay

Protocol for clonogenic assay follows Sangodkar et al., J Clin Invest 2012; 122:2637-51.

Cell culture and staining: For both A549luc and H1650 cells, 500 cells are seeded into each well of a 6-well plate and allowed to attach for 24 hours before drug treatment. The following day, cells are treated with either the appropriate dose of drug or an equivalent volume of DMSO (two replicates are treated for each condition). For each condition, depleted media is replaced with fresh media containing the equivalent drug dose four days after initial treatment. Cells are harvested either 7 (A549luc) or 8 (H1650) days after initial treatment. Briefly, medium is aspirated from each well and the cells are washed twice with ice-cold PBS, then plates are allowed to dry at room temperature for 4 hours. Cells are fixed for one hour in a fixing solution consisting of 10% methanol and 10% glacial acetic acid in distilled water, then stained overnight in 1% (w/v) crystal violet dissolved in methanol. The next day, staining solution is aspirated from the wells and plates are washed gently with distilled water to remove excess stain before colony counting. Colonies are imaged on a ChemiDoc XRS+(Bio-Rad) and images are exported as 8-bit TIFF files. Colonies are counted using the Colony Counter plugin in ImageJ, with colony size defined as between 4 and 400 square pixels, and minimum circularity set at 0.6. Duplicate wells are averaged to obtain a single value for each condition. Results (number of colonies) for A549luc cells and results (number of colonies) for H1650 cells may be analyzed separately.

In Vivo Cancer Model

To assess the in vivo effects of the compounds, subcutaneous xenograft of lung cancer cell line H441 is generated. Cells ($5\times10^6$) are injected into the right flank of 6- to 8-week-old male BALB/c nu/nu mice (Charles River, Wilmington, Mass.). Tumor volume is assessed twice a week by caliper measurement. Mice are randomized to treatment groups based on initial tumor volume average of 100 $mm^3$ per group. Mice are dosed by oral gavage with, for example, 15 mg/kg QD, 15 mg/kg BID, 50 mg/kg QD, or 50 mg/kg BID. Mouse tumors are measured twice a week for the duration of the study. Mouse body weights are recorded weekly and percentage of mice body weights during treatment is calculated as: weight at each time point/initial weight×100. Animals are observed for signs of toxicity (mucous diarrhea, abdominal stiffness and weight loss). Mice undergo treatment for 30 days and are sacrificed 2 hours after the last dose. Tumors are then excised and cut for both formalin-fixation and snap frozen in liquid nitrogen.

Various embodiments of the invention can be described in the text below:

[1]. A compound of formula:

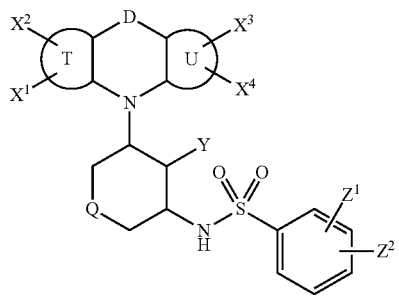

wherein:

D is selected from —S—, —(CH$_2$CH$_2$)—, and —CH=CH—;

T is a benzene ring or a five- or six-membered heteroaromatic ring;

U is a benzene ring or a five- or six-membered heteroaromatic ring;

$X^1$, $X^2$, $X^3$, and $X^4$ are independently selected in each instance from hydrogen, halogen, nitro, cyano, (C$_1$-C$_6$)alkyl, (C$_1$-C$_6$)haloalkyl, (C$_1$-C$_6$)haloalkoxy, (C$_1$-C$_6$)haloalkylthio, —NR$^1$R$^2$, —OR$^1$, —C(O)R$^1$, —OC(O)R$^1$, —C(O)NR$^1$R$^2$, —C(O)OR$^1$, —SR$^1$, —SO$_2$R$^1$, and —SO$_2$NR$^1$R$^2$;

$R^1$ and $R^2$ are independently selected in each instance from the group consisting of hydrogen and (C$_1$-C$_6$)alkyl;

Q is selected from —O—, S(O)$_n$—, and —NR—;

n is zero, 1 or 2;

R is selected from hydrogen; optionally substituted (C$_1$-C$_6$)alkyl, (C$_3$-C$_7$)cycloalkyl, aryl, or heteroaryl; —SO$_2$R$^3$; —SO$_2$NR$^3$R$^4$; —C(=O)R$^5$; —C(=O)OR$^5$; or —C(=O)NR$^3$R$^4$; wherein said substituents on the (C$_1$-C$_6$)alkyl, (C$_3$-C$_7$)cycloalkyl, aryl, or heteroaryl are selected from the group consisting of hydroxy, halogen, cyano, nitro, amino, (C$_1$-C$_4$)alkylamino, (C$_1$-C$_4$)dialkylamino, (C$_1$-C$_4$)acylamino, (C$_1$-C$_4$)alkylsulfonyl, (C$_1$-C$_4$)alkylthio, (C$_1$-C$_4$)alkyl, (C$_3$-C$_7$)cycloalkyl, (C$_1$-C$_4$)haloalkyl, (C$_1$-C$_4$)haloalkoxy, and (C$_1$-C$_4$)alkoxy;

$R^3$ and $R^4$ are independently selected in each instance from hydrogen, (C$_1$-C$_6$)alkyl, aryl, and arylalkyl, wherein said aryl or the aryl of the arylalkyl is optionally substituted with hydroxy, halogen, cyano, nitro, amino, (C$_1$-C$_4$)alkylamino, (C$_1$-C$_4$)dialkylamino, (C$_1$-C$_4$)acylamino, (C$_1$-C$_4$)alkylsulfonyl, (C$_1$-C$_4$)alkylthio, (C$_1$-C$_4$)alkyl, (C$_1$-C$_4$)haloalkyl, (C$_1$-C$_4$)haloalkoxy, or (C$_1$-C$_4$)alkoxy;

$R^5$ is selected from hydrogen, optionally substituted (C$_1$-C$_4$)alkyl, or optionally substituted aryl, wherein said optional substituents are selected from the group consisting of (C$_1$-C$_3$)alkyl, OR$^1$, NH$_2$, NHMe, N(Me)$_2$, and heterocycle;

Y is selected from hydrogen or hydroxyl; and $Z^1$ and $Z^2$ are independently selected in each instance from the group consisting of hydrogen, halogen, nitro, cyano, azide, (C$_1$-C$_6$)alkyl, (C$_1$-C$_6$)haloalkyl, (C$_1$-C$_6$)haloalkoxy, —NR$^1$R$^2$, —NR$^1$C(O)R$^2$, —OR$^1$, —C(O)R$^1$, —OC(O)R$^1$, —C(O)NR$^1$R$^2$, —C(O)OR$^1$, —SR$^1$, —SO$_2$R$^1$, and —SO$_2$NR$^1$R$^2$.

[2]. A compound of [1] above, or according to other embodiments of the invention, wherein D is —S—.

[3]. A compound of [1] above, or according to other embodiments of the invention, wherein D is —(CH$_2$CH$_2$)—.

[4]. A compound of [1] above, or according to other embodiments of the invention, wherein T and U are each independently selected from the group consisting of a benzene ring and pyridine.

[5]. A compound of [4] above, or according to other embodiments of the invention, wherein at least one of T and U is a benzene ring.

[6]. A compound of [5] above, or according to other embodiments of the invention, wherein both T and U are benzene rings.

[7]. A compound of [1], [2], [3], [4], [5], or [6] above, or according to other embodiments of the invention, wherein Y is hydroxyl.

[8]. A compound of [1], [2], [3], [4], [5], or [6] above, or according to other embodiments of the invention, wherein Y is hydrogen.

[9]. A compound of [1], [2], [3], [4], [5], or [6] above, or according to other embodiments of the invention, wherein Q is —NR—.

[10]. A compound of [9] above, or according to other embodiments of the invention, wherein R is selected from hydrogen; (C$_1$-C$_6$)alkyl optionally substituted with one or more of hydroxy, fluoro, or (C$_3$-C$_7$)cycloalkyl; (C$_3$-C$_7$)cycloalkyl optionally substituted with one or more of hydroxy, methyl, or fluoro; aryl optionally substituted with one or more of hydroxy, methoxy, halogen, (C$_1$-C$_3$)haloalkyl, nitro, amino, or methyl; heteroaryl optionally substituted with one or more of hydroxy, methoxy, halogen, (C$_1$-C$_3$)haloalkyl, nitro, amino, or methyl; —SO$_2$R$^3$; —SO$_2$NR$^3$R$^4$; —C(=O)R$^5$; —C(=O)OR$^5$; or —C(=O)NR$^3$R$^4$;

$R^3$ is selected in each instance from hydrogen, (C$_1$-C$_6$)alkyl, (C$_1$-C$_6$)haloalkyl, aryl, and arylalkyl, wherein said aryl or the aryl of the arylalkyl is optionally substituted with one or more of hydroxy, halogen, cyano, nitro, amino, (C$_1$-C$_4$)alkylamino, (C$_1$-C$_4$)dialkylamino, (C$_1$-C$_4$)acylamino, (C$_1$-C$_4$)alkylsulfonyl, (C$_1$-C$_4$)alkylthio, (C$_1$-C$_4$)alkyl, (C$_1$-C$_4$)haloalkyl, (C$_1$-C$_4$)haloalkoxy, and (C$_1$-C$_4$)alkoxy;

$R^4$ is selected in each instance from hydrogen and methyl;

$R^5$ is selected from optionally substituted (C$_1$-C$_4$)alkyl or optionally substituted aryl, wherein said optional substituents are selected from one or more of OH, OMe, NH$_2$, NHMe, N(Me)$_2$, or heterocycle.

[11]. A compound of [10] above, or according to other embodiments of the invention, wherein R is selected from hydrogen; (C$_1$-C$_3$)alkyl optionally substituted with one or more of hydroxy or fluoro; (C$_3$-C$_7$)cycloalkyl optionally substituted with one or more of hydroxy, methyl, or fluoro; phenyl optionally substituted with one or more of hydroxy, chloro, fluoro, methoxy, nitro, amino, trifluoromethyl, or methyl; or a nitrogen-containing heteroaryl optionally substituted with one or two methyl groups.

[12]. A compound of [9] above, or according to other embodiments of the invention, wherein R is —C(=O)R$^5$.

[13]. A compound of [12] above, or according to other embodiments of the invention, wherein $R^5$ is selected from methyl, optionally substituted with OR$^1$, NH$_2$, NHMe, N(Me)$_2$, and heterocycle.

[14]. A compound of [9] above, or according to other embodiments of the invention, wherein R is —C(=O)OR$^5$.

[15]. A compound of [14] above, or according to other embodiments of the invention, wherein $R^5$ is selected from the group consisting of phenyl and (C$_1$-C$_4$)alkyl, each of which may be substituted with OR.

[16]. A compound of [9] above, or according to other embodiments of the invention, wherein R is —SO$_2$R$^3$.

[17]. A compound of [16] above, or according to other embodiments of the invention, wherein $R^3$ is selected from the group consisting of hydrogen, (C$_1$-C$_6$)alkyl, and aryl; wherein said aryl is optionally substituted with hydroxy, halogen, cyano, amino, or (C$_1$-C$_4$)alkoxy.

[18]. A compound of [9] above, or according to other embodiments of the invention, wherein R is SO$_2$NR$^3$R$^4$.

[19]. A compound of [18] above, or according to other embodiments of the invention, wherein $R^3$ is selected from the group consisting of hydrogen, (C$_1$-C$_3$)alkyl, and optionally substituted aryl; and $R^4$ is hydrogen or methyl.

[20]. A compound of [9] above, or according to other embodiments of the invention, wherein R is —C(=O)NR$^3$R$^4$.

[21]. A compound of [20] above, or according to other embodiments of the invention, wherein $R^3$ is selected from the group consisting of hydrogen, (C$_1$-C$_3$)alkyl, and aryl optionally substituted with hydroxy, halogen, cyano, amino, or methoxy; and R$^4$ is hydrogen or methyl.

[22]. A compound of [1], [2], [3], [4], [5], or [6] above, or according to other embodiments of the invention, wherein Q is —O—.

[23]. A compound of [1], [2], [3], [4], [5], or [6] above, or according to other embodiments of the invention, wherein zero, one or two of X$^1$, X$^2$, X$^3$, and X$^4$ are independently selected in each instance from halogen and (C$_1$-C$_6$)haloalkyl, and the remainder are hydrogen.

[24]. A compound of [23] above, or according to other embodiments of the invention, wherein zero, one or two of X$^1$, X$^2$, X$^3$, and X$^4$ are independently selected in each instance from chloro, fluoro, and (C$_1$-C$_3$)fluoroalkyl, and the remainder are hydrogen.

[25]. A compound of [1], [2], [3], [4], [5], or [6] above, or according to other embodiments of the invention, wherein Z$^1$ and Z$^2$ are independently selected in each instance from hydrogen, halogen, (C$_1$-C$_6$)haloalkyl, (C$_1$-C$_6$)alkoxy, and (C$_1$-C$_6$)haloalkoxy.

[26]. A compound of [25] above, or according to other embodiments of the invention, wherein Z$^1$ is hydrogen and Z$^2$ is selected from hydrogen, halogen, (C$_1$-C$_6$)haloalkyl, (C$_1$-C$_6$)alkoxy, and (C$_1$-C$_6$)haloalkoxy.

[27]. A compound of [26] above, or according to other embodiments of the invention, wherein Z$^2$ is hydrogen, fluoro, chloro, trifluoromethyl, methoxy, or trifluoromethoxy.

[28]. A compound of [27] above, or according to other embodiments of the invention, wherein Z$^2$ is para to the attachment of the phenyl ring to the sulfonyl.

[29]. A compound of [1], [2], [3], [4], [5], or [6] above, or according to other embodiments of the invention, wherein the relative stereochemistry is of formula II:

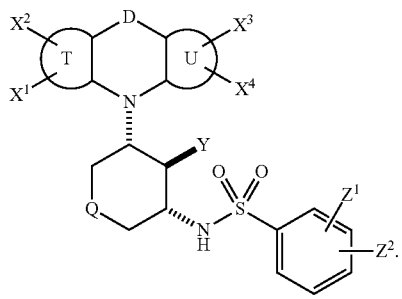

[30]. A compound of [29] above, or according to other embodiments of the invention, of formula IIIa:

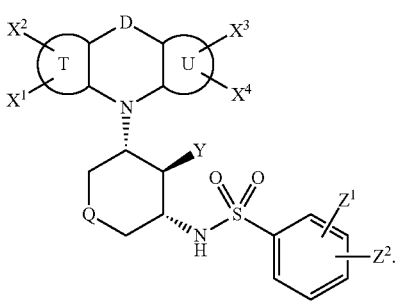

[31]. A compound of [29] above, or according to other embodiments of the invention, of formula IIIb:

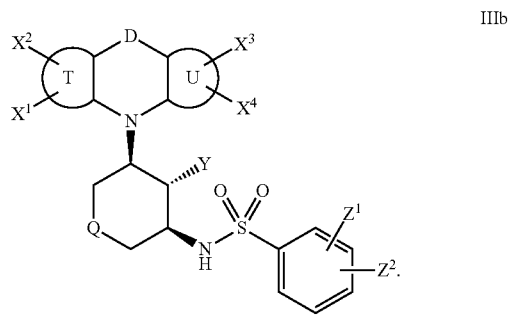

[32]. A compound of [1] above, or according to other embodiments of the invention, of formula

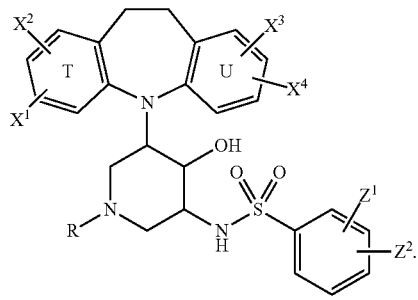

[33]. A compound of [1] above, or according to other embodiments of the invention, of formula:

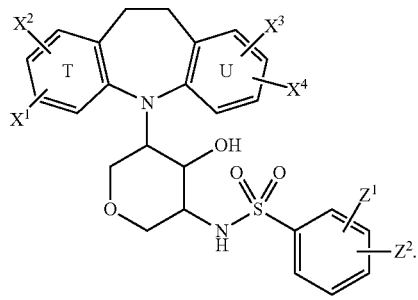

[34]. A compound of [1] above, or according to other embodiments of the invention, of formula:

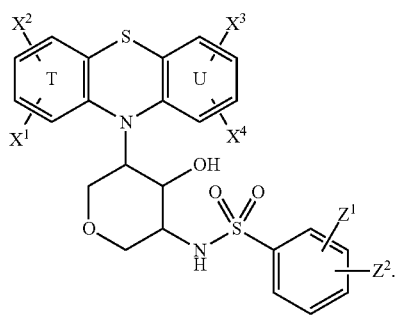

[35]. A compound of [1] above, or according to other embodiments of the invention, of formula:

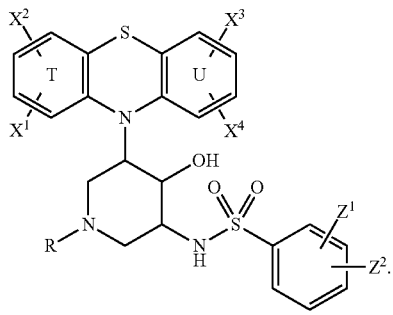

[36]. A compound of [32], [33], [34], or [35] above, or according to other embodiments of the invention, wherein $Z^1$ is hydrogen and $Z^2$ is selected from hydrogen, halogen, $(C_1-C_5)$haloalkyl, $(C_1-C_6)$alkoxy, or $(C_1-C_6)$haloalkoxy.

[37]. A compound of [36] above, or according to other embodiments of the invention, wherein $Z^2$ is hydrogen, fluoro, chloro, trifluoromethyl, methoxy, or trifluoromethoxy.

[38]. A compound of [37] above, or according to other embodiments of the invention, wherein $Z^2$ is trifluoromethoxy.

Various embodiments of the invention can be described in the text below:

[101]. A compound of formula (I):

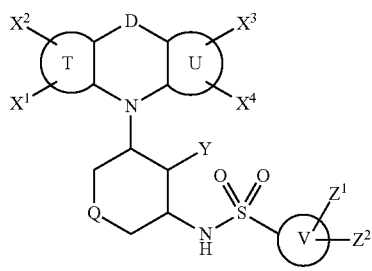

wherein:

D is selected from —S—, —(CH$_2$CH$_2$)—, and —CH═CH—;

T is a benzene ring or a five- or six-membered heteroaromatic ring;

U is a benzene ring or a five- or six-membered heteroaromatic ring;

$X^1$, $X^2$, $X^3$, and $X^4$ are independently selected in each instance from hydrogen, halogen, nitro, cyano, $(C_1-C_6)$alkyl, $(C_1-C_6)$haloalkyl, $(C_1-C_6)$haloalkoxy, $(C_1-C_6)$haloalkylthio, —NR$^1$R$^2$, —OR$^1$, —C(O)R$^1$, —OC(O)R$^1$, —C(O)NR$^1$R$^2$, —C(O)OR$^1$, —SR, —SO$_2$R$^1$, and —SO$_2$NR$^1$R$^2$;

$R^1$ and $R^2$ are independently selected in each instance from the group consisting of hydrogen and $(C_1-C_6)$alkyl;

Q is selected from —O—, S(O)$_n$—, and —NR—;

n is zero, 1 or 2;

R is selected from hydrogen; optionally substituted $(C_1-C_6)$alkyl, $(C_3-C_7)$cycloalkyl, aryl, or heteroaryl; —SO$_2$R$^3$; —SO$_2$NR$^3$R$^4$; —C(═O)R$^5$; —C(═O)OR$^5$; or —C(═O)NR$^3$R$^4$; wherein said substituents on the $(C_1-C_6)$alkyl, $(C_3-C_7)$cycloalkyl, aryl, or heteroaryl are selected from the group consisting of hydroxy, halogen, cyano, nitro, amino, $(C_1-C_4)$alkylamino, $(C_1-C_4)$dialkylamino, $(C_1-C_4)$acylamino, $(C_1-C_4)$alkylsulfonyl, $(C_1-C_4)$alkylthio, $(C_1-C_4)$alkyl, $(C_3-C_7)$cycloalkyl, $(C_1-C_4)$haloalkyl, $(C_1-C_4)$haloalkoxy, and $(C_1-C_4)$alkoxy;

$R^3$ and $R^4$ are independently selected in each instance from hydrogen, $(C_1-C_6)$alkyl, aryl, and arylalkyl, wherein said aryl or the aryl of the arylalkyl is optionally substituted with hydroxy, halogen, cyano, nitro, amino, $(C_1-C_4)$alkylamino, $(C_1-C_4)$dialkylamino, $(C_1-C_4)$acylamino, $(C_1-C_4)$alkylsulfonyl, $(C_1-C_4)$alkylthio, $(C_1-C_4)$alkyl, $(C_1-C_4)$haloalkyl, $(C_1-C_4)$haloalkoxy, or $(C_1-C_4)$alkoxy;

$R^5$ is selected from hydrogen, optionally substituted $(C_1-C_4)$alkyl, or optionally substituted aryl, wherein said optional substituents are selected from the group consisting of $(C_1-C_3)$alkyl, OR$^1$, NH$_2$, NHMe, N(Me)$_2$, and heterocycle;

Y is selected from hydrogen or hydroxyl;

V is selected from phenyl, a six-membered heteroaromatic ring, furan, and thiophene;

$Z^1$ and $Z^2$ are independently selected in each instance from the group consisting of hydrogen, halogen, nitro, cyano, azide, $(C_1-C_6)$alkyl, $(C_1-C_6)$haloalkyl, $(C_1-C_6)$haloalkoxy, —NR$^1$R$^2$, —NR$^1$C(O)R$^2$, —NR$^1$C(O)OR$^6$, —OR$^1$, —C(O)R$^1$, —OC(O)R$^1$, —C(O)NR$^1$R$^2$, —C(O)OR$^1$, —SR$^1$, —SO$_2$R$^1$, and —SO$_2$NR$^1$R$^2$; and $R^6$ is $(C_1-C_8)$hydrocarbon.

[102]. A compound of [101] above, or according to other embodiments of the invention, wherein D is —S—.

[103]. A compound of [101] above, or according to other embodiments of the invention, wherein D is —(CH$_2$CH$_2$)—.

[104]. A compound of [101] above, or according to other embodiments of the invention, wherein T and U are each independently selected from the group consisting of a benzene ring and pyridine.

[105]. A compound of [104] above, or according to other embodiments of the invention, wherein at least one of T and U is a benzene ring.

[106]. A compound of [105] above, or according to other embodiments of the invention, wherein both T and U are benzene rings.

[107]. A compound of [101], [102], [103], [104], [105], or [106] above, or according to other embodiments of the invention, wherein Y is hydroxyl.

[108]. A compound of [101], [102], [103], [104], [105], or [106] above, or according to other embodiments of the invention, wherein Y is hydrogen.

[109]. A compound of [101], [102], [103], [104], [105], or [106] above, or according to other embodiments of the invention, wherein Q is —NR—.

[110]. A compound of [109] above, or according to other embodiments of the invention, wherein R is selected from hydrogen; $(C_1-C_6)$alkyl optionally substituted with one or more of hydroxy, fluoro, or $(C_3-C_7)$cycloalkyl; $(C_3-C_7)$cycloalkyl optionally substituted with one or more of hydroxy, methyl, or fluoro; aryl optionally substituted with one or more of hydroxy, methoxy, halogen, $(C_1-C_3)$haloalkyl, nitro, amino, or methyl; heteroaryl optionally substituted with one or more of hydroxy, methoxy, halogen, $(C_1-C_3)$haloalkyl, nitro, amino, or methyl; —SO$_2$R$^3$; —SO$_2$NR$^3$R$^4$; —C(═O)R$^5$; —C(═O)OR$^5$; or —C(═O)NR$^3$R$^4$;

$R^3$ is selected in each instance from hydrogen, $(C_1-C_6)$alkyl, $(C_1-C_6)$haloalkyl, aryl, and arylalkyl, wherein said aryl or the aryl of the arylalkyl is optionally substituted with one or more of hydroxy, halogen, cyano, nitro, amino, $(C_1-C_4)$alkylamino, $(C_1-C_4)$dialkylamino, $(C_1-C_4)$acylamino, $(C_1-C_4)$alkylsulfonyl, $(C_1-C_4)$alkylthio, $(C_1-C_4)$alkyl, $(C_1-C_4)$haloalkyl, $(C_1-C_4)$haloalkoxy, and $(C_1-C_4)$alkoxy;

$R^4$ is selected in each instance from hydrogen and methyl;

$R^5$ is selected from optionally substituted $(C_1-C_4)$alkyl or optionally substituted aryl, wherein said optional substituents are selected from one or more of $OR^1$, $NH_2$, NHMe, $N(Me)_2$, or heterocycle.

[111]. A compound of [110] above, or according to other embodiments of the invention, wherein R is selected from hydrogen; $(C_1-C_3)$alkyl optionally substituted with one or more of hydroxy or fluoro; $(C_3-C_7)$cycloalkyl optionally substituted with one or more of hydroxy, methyl, or fluoro; phenyl optionally substituted with one or more of hydroxy, chloro, fluoro, methoxy, nitro, amino, trifluoromethyl, or methyl; or a nitrogen-containing heteroaryl optionally substituted with one or two methyl groups.

[112]. A compound of [109] above, or according to other embodiments of the invention, wherein R is —C(=O)$R^5$.

[113]. A compound of [112] above, or according to other embodiments of the invention, wherein $R^5$ is selected from methyl, optionally substituted with $OR^1$, $NH_2$, NHMe, $N(Me)_2$, and heterocycle.

[114]. A compound of [109] above, or according to other embodiments of the invention, wherein R is —C(=O)$OR^5$.

[115]. A compound of [114] above, or according to other embodiments of the invention, wherein $R^5$ is selected from the group consisting of phenyl and $(C_1-C_4)$alkyl, each of which may be substituted with $OR^1$.

[116]. A compound of [109] above, or according to other embodiments of the invention, wherein R is —$SO_2R^3$.

[117]. A compound of [116] above, or according to other embodiments of the invention, wherein $R^3$ is selected from the group consisting of hydrogen, $(C_1-C_6)$alkyl, and aryl; wherein said aryl is optionally substituted with hydroxy, halogen, cyano, amino, or $(C_1-C_4)$alkoxy.

[118]. A compound of [109] above, or according to other embodiments of the invention, wherein R is $SO_2NR^3R^4$.

[119]. A compound of [118] above, or according to other embodiments of the invention, wherein $R^3$ is selected from the group consisting of hydrogen, $(C_1-C_3)$alkyl, and optionally substituted aryl; and $R^4$ is hydrogen or methyl.

[120]. A compound of [109] above, or according to other embodiments of the invention, wherein R is —C(=O)$NR^3R^4$.

[121]. A compound of [120] above, or according to other embodiments of the invention, wherein $R^3$ is selected from the group consisting of hydrogen, $(C_1-C_3)$alkyl, and aryl optionally substituted with hydroxy, halogen, cyano, amino, or methoxy; and $R^4$ is hydrogen or methyl.

[122]. A compound of [101], [102], [103], [104], [105], or [106] above, or according to other embodiments of the invention, wherein Q is —O—.

[123]. A compound of [101], [102], [103], [104], [105], or [106] above, or according to other embodiments of the invention, wherein zero, one or two of $X^1$, $X^2$, $X^3$, and $X^4$ are independently selected in each instance from halogen and $(C_1-C_6)$haloalkyl, and the remainder are hydrogen.

[124]. A compound of [123] above, or according to other embodiments of the invention, wherein zero, one or two of $X^1$, $X^2$, $X^3$, and $X^4$ are independently selected in each instance from chloro, fluoro, and $(C_1-C_3)$fluoroalkyl, and the remainder are hydrogen.

[125]. A compound of [101], [102], [103], [104], [105], or [106] above, or according to other embodiments of the invention, wherein $Z^1$ and $Z^2$ are independently selected in each instance from hydrogen, halogen, $(C_1-C_6)$haloalkyl, —$NR^1C(O)OR^6$, $(C_1-C_6)$alkoxy, and $(C_1-C_6)$haloalkoxy.

[126]. A compound of [125] above, or according to other embodiments of the invention, wherein $Z^1$ is hydrogen and $Z^2$ is selected from hydrogen, halogen, $(C_1-C_6)$haloalkyl, —$NR^1C(O)OR^6$, $(C_1-C_6)$alkoxy, and $(C_1-C_6)$haloalkoxy.

[127]. A compound of [126] above, or according to other embodiments of the invention, wherein $Z^2$ is hydrogen, fluoro, chloro, trifluoromethyl, —NHBoc, methoxy, or trifluoromethoxy.

[128]. A compound of [127] above, or according to other embodiments of the invention, wherein $Z^2$ is para to the attachment of the ring to the sulfonyl.

[129]. A compound of [101], [102], [103], [104], [105], or [106] above, or according to other embodiments of the invention, wherein the relative stereochemistry is of formula IIa or IIb:

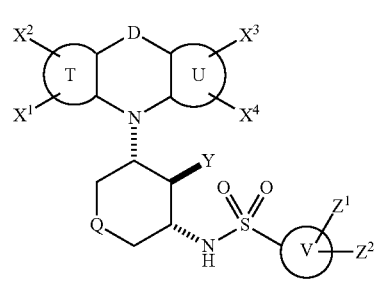

IIa

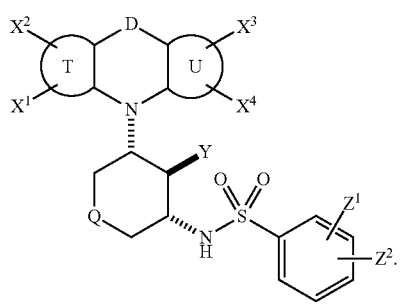

IIb

[130]. A compound of [129] above, or according to other embodiments of the invention, of formula IIIa or IIIb:

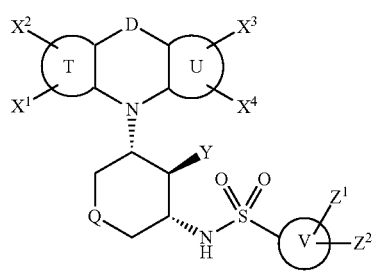

IIIa

-continued
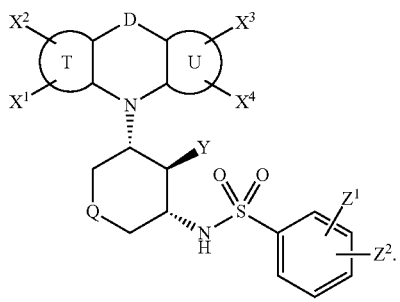
IIIb
[131]. A compound of [129] above, or according to other embodiments of the invention, of formula IIIc or IIId:
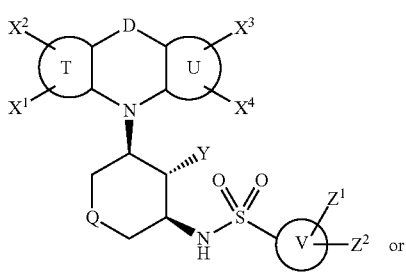
IIIc
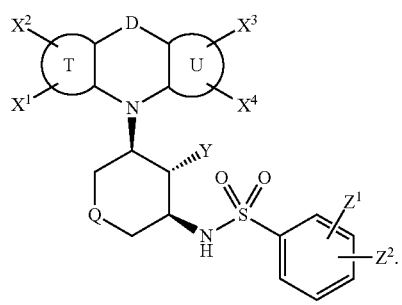
IIId
[132]. A compound according to claim 1 of formula
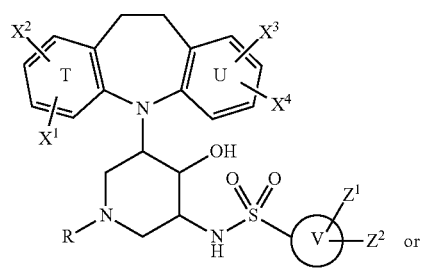
-continued
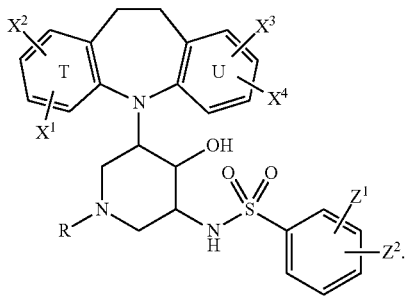
[133]. A compound according to claim 1 of formula:
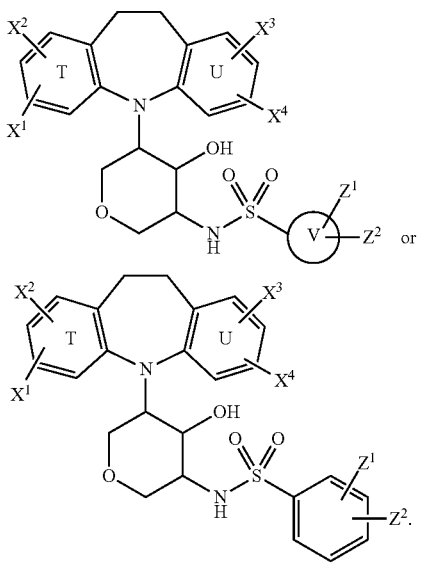
[134]. A compound according to claim 1 of formula:
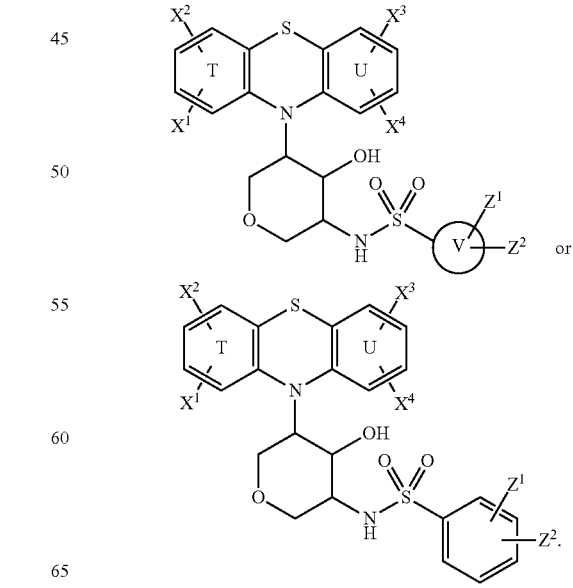

[135]. A compound according to claim 1 of formula:

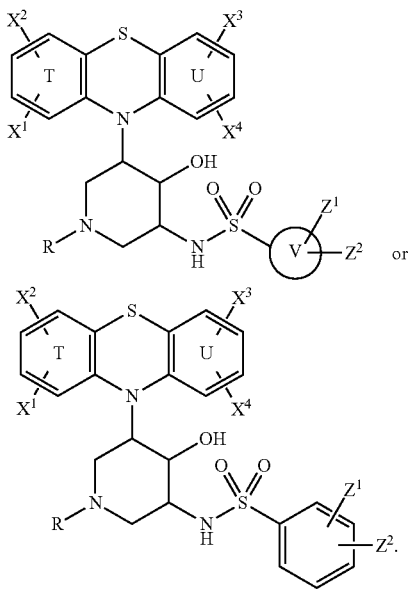

[136]. A compound of [132], [133], [134], or [135] above, or according to other embodiments of the invention, wherein $Z^1$ is hydrogen and $Z^2$ is selected from hydrogen, halogen, $(C_1-C_6)$haloalkyl, $(C_1-C_6)$alkoxy, or $(C_1-C_6)$haloalkoxy.
[137]. A compound according to claim 36 wherein $Z^2$ is hydrogen, fluoro, chloro, trifluoromethyl, methoxy, or trifluoromethoxy.
[138]. A compound according to claim 37 wherein $Z^2$ is trifluoromethoxy.
[139]. A compound according to any one of the above claims, wherein V is phenyl.
[140]. A method for treating a disease in a patient chosen from:
 (a) cancer
 (b) diabetes
 (c) autoimmune disease
 (d) age onset proteotoxic disease
 (e) mood disorder
 (f) acne vulgaris
 (g) solid organ transplant rejection
 (h) graft vs. host disease
 (i) cardiac hypertrophy
 (j) viral infection and
 (k) parasitic infection;
the method comprising administering to the patient a therapeutically effective amount of a compound of any one of [101] to [139] above, or according to other embodiments of the invention.
[141]. The method of [140] above, or according to other embodiments of the invention, wherein said cancer is selected from the group consisting of: ovarian, pancreatic, renal cell, breast, prostate, lung, hepatocellular carcinoma, glioma, leukemia, lymphoma, colorectal cancers, and sarcomas.
[142]. The method of [140] above, or according to other embodiments of the invention, for treating cancer, wherein said cancer is chemotherapy resistant cancer.
[143]. The method of [142] above, or according to other embodiments of the invention, wherein the method further comprises administering one or more additional cancer chemotherapeutic agents.

[144]. The method of [109] above, or according to other embodiments of the invention, for treating an age onset proteotoxic disease, wherein said disease is selected from the group consisting of: Alzheimer's disease, Parkinson's disease, Huntington's disease, and amyotrophic lateral sclerosis.
[145]. The method of [140] above, or according to other embodiments of the invention, for treating a viral infection.
[146]. The method of [145] above, or according to other embodiments of the invention, wherein said viral infection is caused by a virus selected from the group consisting of influenza, HIV-1, HPV, adenovirus, BKV, EBV, JCV, HCV, MCV, polyomavirus, SV40, HTLV-1, HSV-1, CMV, hepatitis B, BPV-1, human T-cell lymphotropic virus type 1, Japanese encephalitis virus, RSV, and West Nile virus.
[147]. The method of [140] above, or according to other embodiments of the invention, for treating a parasitic infection.
[148]. The method of [147] above, or according to other embodiments of the invention, wherein said parasitic infection is caused by a parasite selected from the group consisting of *Plasmodium* and *Theileria*.
[149]. A method for restoring sensitivity to one or more chemotherapeutic agents in the treatment of cancer, the method comprising administering an effective amount of a compound of any one of [101] to [139] above, or according to other embodiments of the invention.
[150]. A method for treating a disease or disorder in a patient where the disease or disorder involves the dysregulation of the PI3K-AKT-FOXO signaling pathway, the method comprising administering to the patient a therapeutically effective amount of a compound of any one of [101] to [139] above, or according to other embodiments of the invention.
[151]. A method for treating a disease or disorder in a patient where the disease or disorder involves the dysregulation of a Myc dependent signaling pathway, the method comprising administering to the patient a therapeutically effective amount of a compound of any one of [101] to [139] above, or according to other embodiments of the invention.
[152]. A pharmaceutical composition comprising a pharmaceutically acceptable carrier and a compound of any one of [101] to [139] above, or according to other embodiments of the invention.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

We claim:
1. A compound of formula (I):

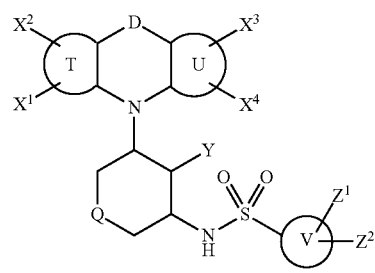

wherein:
D is selected from —S—, —(CH$_2$CH$_2$)—, and —CH=CH—;
T is a benzene ring or a five- or six-membered heteroaromatic ring;
U is a benzene ring or a five- or six-membered heteroaromatic ring;
X$^1$, X$^2$, X$^3$, and X$^4$ are independently selected in each instance from hydrogen, halogen, nitro, cyano, (C$_1$-C$_6$)alkyl, (C$_1$-C$_6$)haloalkyl, (C$_1$-C$_6$)haloalkoxy, (C$_1$-C$_6$)haloalkylthio, —NR$^1$R$^2$, —OR$^1$, —C(O)R$^1$, —OC(O)R, —C(O)NR$^1$R$^2$, —C(O)OR, —SR$^1$, —SO$_2$R$^1$, and —SO$_2$NR$^1$R$^2$;
R$^1$ and R$^2$ are independently selected in each instance from the group consisting of hydrogen and (C$_1$-C$_6$)alkyl;
Q is selected from —O—, S(O)$_n$—, and —NR—;
n is zero, 1 or 2;
R is selected from hydrogen; optionally substituted (C$_1$-C$_6$)alkyl, (C$_3$-C$_7$)cycloalkyl, aryl, or heteroaryl; —SO$_2$R$^3$; —SO$_2$NR$^3$R$^4$; —C(=O)R$^5$; —C(=O)OR$^5$; or —C(=O)NR$^3$R$^4$; wherein said substituents on the (C$_1$-C$_6$)alkyl, (C$_3$-C$_7$)cycloalkyl, aryl, or heteroaryl are selected from the group consisting of hydroxy, halogen, cyano, nitro, amino, (C$_1$-C$_4$)alkylamino, (C$_1$-C$_4$)dialkylamino, (C$_1$-C$_4$)acylamino, (C$_1$-C$_4$)alkylsulfonyl, (C$_1$-C$_4$)alkylthio, (C$_1$-C$_4$)alkyl, (C$_3$-C$_7$)cycloalkyl, (C$_1$-C$_4$)haloalkyl, (C$_1$-C$_4$)haloalkoxy, and (C$_1$-C$_4$)alkoxy;
R$^3$ and R$^4$ are independently selected in each instance from hydrogen, (C$_1$-C$_6$)alkyl, aryl, and arylalkyl, wherein said aryl or the aryl of the arylalkyl is optionally substituted with hydroxy, halogen, cyano, nitro, amino, (C$_1$-C$_4$)alkylamino, (C$_1$-C$_4$)dialkylamino, (C$_1$-C$_4$)acylamino, (C$_1$-C$_4$)alkylsulfonyl, (C$_1$-C$_4$)alkylthio, (C$_1$-C$_4$)alkyl, (C$_1$-C$_4$)haloalkyl, (C$_1$-C$_4$)haloalkoxy, or (C$_1$-C$_4$)alkoxy;
R$^5$ is selected from hydrogen, optionally substituted (C$_1$-C$_4$)alkyl, or optionally substituted aryl, wherein said optional substituents are selected from the group consisting of (C$_1$-C$_3$)alkyl, OR$^1$, NH$_2$, NHMe, N(Me)$_2$, and heterocycle;
Y is selected from hydrogen or hydroxyl;
V is selected from phenyl, a six-membered heteroaromatic ring, furan, and thiophene;
Z$^1$ and Z$^2$ are independently selected in each instance from the group consisting of hydrogen, halogen, nitro, cyano, azide, (C$_1$-C$_6$)alkyl, (C$_1$-C$_6$)haloalkyl, (C$_1$-C$_6$)haloalkoxy, —NR$^1$R$^2$, —NR$^1$C(O)R$^2$, —NR$^1$C(O)OR$^6$, —OR$^1$, —C(O)R$^1$, —OC(O)R$^1$, —C(O)NR$^1$R$^2$, —C(O)OR$^1$, —SR$^1$, —SO$_2$R$^1$, and —SO$_2$NR$^1$R$^2$; and
R$^6$ is (C$_1$-C$_8$)hydrocarbon.

2. A compound according to claim 1 wherein D is —S—.
3. A compound according to claim 1 wherein D is —(CH$_2$CH$_2$)—.
4. A compound according to claim 1 wherein T and U are each independently selected from the group consisting of a benzene ring and pyridine.
5. A compound according to claim 1 wherein Y is hydroxyl.
6. A compound according to claim 1 wherein Q is —NR—.
7. A compound according to claim 6 wherein R is selected from hydrogen; (C$_1$-C$_3$)alkyl optionally substituted with one or more of hydroxy or fluoro; (C$_3$-C$_7$)cycloalkyl optionally substituted with one or more of hydroxy, methyl, or fluoro; phenyl optionally substituted with one or more of hydroxy, chloro, fluoro, methoxy, nitro, amino, trifluoromethyl, or methyl; or a nitrogen-containing heteroaryl optionally substituted with one or two methyl groups.

8. A compound according to claim 1 wherein Q is —O—.

9. A compound according to claim 1 wherein zero, one or two of X$^1$, X$^2$, X$^3$, and X$^4$ are independently selected in each instance from halogen and (C$_1$-C$_6$)haloalkyl, and the remainder are hydrogen.

10. A compound according to claim 1 wherein Z$^1$ is hydrogen and Z$^2$ is selected from hydrogen, halogen, (C$_1$-C$_6$)haloalkyl, —NR$^1$C(O)OR$^6$, (C$_1$-C$_6$)alkoxy, and (C$_1$-C$_6$)haloalkoxy.

11. A compound according to claim 1 wherein the relative stereochemistry is of formula IIa or IIb:

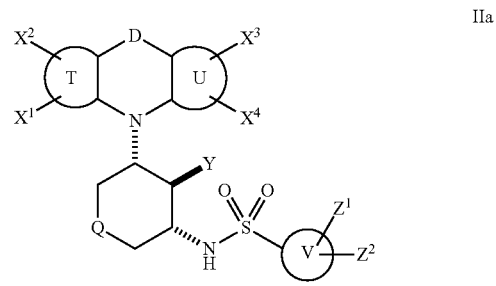

IIa

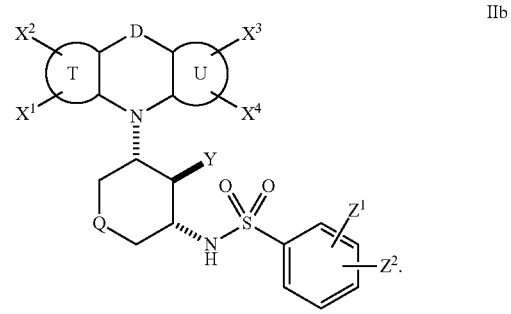

IIb

12. A compound according to claim 1 of formula

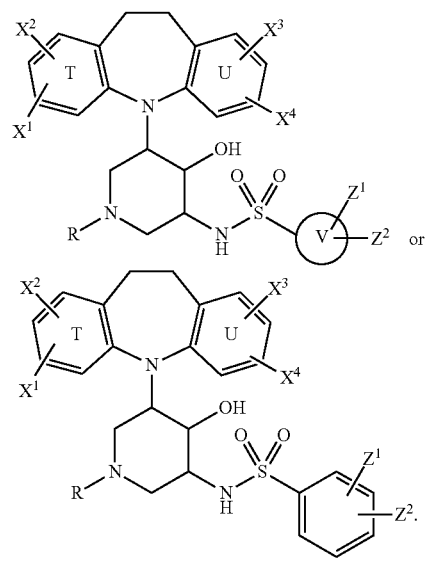

13. A compound according to claim 1 of formula:

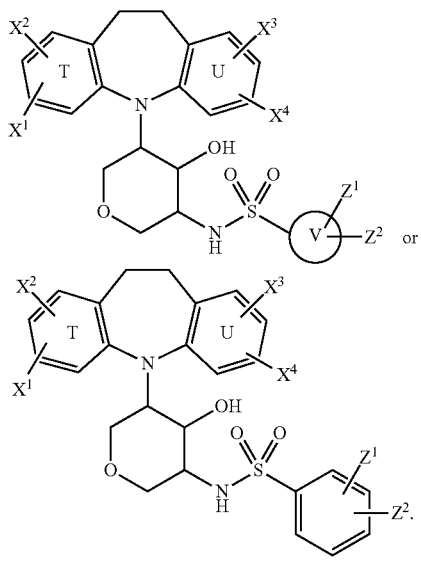

14. A compound according to claim 1 of formula:

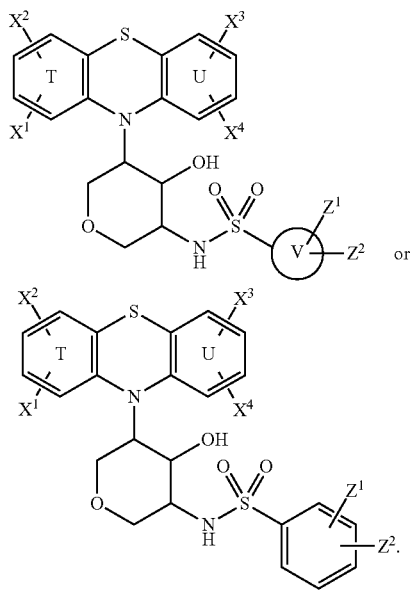

15. A compound according to claim 1 of formula:

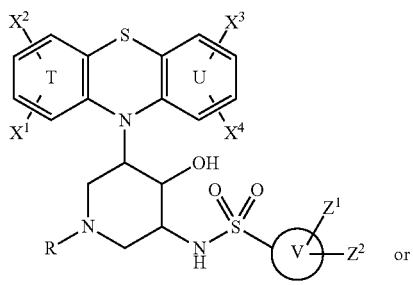

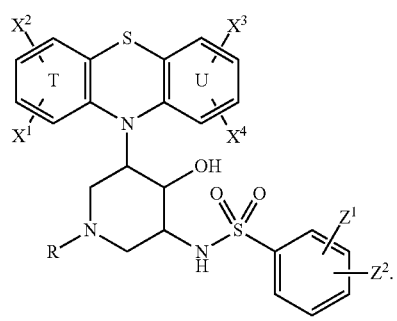

16. A compound according to claim 1, wherein $Z^1$ is hydrogen and $Z^2$ is hydrogen, fluoro, chloro, trifluoromethyl, methoxy, or trifluoromethoxy.

17. A compound according to claim 1, wherein V is phenyl.

18. A pharmaceutical composition comprising a pharmaceutically acceptable carrier and a compound according to claim 1.

19. A method for treating a disease in a patient chosen from:

(a) cancer (b) diabetes (c) autoimmune disease (d) age onset proteotoxic disease (e) mood disorder (f) acne vulgaris (g) solid organ transplant rejection (h) graft vs. host disease (i) cardiac hypertrophy (j) viral infection and (k) parasitic infection;

the method comprising administering to the patient a therapeutically effective amount of a compound according to claim 1.

20. A method for treating a disease or disorder in a patient where the disease or disorder involves the dysregulation of the PI3K-AKT-FOXO signaling pathway or the dysregulation of a Myc dependent signaling pathway, the method comprising administering to the patient a therapeutically effective amount of a compound according to claim 1.

* * * * *